US 8,541,221 B2

(12) United States Patent
Switzer et al.

(10) Patent No.: US 8,541,221 B2
(45) Date of Patent: *Sep. 24, 2013

(54) PRIMATE T-LYMPHOTROPIC VIRUSES

(75) Inventors: William M. Switzer, Stone Mountain, GA (US); Walid Heneine, Atlanta, GA (US); Thomas M. Folks, Helotes, TX (US); Nathan D. Wolfe, Los Angeles, CA (US); Donald S. Burke, Pittsburgh, PA (US); Eitel Mpoudi Ngole, Yaoundé (CM)

(73) Assignees: The United States of America as represented by the Secretary of the Department of Health and Human Services, Centers for Disease Control and Prevention, Washington, DC (US); Johns Hopkins University, Baltimore, MD (US)

( * ) Notice: Subject to any disclaimer, the term of this patent is extended or adjusted under 35 U.S.C. 154(b) by 223 days.

This patent is subject to a terminal disclaimer.

(21) Appl. No.: 12/829,125

(22) Filed: Jul. 1, 2010

(65) Prior Publication Data

US 2010/0317034 A1 Dec. 16, 2010

Related U.S. Application Data

(63) Continuation of application No. 11/678,596, filed on Feb. 24, 2007, now Pat. No. 7,794,998, which is a continuation-in-part of application No. PCT/US2006/005869, filed on Feb. 21, 2006.

(60) Provisional application No. 60/654,484, filed on Feb. 21, 2005.

(51) Int. Cl.
*C12N 7/00* (2006.01)
*C12N 7/04* (2006.01)

(52) U.S. Cl.
USPC .......... 435/236; 435/235.1; 930/10; 930/220; 930/221

(58) Field of Classification Search
None
See application file for complete search history.

(56) References Cited

U.S. PATENT DOCUMENTS 6,406,841 B1 6/2002 Lee et al.
7,794,998 B2 * 9/2010 Switzer et al. ............. 435/235.1

OTHER PUBLICATIONS

Barnhart et al., "Function of the human T-cell leukemia virus type 1 21-base-pair repeats in basal transcription," *J. Virol.* 71:337-344 (1997).

(Continued)

*Primary Examiner* — Zachsriah Lucas
*Assistant Examiner* — Stuart W Snyder
(74) *Attorney, Agent, or Firm* — Klarquist Sparkman, LLP

(57) ABSTRACT

Disclosed are compositions and methods related to the isolation and identification of the primate T-lymphotropic viruses, HTLV-3 and HTLV-4. The diversity of HTLVs was investigated among central Africans reporting contact with NHP blood and body fluids through hunting, butchering, and keeping primate pets. Herein it is shown that this population is infected with a variety of HTLVs, including two retroviruses; HTLV-4 is the first member of a novel phylogenetic lineage that is distinct from all known HTLVs and STLVs; HTLV-3 falls within the genetic diversity of STLV-3, a group that has not previously been seen in humans. The present disclosure also relates to vectors and vaccines for use in humans against infection and disease. The disclosure further relates to a variety of bioassays and kits for the detection and diagnosis of infection with and diseases caused by HTLV-3 and HTLV-4 and related viruses.

14 Claims, 23 Drawing Sheets

(56) References Cited

OTHER PUBLICATIONS

Barre-Sinoussi, et al., "Isolation of a T-lymphotropic retrovirus from a patient at risk for acquired immune deficiency syndrome (AIDS)," *Science* 220(4599): 868-871 (1983). Abstract Only.

Bindhu et al., "Role of accessory proteins of HTLV-1 in viral replication, T cell activation, and cellular gene expression," *Front. Biosci.* 9:2556-2576.(2004).

Calattini et al., "Discovery of a new human T-cell lymphotropic virus (HTLV-3) in Central Africa," *Retrovirology* 2:30 (2005).

Calattini et al., "Human T-cell lymphotropic virus type 3: complete nucleotide sequence and characterization of the human tax3 protein," *J. Virol.* 80:9876-9888 (2006).

Chevalier et al., "Molecular characterization of the Tax protein from the highly divergent simian T-cell lymphotropic virus type 3 strain," *AIDS Res. Hum. Retrovir.* 21:513 (Abs. P174) (2005).

Courgnard et al., "Simian T-Cell leukemia virus (STLV) infection in wild primate populations in Cameroon: evidence for dual STLV type 1 and type 3 infection in agile mangabeys (*Cercocebus agilis*)," *J. Virol.* 78:4700-4709 (2004).

Digilio et al., "The simian T-lymphotropic/leukemia virus from Pan paniscus belongs to the type 2 family and infects Asian macaques," *J. Virol.* 71:3684-3692 (1997).

Feuer & Green, "Comparative biology of human T-cell lymphotropic virus type 1 (HTLV-1) and HTLV-2," *Oncogene* 24:5996-6004 (2005).

Gaudray et al., "The complementary strand of the human T-cell leukemia virus type 1 RNA genome encodes a bZIP transcription factor that down-regulates viral transcription," *J. Virol.* 76:12813-12822 (2002).

Goubau et al., "A primate T-lymphotropic virus, PTLV-L, different from human T-lymphotropic viruses types I and II, in a wild-caught baboon (*Papio hamadryas*)," *Proc. Natl. Acad. Sci. USA* 91:2848-2852 (1994).

Leendertz et al., "High variety of different simian T-cell leukemia virus type 1 strains in chimpanzees (*Pan troglodytes verus*) of Tai National Park, Cote d'Ivoire," *J. Virol.* 78:4352-4356 (2004).

Lemey et al., "A Bayesian statistical analysis of human T-cell lymphotropic virus evolutionary rates," *Infect. Gen. Evol.* 5:291-298 (2005).

Lole et al., "Full-length human immunodeficiency virus type 1 genomes from subtype C-infected seroconverters in India, with evidence of intersubtype recombination," *J. Virol.* 73:152-160 (1999).

Mahieux et al., "Human T-cell lymphotropic virus type 1 gag indeterminate western blot patterns in Central Africa: relationship to *Plasmodium falciparum* infection," *J. Clin. Microbiol.* 3 8:4049-4057 (2000).

Mahieux et al., "Molecular epidemiology of 58 new African human T-cell leukemia virus type 1 (HTLV-1) strains: identification of a new and distinct HTLV-1 molecular subtype in central Africa and in pygmies," *J. Virol.* 71:1317-1333 (1997).

Mathews et al., "Expanded sequence dependence of thermodynamic parameters improves prediction of RNA secondary structure," *J. Mol. Biol.* 288:911-940 (1999).

Meertens and Gessain, "Divergent simian T-cell lymphotropic virus type 3 (STLV-3) in wild-caught Papio hamadryas papio from Senegal: widespread distribution of STLV-3 in Africa," *J. Virol.* 77:782-789 (2003).

Meertens et al., "A novel, divergent simian T-cell lymphotropic virus type 3 in a wild-caught red-capped mangabey (*Cercocebus torquatus torquatus*) from Nigeria," *J. Gen. Virol.* 84:2723-2727 (2003).

Meertens et al., "Complete sequence of a novel highly divergent simian T-cell lymphotropic virus from wild-caught red-capped mangabeys (*Cercocebus torquatus*) from Cameroon: a new primate T-lymphotropic virus type 3 subtype," *J. Virol.* 76:259-268 (2002).

Meertens et al., "Molecular and Phylogenetic Analyses of 16 Novel Simian T Cell Leukemia Virus Type 1 from Africa: Close Relationship of STLV-1 from *Allenopithecus nigroviridis* to HTLV-1 Subtype B Strains," *Virology* 287:275-285 (2001).

Nerrienet et al., "Simian T cell leukaemia virus type I subtype B in a wild-caught gorilla (Gorilla *gorilla gorilla*) and chimpanzee (*Pan troglodytes vellerosus*) from Cameroon," *J. Gen Virol.* 85:25-9 (2004).

Posada & Crandall, "Model Test: testing the model of DNA substitution," *Bioinformatics*, 14:817-818 (1998).

Robertson et al., "Recombination in HIV-1," *Nature* 374:124-126 (1995).

Romano et al., "Latest Developments in Gene Transfer Technology" Achievements, Perspectives, and Controversies over Therapeutic Applications, *Stem Cells* 18:19-39 (2000).

Rousset et al., "The C-terminus of the HTLV-1 Tax oncoprotein mediates interaction with the PDZ domain of cellular proteins," *Oncogene* 16:643-654 (1998).

Salemi et al., "Origin and evolution of human and simian T-cell lymphotropic viruses," *AIDS Rev.* 1:131-139 (1999).

Salemi et al., "Tempo and mode of human and simian T-lymphotropic virus (HTLV/STLV) evolution revealed by analyses of full-genome sequences," *Mol. Biol. Evol.* 17:374-386 (2000).

Sanderson, "r8s: inferring absolute rates of molecular evolution and divergence times in the absence of a molecular clock," *Bioinformatics* 19:301-2 (2003).

Satou et al., "HTLV-1 basic leucine zipper factor gene mRNA supports proliferation of adult T cell leukemia cells," *Proc. Natl. Acad. Sci. USA* 103:720-725 (2006).

Sharp et al., "Origins and evolution of AIDS viruses: estimating the time-scale," *Biochem. Soc. Trans.* 28:275-282 (2000).

Slattery et al., "Genomic evolution, patterns of global dissemination, and interspecies transmission of human and simian T-cell leukemia/lymphotropic viruses," *Genome Res.* 9:525-540 (1999).

Switzer et al., "Ancient co-speciation of simian foamy viruses and primates," *Nature* 434:376-380 (2005).

Switzer et al., "Ancient origin and molecular features of the novel human T-lymphotropic virus type 3 revealed by complete genome analysis," *J. Virol.* 80:7427-7438 (2006).

Switzer et al., "Phylogenetic relationship and geographic distribution of multiple human T-cell lymphotropic virus type II subtypes," *J. Virol.* 69:621-632 (1995).

Takemura et al., "High prevalence of simian T-lymphotropic virus type L in wild Ethiopian baboons," *J. Virol.* 76:1642-1648 (2002).

Thompson et al., "CLUSTAL W: Improving the sensitivity of progressive multiple sequence alignment through sequence weighting, position-specific gap penalties and weight matrix choice," *Nucleic Acids Res.* 22:4673-4680 (1994).

Tsubata et al., "PDZ domain-binding motif of human T-cell leukemia virus type 1 Tax oncoprotein is essential for the interleukin 2 independent growth induction of a T-cell line," *Retrovirology* 2:46 (2005).

Van Brussel et al., "Complete nucleotide sequence of the new simian T-lymphotropic virus, STLV-PH969 from a Hamadryas baboon, and unusual features of its long terminal repeat," *J. Virol.* 7:5464-5472 (1997).

Van Dooren et al., "Evidence for a second simian T-cell lymphotropic virus type 3 in *Cercopithecus nictitans* from Cameroon," *J. Virol.* 75(23):11939-41 (2001).

Van Dooren et al., "Identification in gelada baboons (*Theropithecus gelada*) of a distinct simian T-cell lymphotropic virus type 3 with a broad range of Western blot reactivity," *J. Gen Virol.* 85:507-519 (2004).

Wolfe et al., "Emergence of unique primate T-lymphotropic viruses among central African bushmeat hunters," *Proc. Natl. Acad. Sci. USA* 102:7994-7999 (2005).

Wolfe et al., "Exposure to nonhuman primates in rural Cameroon," *Emerg. Infect. Dis.* 10:2094-2099 (2004).

Wolfe et al., "Naturally acquired simian retrovirus infections in central African hunters," *Lancet* 363:932-937 (2004).

\* cited by examiner pol (662-bp)

env (297-bp)

tax (730-bp)

LTR (398-bp)

pol-env-tax (5258-bp)

FIG. 5A

TGTCGATGATGAGCCCGAGACGGTCACAACCACCAGCTAGAGGACAAATA

GCTGAGTCACCCGTCGAGAACCGTCTCACACCGGATTGTGCCAAAAGAACA

CCGGGGCTCTGAGCTCTCCTAGCTGGCTCCGGAAAAACCAAAAACCACCC
   ‾‾‾‾‾‾‾‾‾‾‾‾‾‾‾‾‾
        21 R

ATTTCCTCATGTTTGCCTAAGCTCTGACGATAACCCTAAAAAATTGACTAGCAA
                    ‾‾‾‾‾‾‾‾‾‾‾‾‾‾‾‾‾‾‾‾‾‾‾‾‾‾
                              21 R                U3|R

ATAAAGAACCCTGGCCTATAAAAGGGAGCAACCTAAACCTAAAAATGGGA CCTT
poly (A) signal    TATA box                        cap  ***

TTCTGCACCTCGCCAACCCCTCCTCGCCATCCTCGACTTGGTCATTCCTGCCT

ACCTGAATCGCCGCTTCGGGATCGAGCCATCCTCCTTCTATTGGTGGCACTTCGC

GCACTCCGCCGCCTTCCACTGGTAAGATCGCACTGGGTCGAGCTAGGCCATCACC
                         ‾‾‾‾‾‾‾‾‾
                         ▼ sd-LTR

CCTGGGCCGCTCCCCTCGGAGCTCTCGCGGGTCTTAAGGTTGCTCCCCCTCAG
                   R|U5

CAAAGGGCCCAGGGCTTTCTACTCCCTTGTTTCAAGTCTCTTCTTTTGGCGGTCG

ACCTAAATCGAAGTAGCCACTTCGTCGTCAGCAGGGCTTGGCCCCAGGCCA

GCGCCTGTAAGGTTACCCAGCTCGGAGTTGGGTCTCTAGAGAATCAGGGCTAAAG

CTGCTAGCCCTAGGAAAAGAAGGCAAACAGGTGGGGGCTCGTCGGGATTGATCACC
                                ‾‾‾‾‾‾‾‾‾‾‾‾‾‾‾‾‾‾‾‾‾‾
                                        PBS

*TCTCTGTATTGCCCTTCCCTGTCGAAGCC*

FIG. 6

HTLV-3(2026ND)

```
                   NLS
MAHFPGFGQSLLYGYPVYVFGDCVQADWCPISGGLCSARLHRHALLATCPEHQITWDPIDGRVVSSALQY  70
        CBP/P300 Binding
LIPRLPSFPTQRTTRTLKVLTPPTTAATPKIPPSFFHAVKKHTPFRNNCLELTLGEQLPAMSFPDPGLRP 140
                                                NES
QNIYTMWGSSVVCLYLYQLSPPMTWPLIPHVIFCHPEQLGAFLTRVPTKRLEELLYKIFLSTCAIIILPE 210

NCFPTTLFQPTRAPAVQAPWHTGLLPCQKEIATPGLIWTFTDGSPMISGPCPKEGQPSLVVQSSTFIFQQ 280
                              CR2 binding                           PDZ
FQTKASHPAFLLSHKLIHYSSFHSLHLLFEEYTTIPFSLLFNEKGANVDDDEPRDGSQPPARGQIAESPV 350
```

SEQ ID NO: 50

FIG. 7

ERRRRCREELEERKRQKKERRQQLDCIDMLGFEGFCDLLEGYIDFLERESQQLRAGCEESL
   Arginine rich                                Leucine Zipper

SEQ ID NO: 84

FIG. 10A

```
TGACAGGGACAACGACCCTCTCCCAGGGGCGACAGCAAGCCCCCAAGGACA
AAACTAGCAGGGACTAGTCATCAGCCAAAAAGGTCAACTGTCTCACACAAAT
AAGGATCCGAAGGTTCTGACGTCCAGCCCAGCCTCAAAACCAGGAAATCCA
TAGAAATGCACCTCGCCCTTACCCACTTCCCCTATCATGAAAAACAAAGGCT
GTGACGACTACCCCCTTCCCCAAAAAATTTGCTTAAACCATCAATAAAGACA
GCCTAGCCTATATAAGCATGAGGATGGTTCAGGAGGGGGCTCGCTCTCTTGC
CGATCGCCCTGCTCACCTCGAGTGTCCATCTCCTGGTCAATCAGTTGAGACGC
CGCCGGCTGCCGGTCTCCTGGTTGTCGCACCTCCTGAACCACCCCTTGGGTAA
GTCCCCCCTTGGTCCGAGCTTGGCTACGGTTTCTGTAGTCGCTCCCAGGGAAG
TCTCCGAGACTGCCCAAGCCTCTGCTTGCAAGGCTACGGCCCTCCACCCCTCT
TCCGCGTCCGTGTTAATCTCTTCGCGCCAACCGAAAACGAAAGCGCCTCCAG
CTCTCTTGGCCCGGGGCCAGGCCTGAGCCGCGCGGGCGCACCACCTTAAGCC
CGCTGTACTCAAACCCCTCCGGGAGGGGCCCTTTACAGTAGGCGCCCGTCCC
CCCGGGGGAAACATACAAGTGGGGCTCGTCCGGGATCTGTTCCGCTCTCGC
CGTTCCCCCCCTCCCACTATGGGTCAGACCCACACATCCAGTCCCGTCCCTAA
GGCCCCCAGGGGGCTCTCCACCCACCACTGGCTTAATTTCCTGCAGGCGGCTT
ACCGCCTGCAACCTGGACCCTCCGAATTCGATTTTCACCAGTTAAGACGATTC
CTTAAGCTAGCGCTCCAAACCCAGTCTGGTTAAACCCTATCGATTACTCCCT
CCTAGCCGGCCTAATCCCCAAGGGGTACCCCGGTCGGGTGACCGAGATCGTT
AATATCCTCCTCCGCGCTCATCCACCCCCAGCGCCCCGGCAATTTCCATGCC
CACGGCCACCGGCCCGGCCCCTGCCCCCAGCCTCAGGAGGCGCACACGCCC
CCCCCTTATGCGGAGCCTGCTGCGCTCCAGTGCCTTCCCATTATGCACTCCCA
CGGGGCCCCCTCGAGCCACCGCCCCTGGCAGATGAAAGACTTACAAGCCATT
AAACAAGAAATTAGCACCTCAGCTCCCGGCAGTCCTCAATTTATGCATACCA
TTCGACTTGCCATCCAGCAGTTTGACCCTACGGCTAAAGATCTACATGATCTT
TTGCAGTACTTGTGCTCGTCCCTTATTGTCTCCCTTCACCACCAACAGCTACA
AGCACTCATTGTGGAGGCAGAAACCCGAGGGTTGACAGGTTACAATCCTATG
GCAGGGCCCCTCCGGGTACAAGCAAACAACCCCGCCCAGCAAGGCCTCCAG
AGAGAATACCAAAGTCTTTGGCTGGCCGCCTTTGCGGCCCTGCCTGGTAACA
CCCGAGATCCTTCCTGGGCCGCAATATTGCAAGGCCTCGAGGAACCTTATTGT
GCCTTTGTAGAGCGCCTCAATGCGGCCCTCGATAATGGTCTACCTGAAGGCA
CACCAAAGGAACCCATCCTGCGGCCGCTGGCATACTCCAATGCCAACAAAGA
ATGCCAGAAACTCCTTCAGGCGCGGGGCCATACCAACAGTCCCCTTGGCGAA
ATGCTCCGAGCCTGTCAGGCTTGGACACCAAAGGATAAGACCAAAGTTCTAG
TAGTTCAGCCCCGTAAAACCCTCCAACACAACCGTGCTTCCGGTGTGGAAA
GGTGGGACACTGGAGCCGAGACTGCACTCAGCCTCGCCCCCTCCGGGGCCC
TGCCCCCTATGTCAGGACCCATCCCACTGGAAGCGAGATTGCCCCAGCTAA
AAACCCCGCCGGAGGCAGAAGAACCCCTCCTAGCGGATTTGCCTGCCCTTCT
CCCGGAGGAAAAAACTCCCCAGGGGGGAGAACTAGTCTCCCCCCGACCC
GGTAACGTGCCTTCCCTGCTTCCCCTTGTCTCCCTATGGCAGGCCCAACAATC
TCTCCTCAATATTAAAGTTTCCTTCTTCGATCGCCCACCCCTGGCATCACAGG
CGCTCCTGGACACCGGAGCCGGCCTCACTGTCATGCCCCAGGTTTTGGCTCGG
GGGCTCACGGACCTCCAGGACACCACCATTCTGGGGCCGGCGGTAAAACCC
ACTCCCAGTTTAAACTCCTACGGTGTCCGGTACATGTATACTTGCCCTTCCGT
AGGGCTCCCGTGTCCCTTCCCTCATGTCTAATTGACACCAAGAATGAGTGGAC
CATCATCGGCCGGGACGTCCTGCAGCAATGCCAGGGGGCCCTTTACTTACCG
```

FIG. 10B

```
GAGGACCTCCCGGCCCCGACCCAGTTATCCCCGGTGACCACCCCTGCAGTCA
TCGGCTTAGAACATCTTCCAGAGCCCCCAGAGGTCAGCCAGTTTCCTTTAAAC
CTGAACGCCTCCAGGCCCTAATAGACCTGGTCTCCAAGGCACTGGAGGCTGG
CCATATCGAACCTTACTCTGGACCAGGCAACAACCCAGTTTTCCCTGTTAAAA
AACCCAACGGCAAGTGGCGATTTATCCATGACCTCAGGGCCACTAATGCCAT
CACCACTACCCTTGCCTCGCCCTCCCCGGCCCCCTGATCTTACCAGCCTGC
CACAGGCCTTGCCCCATCTTCAGACCATCGATCTCACGGACGCTTTCTTCCAG
ATTCCCCTCCCAAAGCGATTCCAGCCCTACTTCGCCTTTACCATCCCCCAGCC
ATTAAATCATGGGCCTGGGAGCAGGTACGCTTGGACAGTCCTTCCCCAAGGC
TTCAAAAACAGCCCCACGCTCTTTGAGCAACAGCTGGCCAGCGTACTAGGCC
CAGCCCGAAAAGCCTTCCCCACATCCGTCATCGTCCAATACATGGACGACAT
CCTCTTGGCATGCCCCTCCCAGCACGAACTAGATCAGCTGGCCACCCTTACCG
CACAGCTATTGTCCTCTCATGGTCTCCCAGTTTCCCAGGAAAAAACCCAACGC
ACCCCAGGAAAAATACACTTCCTGGGCCAAATCATACATCCAGATCACATCA
CCTATGAAACCACCCCCACCATCCCCATTAAGGCACACTGGACCCTGACTGA
ACTGCAAACCCTCCTGGGGGAGCTCCAGTGGGTCTCCAAGGGGACTCCTGTC
CTCCGAGAACACCTTCACTGTCTCTACTCAGCCTTGAGAGGTCTCAAAGACCC
CCGGGACACTATCACCCTTCGTCATCCTCACCTCCACGCTCTCCACAACATTC
AGCAAGCCCTGCATCACAATTGCCGCGGTCGCCTTGACTCTACGCTCCCCCTC
CTTGGCCTCATCTTCCTCAGTCCATCCGGCACGACCTCAGTCCTCTTCCAGAC
AAATCATAAATGGCCCCTAGTCTGGCTCCACGCCCCCCATCCCCCGACCAGC
CTATGCCCCTGGGGGCACATACTCGCCTGCACTGTACTTACCCTTGACAAGTA
TGCCTTGCAGCACTATGGCCAACTATGCAAATCATTCCATCATAACATGTCCA
CCCAGGCCCTACACGATTTCGTAAAAAATTCCTCTCACCCCAGCGTCGCCATA
TTAATTCACCACATGCATCGGTTCTGTGATCTGGGCAGACAGCCACCGGGAC
CCTGGCGAACCCTCTTACAACTCCCGGCCCTTCTCCGGGAACCCCAGCTCCTC
AGGCCTGCATTTTCCCTATCCCCAGTGGTTATAGATCAGGCCCCTTGTCTGTT
CTCTGATGGGTCTCCCCAAAAGGCCGCCTATGTAATTTGGGACAAGGTCATTC
TCAGCCAGCGGTCGGTCCCCCTGCCCCCCATGCCAATAACTCAGCACAAAA
GGGGGAATTAGTCGGACTCCTCTTGGGCTTGCAAGCCGCACAGCCCTGGCCA
TCCCTTAACATTTTCCTAGACTCAAAGTTCCTCATCCGGTACCTCCAGTCCCTC
GCTTCCGGGGCCTTCCAAGGATCATCCACACACCACCGTCTCCAGGCGTCCCT
GCCCACACTCCTCCAGGGCAAGGTCGTGTATCTCCACCACACCCGCAGCCAC
ACCCAATTGCCTGATCCCATCTCGACCCTCAATGAATATACCGACTCTCTCAT
TGTCGCCCCGTAACCCCCTTGAAGCCTGAGGGCCTCCATGCCCTCACCCACT
GCAACCAACAGGCCCTCGTTTCCCACGGAGCCACCCCTGCACAGGCTAAGCA
ACTCGTGCAGGCCTGCCGCACCTGTCAAATCATTAACCCTCAACACCACATG
CCGCGTGGCCACATCCGCCGCGGCCACTTCCCAAACCACACATGGCAAGGAG
ATGTCACCCACCTTAAGCACAAACGGACCCGATACTGCCTCCACGTCTGGGT
GGATACCTTCTCAGGTGCGGTATCTTGTGTCTGCAAAAAGAAAGAAACTAGC
AGCGACCTTATCAAAACCCTCCTACATGCCATCTCCGTGCTAGGCAAGCCCTT
CTCTGTTAACACGGACAATGGACCCGCTTACCTTTCTCAGGAGTTCCACGAAT
TCTGTACCACCCTCTGCATCAAACACTCCACCCATATTCCCTACAATCCGACA
AGTTCAGGCCTGGTGGAGCGCACAAATGGCATTCTCAAGACACTACTATACA
AATATTTCCTAGACCACCCTGACCTCCCCCTAGAAAGCGCGGTTTCAAAGGCT
CTCTGGACCATTAACCATTTAAATGTCATGCGCCCTGTGGTAAGACTCGGTG
```

FIG. 10C

```
GCAGCTCCATCACACCCCCCCCTGCCTCCTATTTCCGAGTCCATACAAACCA
CTCCCACCAGGCTACATTGGTACTATTACAAAACCCCTGGACTTACCAACCA
GCGATGGAAAGGGCCCGTACAATCTCTCCAGGAAGCAGCAGGAGCAGCTCTC
CTTCAAGTCAGTGACGGCTCGCCCCAGTGGATCCCTTGGCGGCTCCTGAAGA
AGACTGTATGCCCAAAACCCGACGACCCCGAACCCGCAGGGCACGTCGAAA
CAGACCACCAACACCATGGGTAACGTACTCTTCTTAACTTTATTGGCCACCCT
GGGCATCCCAGTACTTCAGGCCAGCCGGTGTACAATCACGGTAGGTATCTCC
TCCTACCACTCCAGCCCTGCAGCCCAGCCCAGCCTTTATGTACCTGGGCCCT
CGACCTTGTGTCCATCACTAAGGACCAGCTCCTCTACCCCCCTGCCAAAACC
TGATCACCTATTCCAACTACCACAAGACCTACTCCCTGTATCTCTTCCCACAC
TGGGTACAAAAGCCACTCCGCCGGGGGCTTGGATACTACTCAGCCTCCTACT
CTGATCCTTGCTCCCTACAATGTCCCTACCTAGGAAGTCAATCATGGACTTGC
CCCTATACTGGCCCTGTCTCGAGCCCAACTTGGAGATTCTCCACAGATGTAAA
TTTCACCCAAGAAGTCAGCCGTGTCTCCCTAAAACTTCATTTCTCCAAATGTG
GTTCCTCCTTAACTCTGTTAATAGATGCCCCCGGTTACGATCCGCTGTGGTAC
CTCACATCCGAGCCTACTCAGGAACCCCCAACCCCTCCGCCACTAGTCAGCG
ACTCAGACCTAGAGCATGTCCTGACTCCTTCGGCCTCCTGGGCCTCCAAGATG
CTGACCCTCATCCACCTAACCTTGCAGAGCACCAACTATTCCTGTATGGTCTG
TATTGACCGCGCCAGCCTCTCTTCCTGGCACGTATTATACACTCCCAACATCT
CTAGTAATGCCCCCTCAAAACCCATCGTCCGCCCTTCCCTTGCCCTATCCGCC
CCGCGACCACAGCCCTTCCCCTGGACCCATTGCTATCAACCACAGGTGCAAG
CTGTAACCACCGCAAAGTGCAATAATTCCATCATACTTCCCCCATTTTCTCTC
TCTCCCTTGCCTGGTGCCCCTCTCACTAGGCGACGCCGGGCCGTCCCAGTGGC
GGTCTGGCTCGTTTCCGCTTTGGCCGCAGGGACAGGAATAGCAGGAGGTGTC
ACCGGGTCCTTATCCCTGGCCTCCAGTAGAAGTCTCCTGTCCGAAGTGGACA
AGGATATTTCCCACCTCACACGGGCCATTGTAAAAAACCACCAAAACATTCT
TCGAGTGGCCCAATATGCCGCCCAAAACAGGCGAGGGTTAGACCTCCTGTTC
TGGGAACAAGGGGGGCTGTGTAAAGCGATACAAGAACAATGCTGCTTCCTCA
ACATCAGCAATACCCATATTTCAGTCTTACAAGAGCGACCCCCTCTAGAAAC
TCGGGTAACTACTGGATGGGGCTTAAATTGGGATCTAGGACTCTCCCAGTGG
GCCCGTGAGGCTCTCCAGACTGGTATTACCCTTTGGCCCTCCTTCTGTTAATC
ATCATCCTCGGGCCCTGCATTATTCGCCAGCTGCAAGCCCTCCCCCAGAGGCT
ACAGCAGCGACCTGACCAGTACCCTCTCCTCAACCCTGAGACCCCTTTATAAT
AACTCCGCCAATACACCCAACAGGTCCCCATGGTTGACCCCTCTACCGTTCAC
CCACCCGCACTCCGCTAGACCTGACGAGTCCCCCCATATGTCCAAAGTCTGTT
CCAAGCCAGCTGATAACCGAAATAATTCTCCTAAGTTATGGTTACATTCCTCC
TCCAGATCCTTCCTTTCCTTCTCTAATACATCAATATAGCCTTGCAACAAGTC
ACAATACCCCTCAAACCCCAGCAGGTCCATGCACTTCCGTTGTGATGACGC
GCCTCTCTCCTTGCGCTTCCTCTCCCTCCTGCAATCGCTCCCTCCGCCGC
GCCTCCTTTTCCTCCTGTTCTCGCAGGAGCCGCTGAATCTCCGCCTGCTCGTCC
ACCAGGGCCCTCAGGCGAGACTTCCGGGTACCATCATTGGCGCCTCCCGACC
CCAGGGGCGGCCTTTGCGCGCACGACGAGCGCCGCTACCAGGCATCTCCTC
TGGTGTTGAGACCTTCTTTGCCCGATCCTCTGATGATAACCCCCTAAAAAATT
CTATAAAAAATTCCCCGTTATTTTTTTCAGCCCACTTCCCAGGATTCGGGCAG
AGCCTCCTCTATGGATACCCCGTCTATGTGTTTGGCGATTGTGTTCAAGCCGA
TTGGTGCCCCATCTCCGGTGGATTATGCTCCCCCCGCCTACATCGCCACGCCC
```

FIG. 10D

```
TCCTGGCCACCTGCCCCGAGCACCAGATCACCTGGGACCCCATCGATGGACG
AGTTGTCGGCTCGCCTCTCCAATACCTTATCCCTCGCCTCCCCTCCTTCCCCAC
CCAACGAACCTCCAAGACCCTCAAAGTCCTTACCCCACCAACCACTCCTGTC
ACCCCCAAGGTTCCACCCTCCTTCTTTCAGTCCGTGCGGAGGCACAGCCCCTA
CCGCAACGGATGTCTTGAAACAACCCTTGGAGAGCAGCTCCCCTCCCTTGCA
TTTCCTGAGCCAGGCCTCAGGCCCCAAAACGTCTACACCATCTGGGGAAAGA
CCATAGTGTGTCTATACATCTACCAGCTGTCCCCTCCCATGACCTGGCCCCTC
ATTCCCCATGTCATATTTTGCAACCCCAGGCAGCTTGGCGCTTTTCTAAGCAA
TGTGCCCCCCAAGCGATTAGAAGAACTCCTCTACAAACTTTATCTACACACCG
GCGCCATAATCATCCTGCCGGAAGACGCCCTGCCTACCACCCTATTTCAGCCT
GTTCGAGCACCCTGTGTCCAAACTACCTGGAACACAGGACTTCTCCCATACC
AGCCAAACCTGACTACCCCTGGCCTGATATGGACCTTTAATGATGGGTCTCCT
ATGATTTCAGGACCTTGCCCTAAGGCAGGGCAGCCATCCTTGGTAGTACAGT
CCTCACTACTAATCTTCGAGAGATTTCAAACCAAAGCCTATCATCCCTCTTAC
CTCCTCTCCCACCAATTGATACAGTATTCCTCCTTCCATCACCTCTACTTACTC
TTTGATGAATATACTACTATCCCCTTCTCTCTACTATTTAAGGAAAAAGAGGG
AGATGACAGGGACAACGACCCTCTCCCAGGGGCGACAGCAAGCCCCCAAGG
ACAAAACTAGCAGGGACTAGTCATCAGCCAAAAAGGTCAACTGTCTCACACA
AATAAGGATCCGAAGGTTCTGACGTCCCAGCCCAGCCTCAAAACCAGGAAAT
CCATAGAAATGCACCTCGCCCTTACCCACTTCCCCTATCATGAAAAACAAAG
GCTGTGACGACTACCCCCTTCCCCAAAAAATTTGCTTAAACCATCAATAAAG
ACAGCCTAGCCTATATAAGCATGAGGATGGTTCAGGAGGGGGCTCGCTCTCT
TGCCGATCGCCCTGCTCACCTCGAGTGTCCATCTCCTGGTCAATCAGTTGAGA
CGCCGCCGGCTGCCGGTCTCCTGGTTGTCGCACCTCCTGAACCACCCCTTGGG
TAAGTCCCCCCTTGGTCCGAGCTTGGCTACAGTTTCTGTAGTCGCTCCCAGGG
AAGTCTCCGAGACTGCCCAAGCCTCTGCTTGCAAGGCTACGGCCCTCCACCC
CTCTTCCGCGTCCGTGTTAATCTCTTCGCGCCAACCGAAAACGAAAGCGCCTC
CAGCTCTCTTGGCCCGGGGCCAGGCCTGAGCCGCGCGGGCGCACCACCTTAA
GCCCGCTGTACTCAAACCCCTCCGGGAGGGGCCCTTTACAGTAGGCGCCCGT
CCCCCCGGGGGAAACATACA
```

US 8,541,221 B2

SEQUENCE LISTING

<160> NUMBER OF SEQ ID NOS: 84

<210> SEQ ID NO 1
<211> LENGTH: 2670
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 1

| | | | | | |
|---|---|---|---|---|---|
| ggtcctccct | gtcctagcac | ccaagcttat | cggattagag | caccttcccc | cgccccaga | 60 |
| agtctctcag | ttcccgttaa | accagagcgc | ctccaggctc | tgactgacct | ggtttccagg | 120 |
| gccctggagg | ctaaacatat | agaacccdat | caaggaccag | gcaataaccc | tatcttcccc | 180 |
| gtcaaaaagc | ccaatgggaa | gtggcggttt | attcatgatc | tccgggccac | aaactccgtc | 240 |
| acccgagacc | tggcttcacc | gtcccccggc | cctccggacc | ttaccagtct | gccccaaggc | 300 |
| ctcccacatc | ttcggacaat | tgaccttact | gacgccttct | tccaaatccc | gctaccaacc | 360 |
| atttttcagc | cgtactttgc | attcactctc | ccccaaccga | caactatgg | tcccggaacc | 420 |
| agatactctt | ggagagtact | accccagggg | ttcaaaaata | gtccaacttt | atttgaacag | 480 |
| caactctccc | atatacttac | ccctgtgcgg | aaaacctttc | ctaattccct | tattatacaa | 540 |
| tatatggatg | acattctact | ggccagcccc | gccccggcg | agctagctgc | tctcaccgat | 600 |
| aaagtaacaa | acgccttaac | aaaggaaggc | ctgcccctat | ctccggaaaa | gactcaggcc | 660 |
| actcctggtc | ccatacattt | tcttggacaa | gtcatatccc | aggactgcat | aacatacgag | 720 |
| accctcccat | ccatcaatgt | aaaatccacc | tggtcactgg | cagaactaca | gtccatgcta | 780 |
| ggagaattac | aatgggtctc | taaaggcacc | cctgtcctcc | gctcctctct | acaccagctc | 840 |
| tatctcgctc | tccgaggcca | tcgtgaccct | cgggatacta | taaaattaac | ctcaatacag | 900 |
| gtacaagctc | taagaactat | tcagaaggcc | ttgaccctaa | actgccgaag | tagactagta | 960 |
| aatcagctgc | ccatcttggc | ccttataatg | ctccggccta | caggcaccac | ggcagtcctc | 1020 |
| ttccaaacaa | aacaaaagtg | gccactcgtc | tggttacaca | cccctcaccc | ggctaccagc | 1080 |
| ttgcgcccat | ggggacaact | attggccaac | gctgtcatca | tcctagacaa | atactcacta | 1140 |
| caacactatg | gccaagtatg | caaatcattt | catcataaca | tctctaatca | agccctcact | 1200 |
| tactacttac | atacatctga | ccaatccagc | gtagccatcc | tattacaaca | ctcacacaga | 1260 |
| tttcacaatc | tcggggcgca | gccatcaggg | ccatggagaa | gcctcttaca | aatgcccag | 1320 |
| attttccaaa | acatcgatgt | cctaaggcct | cctttaccα | tctcgcctgt | agtcatcaac | 1380 |
| catgcccct | gtctctttc | ggacgggtct | gcctccaagg | cagcatttat | catctgggat | 1440 |
| agacaagtca | tccaccaaca | ggtcctctcc | ctgcctcaa | cctgttcagc | tcaagcgggg | 1500 |
| gaactatttg | gcctgttggc | aggactacaa | aagtctcaac | cctgggtggc | actaaatata | 1560 |
| tttctagatt | caaaatttct | tatcgggcac | ctcaggcgaa | tggcattagg | gcctttcca | 1620 |
| ggaccatcca | cccagtgcga | attacacaca | cagcttctcc | cctgctgca | gggaaagact | 1680 |
| gtctatgtgc | accacgtaag | gagtcacact | cttctgcaag | acctatatc | ccgccttaat | 1740 |
| gaagccacag | atgccctcat | gcttgcccct | ctgttacccc | tcgacccac | aactctccac | 1800 |
| cagctcaccc | actgtaaccc | ttacgcccta | cgtaaccatg | gagccactgc | tctgaagcc | 1860 |
| catgcaattg | tgcaggcatg | tcacacatgc | aaggtcatca | acccacaggg | acggttaccc | 1920 |
| cagggatata | ttcgtcgagg | ccatgccccct | aatgatatct | ggcaagggga | cgtcactcac | 1980 |

```
ctccagtaca agcgatacaa atattgcctg ctggtttggg tagatactta ctccggggcg   2040
gtctctgtgt cctgccggcg caaggagacc ggctccgact gtgtcgcctc gttacttgtg   2100
gccatctcca ttctaggaaa accacaaaac atcaacaccg ataacggagc tgcgtatctc   2160
tcccaagagt tccaacagtt ttgcaactca cttgccatta acattcaac ccacattccc    2220 tacaacccca ccagctctgg cttggttgaa agaacaaatg gtattcttaa aactttgatt   2280
tccaaatatc tcctagacaa tcaccacctg ccctggaga cagccgtctc caaatccctc    2340
tggactataa accatcttaa tgtccttccc tcgtgccaaa agactcggtg gcagctacat    2400
caggcccagc ccctgcctcc cgtccctgaa gacacactcc caccccacac atcaccaaaa   2460
tggtattatt ataaaattcc tggtcttacc aactcaaggt ggagtgggcc tgtacaatcc   2520
ctcaaggaag cagcaggagc ggctctcatc ccagtaggtg gaagctatct ctggatcccg   2580
tggcgcctcc taaaaagggg tatatgccca agacccgaaa gcagcgcagc cgtcgaccca   2640
aaaaccagag accatcaact ccatgggtaa                                    2670

<210> SEQ ID NO 2
<211> LENGTH: 2549
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 2
ctggccatat cgaaccttac tctggaccag gcaacaaccc agttttccct gttaaaaaac    60
ccaacggcaa gtggcgattt atccatgacc tcagggccac taatgccatc accactaccc   120
ttgcctcgcc ctcccccggc cccctgatc ttaccagcct gccacaggcc ttgccccatc    180
ttcagaccat cgatctcacg gacgctttct tccagattcc cctcccaaag cgattccagc   240
cctacttcgc ctttaccatc ccccagccat taaatcatgg gcctgggagc aggtacgctt   300
ggacagtcct tccccaaggc ttcaaaaaca gccccacgct cttttgagcaa cagctggcca   360 gcgtactagg cccagcccga aaagccttcc ccacatccgt catcgtccaa tacatggacg   420
acatcctctt ggcatgcccc tcccagcacg aactagatca gctggccacc cttaccgcac   480
agctattgtc ctctcatggt ctcccagttt cccaggaaaa acccaacgc accccaggaa    540 aaatacactt cctgggccaa atcatacatc cagatcacat cacctatgaa accaccccca   600
ccatccccat taaggcacac tggacccctga ctgaactgca aaccctcctg ggggagctcc   660
agtgggtctc caaggggact cctgtcctcc gagaacacct tcactgtctc tactcagcct   720
tgagaggtct caaagacccc cgggacacta tcacccttcg tcatcctcac ctccacgctc   780
tccacaacat tcagcaagcc ctgcatcaca attgccgcgg tcgccttgac tctacgctcc   840
ccctccttgg cctcatcttc ctcagtccat ccggcacgac ctcagtcctc ttccagacaa   900
atcataaatg gcccctagtc tggctccacg ccccccatcc cccgaccagc ctatgcccct   960
gggggcacat actcgcctgc actgtactta cccttgacaa gtatgccttg cagcactatg   1020
gccaactatg caaatcattc catcataaca tgtccaccca ggcctacac gatttcgtaa    1080 aaaattcctc tcaccccagc gtcgccatat taattcacca catgcatcgg ttctgtgatc   1140
tgggcagaca gccaccggga ccctggcgaa ccctcttaca actcccggcc cttctccggg   1200
aaccccagct cctcaggcct gcattttccc tatcccagt ggttatagat caggccccctt    1260 gtctgttctc tgatgggtct ccccaaaagg ccgcctatgt aatttgggac aaggtcattc   1320
```

| | |
|---|---|
| tcagccagcg gtcggtcccc ctgccccccc atgccaataa ctcagcacaa aaggggggaat | 1380 |
| tagtcggact cctcttgggc ttgcaagccg cacagccctg gccatccctt aacatttcc | 1440 |
| tagactcaaa gttcctcatc cggtacctcc agtccctcgc ttccggggcc ttccaaggat | 1500 |
| catccacaca ccaccgtctc caggcgtccc tgcccacact cctccagggc aaggtcgtgt | 1560 |
| atctccacca cacccgcagc cacacccaat tgcctgatcc catctcgacc ctcaatgaat | 1620 |
| ataccgactc tctcattgtc gcccccgtaa cccccttgaa gcctgagggc ctccatgccc | 1680 |
| tcacccactg caaccaacag gccctcgttt cccacggagc caccccctgca caggctaagc | 1740 |
| aactcgtgca ggcctgccgc acctgtcaaa tcattaaccc tcaacaccac atgccgcgtg | 1800 |
| gccacatccg ccgcggccac ttcccaaacc acacatggca aggagatgtc acccacctta | 1860 |
| agcacaaacg gacccgatac tgcctccacg tctgggtgga taccttctca ggtgcggtat | 1920 |
| cttgtgtctg caaaagaaa gaaactagca gcgaccttat caaaaccctc ctacatgcca | 1980 |
| tctccgtgct aggcaagccc ttctctgtta acacggacaa tggacccgct tacctttctc | 2040 |
| aggagttcca cgaattctgt accaccctct gcatcaaaca ctccacccat attccctaca | 2100 |
| atccgacaag ttcaggcctg gtggagcgca caaatggcat tctcaagaca ctactataca | 2160 |
| aatatttcct agaccaccct gacctccccc tagaaagcgc ggtttcaaag gctctctgga | 2220 |
| ccattaacca tttaaatgtc atgcgcccct gtggtaagac tcggtggcag ctccatcaca | 2280 |
| ccccccccct gcctcctatt tccgagtcca tacaaaccac tccaccagg ctacattggt | 2340 |
| actattacaa aaccccctgga cttaccaacc agcgatggaa agggcccgta caatctctcc | 2400 |
| aggaagcagc aggagcagct ctccttcaag tcagtgacgg ctcgcccccag tggatcccctt | 2460 |
| ggcggctcct gaagaagact gtatgcccaa aacccgacga ccccgaaccc gcagggcacg | 2520 |
| tcgaaacaga ccaccaacac catgggtaa | 2549 |

<210> SEQ ID NO 3
<211> LENGTH: 1476
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 3

| | |
|---|---|
| atgggtaagt tctgccttta tttctgtctt atttacatac tcttctctgc ctcctctggc | 60 |
| aatcccagtc gatgcaccct gttcatagga gcctcttcct accactccga cccctgcggg | 120 |
| tccgatcacc cgcggtgtac ctggagactc gacctatttt ctctcacaag agatcaaagc | 180 |
| ctaagccccc catgtccaga cttagttact tactcacagt atcataggcc ctactccctg | 240 |
| tatgtattcc cccattggat aaccaaacct aaccgtcgag gcctaggtta ctattctgct | 300 |
| tcctactcag accctgcgc tatacaatgc ccttacttag gatgccagtc atggacatgt | 360 |
| ccttatacag gcccggtgtc cagcccacat tggaaatact cctccgatct taattttacc | 420 |
| caagaagtat catccatctc cctacacttg cacttttcca aatgtgggtc tcattctcc | 480 |
| tttctactag acgcaccagg atatgatcca gtgtggttcc tctcctccca ggccacacag | 540 |
| gccccaccca cgcctgcccc tctcatacag gactcagatc tccaacatat cctagaacct | 600 |
| tccatcccct ggagctccaa aatcctcaat ctcatcctcc ttaccctaaa aagctctaat | 660 |
| tattcttgca tggtctgtgt tgaccgctcc agcctatctt cgtggcatgt tctatatgac | 720 |
| ccacttaaag cccccaatcc acccgacccc aaagcccagt ctattctgcg accctcccta | 780 |
| gccattcccg ccagtaatgt caccccgcca tttccttgga cccattgcta tcgccccctt | 840 |

| | |
|---|---|
| ctacaggcca tctcctcgga acactgcaat aactccgtag tactgccccc cttttccctg | 900 |
| tccccacttc ctaacgtctc cagaccccga aagcgccgag cagtccccat tgccatatgg | 960 |
| ctagtgtccg ccctagcggc cggcaccggt atagctggcg gagttaccgg ctccctgtct | 1020 |
| ctggcctcca gtaaaagcct actgcgcgaa gtagaccagg atatagatca cctgacgcag | 1080 |
| gcgattgtaa aaaccatga taatatcctt cgggttgctc aatacgcagc ccaaaatcgc | 1140 |
| cgtggcctag atttactttt ctgggaacaa gggggccttt gtaaggccat ccaagaacaa | 1200 |
| tgttgcttcc ttaatatcag caacacccat gtgtccgtcc tccaggaaag acccccccta | 1260 |
| gaaaagagag taatcactgg ctggggactc aactgggacc tcgggctctc ccaatgggcc | 1320 |
| cgagaggccc ttcagacagg tataacactt ttagcccttt ttctcctcct catcgttgta | 1380 |
| ggaccctgcg tcatacgcca gctacaggcc ctcccttccc gtctgcagca tcgcagtcag | 1440 |
| ccctactccc ttctcaatta tgaaaccaac ttataa | 1476 |

<210> SEQ ID NO 4
<211> LENGTH: 1458
<212> TYPE: DNA
<213> ORGANISM: Artificial Sequence
<220> FEATURE:
<223> OTHER INFORMATION: Description of Artificial Sequence;
      note=synthetic construct <400> SEQUENCE: 4

| | |
|---|---|
| atgggtaacg tactcttctt aactttattg gccaccctgg gcatcccagt acttcaggcc | 60 |
| agccggtgta caatcacggt aggtatctcc tcctaccact ccagcccctg cagcccagcc | 120 |
| cagcctttat gtacctgggc cctcgacctt gtgtccatca ctaaggacca gctcctctac | 180 |
| ccccccctgcc aaaacctgat cacctattcc aactaccaca gacctactc cctgtatctc | 240 |
| ttcccacact gggtacaaaa gccactccgc cgggggcttg gatactactc agcctcctac | 300 |
| tctgatcctt gctccctaca atgtccctac ctaggaagtc aatcatggac ttgcccctat | 360 |
| actggccctg tctcgagccc aacttggaga ttctccacag atgtaaattt cacccaagaa | 420 |
| gtcagccgtg tctccctaaa acttcatttc tccaaatgtg gttcctcctt aactctgtta | 480 |
| atagatgccc ccggttacga tccgctgtgg tacctcacat ccgagcctac tcaggaaccc | 540 |
| ccaaccccctc cgccactagt cagcgactca gacctagagc atgtcctgac tccttcggcc | 600 |
| tcctgggcct ccaagatgct gaccctcatc cacctaacct tgcagagcac caactattcc | 660 |
| tgtatggtct gtattgaccg cgccagcctc tcttcctggc acgtattata cactcccaac | 720 |
| atctctagta atgccccctc aaaacccatc gtccgccctt cccttgccct atccgccccg | 780 |
| cgaccacagc ccttcccctg gacccattgc tatcaaccac aggtgcaagc tgtaaccacc | 840 |
| gcaaagtgca ataattccat catacttccc ccattttctc tctctccctt gcctggtgcc | 900 |
| cctctcacta ggcgacgccg ggccgtccca gtggcggtct ggctcgtttc cgctttggcc | 960 |
| gcagggacag gaatagcagg aggtgtcacc gggtccttat ccctggcctc cagtagaagt | 1020 |
| ctcctgtccg aagtggacaa ggatatttcc cacctcacac gggccattgt aaaaaaccac | 1080 |
| caaaacattc ttcgagtggc ccaatatgcc gcccaaaaca ggcgagggtt agacctcctg | 1140 |
| ttctgggaac aagggggggct gtgtaaagcg atacaagaac aatgctgctt cctcaacatc | 1200 |
| agcaataccc atatttcagt cttacaagag cgaccccctc tagaaactcg ggtaactact | 1260 |
| ggatgggct taaattggga tctaggactc tcccagtggg cccgtgaggc tctccagact | 1320 |
| ggtattaccc ttttggcccct ccttctgtta atcatcatcc tcgggccctg cattattcgc | 1380 |

```
cagctgcaag ccctccccca gaggctacag cagcgacctg accagtaccc tctcctcaac    1440
cctgagaccc ctttataa                                                   1458

<210> SEQ ID NO 5
<211> LENGTH: 1053
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 5
atggcccatt tcccaggttt cggacagagc cttctctacg gtaccctgt ctacgttttc       60 ggcgactgtg tacaggccga ttggtgcccc atttctgggg ggctttgttc cgctcggcta     120
caccgccatg ccctactggc cacgtgcccc gaacatcaga ttacctggga ccccatcgat     180
ggacgcgttg tcagctcagc tctacaaatac cttatccctc gactccctc cttccccacc    240 cagagaacta cccgcaccct caaggttctc accccccaa ccactgctgc gaccccaag      300 attcctccat ccttcttcca cgccgttaaa aaacacaccc ccttccgaaa caattgcctt    360
gaactcaccc tgggagagca gttgccagcc atgtccttcc ccgaccctgg gctccgaccc    420
caaaacatct acaccatgtg gggaagctcc gttgtgtgcc tttacctcta tcagctctcc    480 cccccatga cctggcctct aatcccgcat gttatattct gccatcctga gcagcttgga    540
gccttcctca cccgagtccc taccaaacga ttagaagaac tcctgtataa gatattttta    600
agcacagggg cgataatcat cctgcctgaa aactgttttc caaccaccct gttccaaccc    660
acccgcgcgc ccgcggtgca ggccccctgg cacacaggcc tgctcccgtg tcaaaaggaa    720
attgctaccc ccgggctcat ttggactttc actgatggca gccccatgat ttccggccct    780
tgccccaaag aaggacagcc atctttagta gtacaatcat ctacatttat ctttcaacaa    840
ttccaaacca aggccagtca ccccgctttc ctcttgtccc acaaactaat ccactactcc    900
tcttttcatt ccctccacct cctctttgag gaatatacaa ctatccccctt ttctctactt    960 tttaatgaaa aaggggcaaa tgtcgatgat gatgagcccc gagacgggtc acaaccacca   1020
gctagaggac aaatagctga gtcacccgtc tga                                 1053

<210> SEQ ID NO 6
<211> LENGTH: 765
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 6
atggcccact tcccaggatt cgggcagagc ctcctctatg ataccccgt ctatgtgttt      60 ggcgattgtg ttcaagccga ttggtgcccc atctccggtg gattatgctc ccccgccta    120 catcgccacg ccctcctggc cacctgcccc gagcaccaga tcacctggga ccccatcgat    180
ggacgagttg tcggctcgcc tctccaatac cttatccctc gctcccctc cttccccacc    240 caacgaacct ccaagaccct caaagtcctt accccaccaa ccactcctgt caccccaag    300 gttccacccct cctttctttca gtccgtgcgg aggcacagcc ctaccgcaa cggatgtctt    360 gaaacaaccc ttggagagca gctccctcc cttgcatttc ctgagccagg cctcaggccc    420
caaaacgtct acaccatctg gggaagacc atagtgtgtc tatacatcta ccagctgtcc    480
cctcccatga cctggcccct cattcccat gtcatatttt gcaaccccag gcagcttggc    540
```

```
gcttttctaa gcaatgtgcc ccccaagcga ttagaagaac tcctctacaa actttatcta    600
cacaccggcg ccataatcat cctgccggaa gacgccctgc ctaccaccct atttcagcct    660
gttcgagcac cctgtgtcca aactacctgg aacacaggac ttctcccata ccagccaaac    720
ctgactaccc ctggcctgat atggaccttt aatgatgggt ctcct                   765
```

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 7

```
tyacctrgga ccccatcgat ggacg                                          25
```

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence;
      note=synthetic construct
<220> FEATURE:
<221> NAME/KEY: misc_feature
<222> LOCATION: (1)...(26)
<223> OTHER INFORMATION: n = inosine

<400> SEQUENCE: 8

```
gangaytgna stacyaaaga tggctg                                         26
```

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct
<220> FEATURE:
<221> NAME/KEY: misc_feature
<222> LOCATION: (1)...(24)
<223> OTHER INFORMATION: n = inosine

<400> SEQUENCE: 9

```
ccttatccct cgnctcccct cctt                                           24
```

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence;
      note=synthetic construct
<220> FEATURE:
<221> NAME/KEY: misc_feature
<222> LOCATION: (1)...(23)
<223> OTHER INFORMATION: n = inosine

<400> SEQUENCE: 10

```
ttngggyang gnccggaaat cat                                            23
```

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct

```
<220> FEATURE:
<221> NAME/KEY: misc_feature
<222> LOCATION: (1)...(24)
<223> OTHER INFORMATION: n = inosine

<400> SEQUENCE: 11
ckttaaaccn garcgcctcc aggc                                              24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct
<220> FEATURE:
<221> NAME/KEY: misc_feature
<222> LOCATION: (1)...(24)
<223> OTHER INFORMATION: n = inosine

<400> SEQUENCE: 12
ggyrtgnarc carrcnagkg gcca                                              24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 13
acytggtyys sarggccctg gagg                                              24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct
<220> FEATURE:
<221> NAME/KEY: misc_feature
<222> LOCATION: (1)...(24)
<223> OTHER INFORMATION: n = inosine

<400> SEQUENCE: 14
gryrggngtn cctttngaga ccca                                              24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 15
ctccttcttt cagtccgtgc ggag                                              24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 16
```

```
ggggtagtca ggtttggctg gtat                                          24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 17
cctaccgcaa cggatgtctt gaaa                                          24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 18
tatggcgccg gtgtgatgat aaag                                          24

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 19
aaccacccat ttcctcccca tg                                            22

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 20
gtcgtgaatg aaagggaaag gggt                                          24

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 21
tgacgacaac ccctcacctc aa                                            22

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 22
aggggtggaa ctttcgatct gtaa                                          24
```

```
<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 23
ttgtcatcag cccacttccc agg                                              23

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 24
aaggagggga gtcgagggat aagg                                             24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 25
cccaggtttc gggcaaagcc ttct                                             24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 26
aaggagggga gtcgagggat aagg                                             24

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence;
      note=synthetic construct
<220> FEATURE:
<221> NAME/KEY: misc_feature
<222> LOCATION: (1)...(23)
<223> OTHER INFORMATION: n = inosine

<400> SEQUENCE: 27
tggatcccgt ggmgnytcct naa                                              23

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct
<220> FEATURE:
<221> NAME/KEY: misc_feature
<222> LOCATION: (1)...(24)
```

```
<223> OTHER INFORMATION: n = inosine

<400> SEQUENCE: 28
gtrtangsrs angtccangm ytgg                                              24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct
<220> FEATURE:
<221> NAME/KEY: misc_feature
<222> LOCATION: (1)...(24)
<223> OTHER INFORMATION: n = inosine

<400> SEQUENCE: 29
anagaccwyc aacwccatgg gtaa                                              24

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence;
      note=synthetic construct
<220> FEATURE:
<221> NAME/KEY: misc_feature
<222> LOCATION: (1)...(23)
<223> OTHER INFORMATION: n = inosine

<400> SEQUENCE: 30
gmytggcanc cnargtangg gca                                               23

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence;
      note=synthetic construct
<220> FEATURE:
<221> NAME/KEY: misc_feature
<222> LOCATION: (1)...(27)
<223> OTHER INFORMATION: n = inosine

<400> SEQUENCE: 31
rccaccanct ngnggacaaa tagctga                                           27

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 32
cygggccaag cctcgctgca ggca                                              24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct
<220> FEATURE:
<221> NAME/KEY: misc_feature
```

```
<222> LOCATION: (1)...(24)
<223> OTHER INFORMATION: n = inosine

<400> SEQUENCE: 33
accnnggctc tgacgtctct ccct                                              24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence;
      note=synthetic construct
<220> FEATURE:
<221> NAME/KEY: misc_feature
<222> LOCATION: (1)...(24)
<223> OTHER INFORMATION: n = inosine

<400> SEQUENCE: 34
ggcagnagaa gtgctacttt cgat                                              24

<210> SEQ ID NO 35
<211> LENGTH: 1268
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 35
atgggaaaga cttatagctc cccaataaac cctatcccca agcccccaaa ggggctagca        60
attcaccact ggctgaactt cctccaggct gcgtaccgac tgcagccagg gccttctgaa       120
ttcgatttcc accagttacg aaagtttcta aaacttgcta ttaagacccc ggtatggtta       180
aatcccatta attactctgt cctcgccgga ctcatcccaa aaaactaccc cggcagggtt       240
catgaaatag tggccatcct aattcaagag accccctgcac gggaggcgcc cccgtcagct       300
ccgctagcag aggaccctca aaagcctcca ccctatcccg agcaggcgca ggaggcatct       360
cagtgcctcc ccatccttca cccccatggg gccccagccg ctcatcggcc ctggcaaatg       420
aaggatctcc aggctattaa acaggaagtc agctcttccg cccctggtag cccccagttc       480
atgcagacta tacgcttggc tgtccagcaa tttgatccca cagcaaaaga tctccacgat       540
ctcctacagt acctgtgctc ttccttagtt gcctccctgc accatcagca acttgagacc       600
ctcatagctc aggcggaaac ccaaggtata acaggatata accccctggc cggcccctta       660
cgaatacagg ccaacaatcc aaatcaacaa gggctccgaa agaatatca gaacctgtgg        720 ttatcggcct tttccgccct cccggggaac accaaggacc ccacctgggc agctatcctc       780
cagggacctg aagaaccctt tggctctttt gtagaaagac tcaatgtggc tttagataat       840
ggccttcccg aaggaaccccc caaagatcca atccttaggt ccctcgccta ttcaaatgct       900
aacaaggagt gccaaaaact cctacaggcc cgaggacaaa ccaacagccc gctagggaa        960 atgctcaggg cctgccaaac ttggacgccc cgagataaaa acaaaatact aatggtacaa      1020
cctaaaaaaa ctcctccccc gaaccagcca tgcttccgct gcgggcaagt aggtcattgg      1080
agcagagatt gtaaacagcc tcggccccct ccgggcccct gccccgtgtg tcaggatccc      1140
acccactgga agcgggactg cccacagtta aaaacagata ccagagacag cgaggaccta      1200
ctcctagacc tgccctgtga agcacccaat gtccgggaac gaaaaaactc ctcaggggg       1260 gaggatta                                                             1268
```

<210> SEQ ID NO 36
<211> LENGTH: 8917
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 36

| | | | | | |
|---|---|---|---|---|---|
| tgtcgatgat | gatgagcccc | gagacgggtc | acaaccacca | gctagaggac | aaatagctga | 60 |
| gtcaccgtc | tgagaaccgt | ctcacaccgg | gattgtgccc | aaaagaaca | ccggggctct | 120 |
| gacgtctctc | cctaccctgg | ctcccggaaa | aaccaaaaa | ccacccattt | cctcatgttt | 180 |
| gcctaaagct | ctgacgataa | ccctaaaaaa | tttgactagc | aaataaagaa | ccctgggccc | 240 |
| tataaagggg | gagagcaacc | taaaaatggg | atccttttc | tgcacctcgc | caaccctcc | 300 |
| tctggccacg | gtccgacttt | ggtcattcct | gcctacctga | atcgccgctt | cgggatcgag | 360 |
| ccatccctct | tctatttggt | ggcacttcgc | gcactccgcc | gccttccact | cggtaagatc | 420 |
| ccactgggtc | gagctaggcc | atcacccctg | ggccgctccc | ctggagctct | ctcgcgcggc | 480 |
| tcttaaggtt | gctccccctc | agcaaagggc | ccagggcttt | ctctacttcc | ttgtttcaag | 540 |
| tctctttctt | tggcggtcga | cctaaatcga | aagtagcact | tctgctgtca | gcagcgaggc | 600 |
| ttggcccagg | gccagcgcct | gtaaggttac | ccagctcgga | gttgggtctc | tagagaatca | 660 |
| gggctaaagc | tgctagccct | aggaaagaag | gcaaacaggt | gggggctcgt | ccgggattga | 720 |
| tcacctctct | gtatttgccc | ttccctgtcg | aagccatggg | aaagacttat | agctccccaa | 780 |
| taaaccctat | ccccaaagcc | ccaaagggc | tagcaattca | ccactggctg | aacttcctcc | 840 |
| aggctgcgta | ccgactgcag | ccagggcctt | ctgaattcga | tttccaccag | ttacgaaagt | 900 |
| ttctaaaact | tgctattaag | accccggtat | ggttaaatcc | cattaattac | tctgtcctcg | 960 |
| ccggactcat | cccaaaaaac | taccccggca | gggttcatga | aatagtggcc | atcctaattc | 1020 |
| aagagacccc | tgcacgggag | gcgccccgt | cagctccgct | agcagaggac | cctcaaaagc | 1080 |
| ctccacccta | tcccgagcag | gcgcaggagg | catctcagtg | cctccccatc | cttcaccccc | 1140 |
| atggggcccc | agccgctcat | cggccctggc | aaatgaagga | tctccaggct | attaaacagg | 1200 |
| aagtcagctc | ttccgcccct | ggtagccccc | agttcatgca | gactatacgc | ttggctgtcc | 1260 |
| agcaatttga | tcccacagca | aaagatctcc | acgatctcct | acagtacctg | tgctcttcct | 1320 |
| tagttgcctc | cctgcaccat | cagcaacttg | agaccctcat | agctcaggcg | gaaacccaag | 1380 |
| gtataacagg | atataacccc | ctggccggcc | ccttacgaat | acaggccaac | aatccaaatc | 1440 |
| aacaagggct | ccgaaaagaa | tatcagaacc | tgtggttatc | ggccttttcc | gccctcccgg | 1500 |
| ggaacaccaa | ggaccccacc | tgggcagcta | tcctccaggg | acctgaagaa | ccctttggct | 1560 |
| cttttgtaga | aagactcaat | gtggctttag | ataatggcct | tcccgaagga | accccaaag | 1620 |
| atccaatcct | taggtccctc | gcctattcaa | atgctaacaa | ggagtgccaa | aaactcctac | 1680 |
| aggcccgagg | acaaaccaac | agcccgctag | ggaaatgct | cagggcctgc | caaacttgga | 1740 |
| cgccccgaga | taaaaacaaa | atactaatgg | tacaacctaa | aaaaactcct | ccccgaacc | 1800 |
| agccatgctt | ccgctgcggg | caagtaggtc | attggagcag | agattgtaaa | cagcctcggc | 1860 |
| cccctccggg | cccctgcccc | gtgtgtcagg | atcccaccca | ctggaagcgg | gactgccac | 1920 |
| agttaaaaac | agataccaga | gacagcgagg | acctactcct | agacctgccc | tgtgaagcac | 1980 |
| ccaatgtccg | ggaacgaaaa | aactcctcag | gggggagga | ttagcctccc | ccgaaccat | 2040 |
| actcccccctt | ataccttgt | cccagcagaa | gcagcctacc | ctgcatatcc | aggtatcgtt | 2100 |

```
ttccaacacc cccctgtta gcgttcaggc gctcctcgac actggagcag acatcactgt    2160
cctcccggcc tgcttatgcc ctcccgattc caacctccag acaccactg tcctaggtgc    2220
aggcgggcca agtaccaaca agtttaaaat cctgccctgt ccagtccata tccacttgcc    2280
ttttcgaagg cagccggtga ccctaaccgc ttgcctaatt gatattaaca accagtggac    2340
catattaggg cgagatgccc tacaacaatg tcaaagttcc ctctatctgg ctgaccaacc    2400
ctctaaggtc ctccctgtcc tagcacccaa gcttatcgga ttagagcacc ttccccgcc     2460
cccagaagtc tctcagttcc cgttaaacca gagcgcctcc aggctctgac tgacctggtt    2520
tccagggccc tggaggctaa acatatagaa ccctatcaag gaccaggcaa taaccctatc    2580
ttccccgtca aaaagcccaa tgggaagtgg cggtttattc atgatctccg ggccacaaac    2640
tccgtcaccc gagacctggc ttcaccgtcc ccggccctc cggaccttac cagtctgccc     2700
caaggcctcc cacatcttcg gacaattgac cttactgacg ccttcttcca atcccgcta    2760
ccaaccattt ttcagccgta ctttgcattc actctcccc aaccgaacaa ctatggtccc     2820
ggaaccagat actcttggag agtactaccc caggggttca aaaatagtcc aactttattt    2880
gaacagcaac tctcccatat acttacccct gtgcggaaaa cctttcctaa ttcccttatt    2940
atacaatata tggatgacat tctactggcc agccccgccc ccggcgagct agctgctctc    3000
accgataaag taacaaacgc cttaacaaag gaaggcctgc ccctatctcc ggaaaagact    3060
caggccactc ctggtcccat acattttctt ggacaagtca tatcccagga ctgcataaca    3120
tacgagaccc tcccatccat caatgtaaaa tccacctggt cactggcaga actacagtcc    3180
atgctaggag aattacaatg ggtctctaaa ggcacccctg tcctccgctc ctctctacac    3240
cagctctatc tcgctctccg aggccatcgt gaccctcggg atactataaa attaacctca    3300
atacaggtac aagctctaag aactattcag aaggccttga ccctaaactg ccgaagtaga    3360
ctagtaaatc agctgcccat cttggcccctt ataatgctcc ggcctacagg caccacggca    3420
gtcctcttcc aaacaaaaca aaagtggcca ctcgtctggt tacacacccc tcacccggct    3480
accagcttgc gcccatgggg acaactattg gccaacgctg tcatcatcct agacaaatac    3540
tcactacaac actatggcca agtatgcaaa tcatttcatc ataacatctc taatcaagcc    3600
ctcacttact acttacatac atctgaccaa tccagcgtag ccatcctatt acaacactca    3660
cacagatttc acaatctcgg ggcgcagcca tcagggccat ggagaagcct cttacaaatg    3720
ccccagattt tccaaaacat cgatgtccta aggcctcctt ttaccatctc gcctgtagtc    3780
atcaaccatg ccccctgtct cttttcggac gggtctgcct ccaaggcagc atttatcatc    3840
tgggatagac aagtcatcca ccaacaggtc ctctccctgc cctcaacctg ttcagctcaa    3900
gcggggggaac tatttggcct gttggcagga ctacaaaagt ctcaaccctg ggtggcacta    3960
aatatatttc tagattcaaa atttcttatc gggcacctca ggcgaatggc attaggggcc    4020
tttccaggac catccaccca gtgcgaatta cacacacagc ttctccccct gctgcaggga    4080
aagactgtct atgtgcacca cgtaaggagt cacactcttc tgcaagaccc tatatcccgc    4140
cttaatgaag ccacagatgc cctcatgctt gcccctctgt tacccctcga ccccacaact    4200
ctccaccagc tcacccactg taacccttac gccctacgta accatggagc cactgcctct    4260
gaagcccatg caattgtgca ggcatgtcac acatgcaagg tcatcaaccc acagggacgg    4320
ttaccccagg gatatattcg tcgaggccat gcccctaatg atatctggca aggggacgtc    4380
actcacctcc agtacaagcg atacaaatat tgcctgctgg tttgggtaga tacttactcc    4440
ggggcggtct ctgtgtcctg ccggcgcaag gagaccggct ccgactgtgt cgcctcgtta    4500
```

```
cttgtggcca tctccattct aggaaaacca caaaacatca acaccgataa cggagctgcg    4560
tatctctccc aagagttcca acagttttgc aactcacttg ccattaaaca ttcaacccac    4620
attccctaca accccaccag ctctggcttg gttgaaagaa caaatggtat tcttaaaact    4680
ttgatttcca aatatctcct agacaatcac cacctgcccc tggagacagc cgtctccaaa    4740
tccctctgga ctataaacca tcttaatgtc cttccctcgt gccaaaagac tcggtggcag    4800
ctacatcagg cccagcccct gcctcccgtc cctgaagaca cactcccacc ccacacatca    4860
ccaaaatggt attattataa aattcctggt cttaccaact caaggtggag tgggcctgta    4920
caatccctca aggaagcagc aggagcggct ctcatcccag taggtggaag ctatctctgg    4980
atcccgtggc gcctcctaaa aagggtata tgcccaagac ccgaaagcag cgcagccgtc    5040
gacccaaaaa ccagagacca tcaactccat gggtaagttc tgcctttatt tctgtcttat    5100
ttacatactc ttctctgcct cctctggcaa tcccagtcga tgcaccctgt tcataggagc    5160
ctcttcctac cactccgacc cctgcgggtc cgatcacccg cggtgtacct ggagactcga    5220
cctattttct ctcacaagag atcaaagcct aagcccccca tgtccagact tagttactta    5280
ctcacagtat cataggccct actccctgta tgtattcccc cattggataa ccaaacctaa    5340
ccgtcgaggc ctaggttact attctgcttc ctactcagac cctgcgcta tacaatgccc     5400 ttacttagga tgccagtcat ggacatgtcc ttatacaggc ccggtgtcca gcccacattg    5460
gaaatactcc tccgatctta atttacccca agaagtatca tccatctccc tacacttgca    5520
cttttccaaa tgtgggtcct cattctcctt tctactagac gcaccaggat atgatccagt    5580
gtggttcctc tcctcccagg ccacacaggc cccacccacg cctgcccctc tcataCagga   5640
ctcagatctc caacatatcc tagaaccttc catcccctgg agctccaaaa tcctcaatct    5700
catcctcctt accctaaaaa gctctaatta ttcttgcatg gtctgtgttg accgctccag    5760
cctatcttcg tggcatgttc tatatgaccc acttaaagcc cccaatccac ccgaccccaa    5820
agcccagtct attctgcgac cctccctagc cattcccgcc agtaatgtca ccccgccatt    5880
tccttggacc cattgctatc gcccccttct acaggccatc tcctcggaac actgcaataa    5940
ctccgtagta ctgccccccct tttccctgtc cccacttcct aacgtctcca gaccccgaaa    6000
gcgccgagca gtccccattg ccatatggct agtgtccgcc ctagcggccg gcaccggtat    6060
agctggcgga gttaccggct ccctgtctct ggcctccagt aaaagcctac tgcgcgaagt    6120
agaccaggat atagatcacc tgacgcaggc gattgtaaaa aaccatgata atatccttcg    6180
ggttgctcaa tacgcagccc aaaatcgccg tggcctagat ttactttttct gggaacaagg    6240 gggcctttgt aaggccatcc aagaacaatg ttgcttcctt aatatcagca cacccatgt    6300 gtccgtcctc caggaaagac cccccctaga aaagagagta atcactggct ggggactcaa    6360
ctgggacctc gggctctccc aatgggcccg agaggccctt cagacaggta taacactttt    6420
agcccttttt ctcctcctca tcgttgtagg accctgcgtc atacgccagc tacaggccct    6480
cccttcccgt ctgcagcatc gcagtcagcc ctactccctt tcaattatg aaaccaactt    6540 ataacagatc tgctacctcc tgtagcagga ggctatggct ctcgcctcta ctagacaccc    6600
aagtacagca taatcctgaa gaatcccctt cgatgtcgac gccctggccc caacagtcca    6660
tataccaaaa gtattcctct aaagattcct cgcagcctgc gcgtagctgc tggctctccc    6720
gctccaaaaa gtctatatag ccctctagta agtcacaaaa cccctcgaac cccaacatgt    6780
ctatacagtc cagttgctgt cgcctttcct ttttctgcct cttcctctcc tccagctctt    6840
cgcggcacct tctccgacgc tcttcctttt tttttcgttc tcgccaataa ctcagcagtt    6900
```

-continued

```
gctcctgctc ctgagcaagg tcatccagcc gactcttcca ataacccagg tccttactgc     6960
tagatcctaa gggccgtccc cggggtcgtt tgccattccc ctgaagcatg tccatttgat     7020
ccctacctga tctctcacat aagtttaaca aagtttccac aggtgtaaga ggctcctctg     7080
cagtcaacac cggcggtccc agactccgag atcgggaagt caaactgcct ccagaagtag     7140
aaatgcagga atataccaca ggcacagttc ctgggattgc agtctccggg gctaggacag     7200
gcatctgcct aaagtaacct acaaaagttt tattcccttg tcagcccatt tcccaggttt     7260
cggacagagc cttctctacg ggtaccctgt ctacgttttc ggcgactgtg tacaggccga     7320
ttggtgcccc atttctgggg ggctttgttc cgctcggcta caccgccatg ccctactggc     7380
cacgtgcccc gaacatcaga ttacctggga ccccatcgat ggacgcgttg tcagctcagc     7440
tctacaatac cttatccctc gactcccctc cttccccacc cagagaacta cccgcaccct     7500
caaggttctc acccccccaa ccactgctgc gacccccaag attcctccat ccttcttcca     7560
cgccgttaaa aaacacaccc ccttccgaaa caattgcctt gaactcaccc tgggagagca     7620
gttgccagcc atgtccttcc ccgaccctgg gctccgaccc caaaacatct acaccatgtg     7680
gggaagctcc gttgtgtgcc tttacctcta tcagctctcc ccccccatga cctggcctct     7740
aatcccgcat gttatattct gccatcctga gcagcttgga gccttcctca cccgagtccc     7800
taccaaacga ttagaagaac tcctgtataa gatatttta agcacagggg cgataatcat     7860
cctgcctgaa aactgttttc caaccaccct gttccaaccc accgcgcgc ccgcggtgca     7920 ggcccctgg cacacaggcc tgctcccgtg tcaaaggaa attgctaccc ccgggctcat     7980
ttggactttc actgatggca gccccatgat ttccggccct tgccccaaag aaggacagcc     8040
atctttagta gtacaatcat ctacatttat cttcaacaa ttccaaacca aggccagtca     8100
ccccgctttc ctcttgtccc acaaactaat ccactactcc tcttttcatt ccctccacct     8160
cctctttgag gaatatacaa ctatcccctt ttctctactt tttaatgaaa aagggcaaa     8220 tgtcgatgat gatgagcccc gagacgggtc acaaccacca gctagaggac aaatagctga     8280
gtcacccgtc tgagaaccgt ctcacaccgg gattgtgccc aaaaagaaca ccggggctct     8340
gacgtctctc cctaccctgg ctcccggaaa aaaccaaaaa ccacccattt cctcatgttt     8400
gcctaaagct ctgacgataa ccctaaaaaa tttgactagc aaataaagaa ccctgggccc     8460
tataaagggg gagagcaacc taaaaatggg atccctttc tgcacctcgc caaccccctcc     8520 tctggccacg gtccgacttt ggtcattcct gcctacctga atcgccgctt cgggatcgag     8580
ccatccctct tctatttggt ggcacttcgc gcactccgcc gccttccact cggtaagatc     8640
ccactgggtc gagctaggcc atcacccctg gccgctccc ctggagctct ctcgcgcggc     8700
tcttaaggtt gctccccctc agcaagggc ccagggcttt ctctacttcc ttgtttcaag     8760
tctctttctt tggcggtcga cctaaatcga aagtagcact tctgctgtca gcagcgaggc     8820
ttggcccagg gccagcgcct gtaaggttac ccagctcgga gttgggtctc tagagaatca     8880
gggctaaagc tgctagccct aggaaagaag gcaaaca                            8917
```

<210> SEQ ID NO 37
<211> LENGTH: 491
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 37

Met Gly Lys Phe Cys Leu Tyr Phe Cys Leu Ile Tyr Ile Leu Phe Ser

```
            1               5                  10                 15
Ala Ser Ser Gly Asn Pro Ser Arg Cys Thr Leu Phe Ile Gly Ala Ser
                20                  25                 30

Ser Tyr His Ser Asp Pro Cys Gly Ser Asp His Pro Arg Cys Thr Trp
                35                  40                 45

Arg Leu Asp Leu Phe Ser Leu Thr Arg Asp Gln Ser Leu Ser Pro Pro
        50                  55                 60

Cys Pro Asp Leu Val Thr Tyr Ser Gln Tyr His Arg Pro Tyr Ser Leu
 65                 70                  75                     80

Tyr Val Phe Pro His Trp Ile Thr Lys Pro Asn Arg Arg Gly Leu Gly
                85                  90                 95

Tyr Tyr Ser Ala Ser Tyr Ser Asp Pro Cys Ala Ile Gln Cys Pro Tyr
                100                 105                110

Leu Gly Cys Gln Ser Trp Thr Cys Pro Tyr Thr Gly Pro Val Ser Ser
            115                 120                125

Pro His Trp Lys Tyr Ser Ser Asp Leu Asn Phe Thr Gln Glu Val Ser
            130                 135                 140

Ser Ile Ser Leu His Leu His Phe Ser Lys Cys Gly Ser Ser Phe Ser
145                 150                 155                 160

Phe Leu Leu Asp Ala Pro Gly Tyr Asp Pro Val Trp Phe Leu Ser Ser
                165                 170                 175

Gln Ala Thr Gln Ala Pro Thr Pro Ala Pro Leu Ile Gln Asp Ser
                180                 185                 190

Asp Leu Gln His Ile Leu Glu Pro Ser Ile Pro Trp Ser Ser Lys Ile
                195                 200                 205

Leu Asn Leu Ile Leu Leu Thr Leu Lys Ser Ser Asn Tyr Ser Cys Met
    210                 215                 220

Val Cys Val Asp Arg Ser Leu Ser Ser Trp His Val Leu Tyr Asp
225                 230                 235                 240

Pro Leu Lys Ala Pro Asn Pro Asp Pro Lys Ala Gln Ser Ile Leu
                245                 250                 255

Arg Pro Ser Leu Ala Ile Pro Ala Ser Asn Val Thr Pro Pro Phe Pro
            260                 265                 270

Trp Thr His Cys Tyr Arg Pro Leu Leu Gln Ala Ile Ser Ser Glu His
        275                 280                 285

Cys Asn Asn Ser Val Val Leu Pro Pro Phe Ser Leu Ser Pro Leu Pro
    290                 295                 300

Asn Val Ser Arg Pro Arg Lys Arg Arg Ala Val Pro Ile Ala Ile Trp
305                 310                 315                 320

Leu Val Ser Ala Leu Ala Ala Gly Thr Gly Ile Ala Gly Val Thr
                325                 330                 335

Gly Ser Leu Ser Leu Ala Ser Ser Lys Ser Leu Leu Arg Glu Val Asp
            340                 345                 350

Gln Asp Ile Asp His Leu Thr Gln Ala Ile Val Lys Asn His Asp Asn
            355                 360                 365

Ile Leu Arg Val Ala Gln Tyr Ala Ala Gln Asn Arg Arg Gly Leu Asp
    370                 375                 380

Leu Leu Phe Trp Glu Gln Gly Gly Leu Cys Lys Ala Ile Gln Glu Gln
385                 390                 395                 400

Cys Cys Phe Leu Asn Ile Ser Asn Thr His Val Ser Val Leu Gln Glu
                405                 410                 415

Arg Pro Pro Leu Glu Lys Arg Val Ile Thr Gly Trp Gly Leu Asn Trp
            420                 425                 430
```

```
Asp Leu Gly Leu Ser Gln Trp Ala Arg Glu Ala Leu Gln Thr Gly Ile
        435                 440                 445

Thr Leu Leu Ala Leu Phe Leu Leu Ile Val Val Gly Pro Cys Val
    450                 455                 460

Ile Arg Gln Leu Gln Ala Leu Pro Ser Arg Leu Gln His Arg Ser Gln
465                 470                 475                 480

Pro Tyr Ser Leu Leu Asn Tyr Glu Thr Asn Leu
                485                 490

<210> SEQ ID NO 38
<211> LENGTH: 315
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 38

Met Gly Lys Phe Cys Leu Tyr Phe Cys Leu Ile Tyr Ile Leu Phe Ser
1               5                   10                  15

Ala Ser Ser Gly Asn Pro Ser Arg Cys Thr Leu Phe Ile Gly Ala Ser
                20                  25                  30

Ser Tyr His Ser Asp Pro Cys Gly Ser Asp His Pro Arg Cys Thr Trp
            35                  40                  45

Arg Leu Asp Leu Phe Ser Leu Thr Arg Asp Gln Ser Leu Ser Pro Pro
    50                  55                  60

Cys Pro Asp Leu Val Thr Tyr Ser Gln Tyr His Arg Pro Tyr Ser Leu
65                  70                  75                  80

Tyr Val Phe Pro His Trp Ile Thr Lys Pro Asn Arg Arg Gly Leu Gly
                85                  90                  95

Tyr Tyr Ser Ala Ser Tyr Ser Asp Pro Cys Ala Ile Gln Cys Pro Tyr
                100                 105                 110

Leu Gly Cys Gln Ser Trp Thr Cys Pro Tyr Thr Gly Pro Val Ser Ser
            115                 120                 125

Pro His Trp Lys Tyr Ser Ser Asp Leu Asn Phe Thr Gln Glu Val Ser
    130                 135                 140

Ser Ile Ser Leu His Leu His Phe Ser Lys Cys Gly Ser Ser Phe Ser
145                 150                 155                 160

Phe Leu Leu Asp Ala Pro Gly Tyr Asp Pro Val Trp Phe Leu Ser Ser
                165                 170                 175

Gln Ala Thr Gln Ala Pro Pro Thr Pro Ala Pro Leu Ile Gln Asp Ser
            180                 185                 190

Asp Leu Gln His Ile Leu Glu Pro Ser Ile Pro Trp Ser Ser Lys Ile
    195                 200                 205

Leu Asn Leu Ile Leu Leu Thr Leu Lys Ser Ser Asn Tyr Ser Cys Met
210                 215                 220

Val Cys Val Asp Arg Ser Ser Leu Ser Ser Trp His Val Leu Tyr Asp
225                 230                 235                 240

Pro Leu Lys Ala Pro Asn Pro Pro Asp Pro Lys Ala Gln Ser Ile Leu
                245                 250                 255

Arg Pro Ser Leu Ala Ile Pro Ala Ser Asn Val Thr Pro Pro Phe Pro
            260                 265                 270

Trp Thr His Cys Tyr Arg Pro Leu Leu Gln Ala Ile Ser Ser Glu His
    275                 280                 285

Cys Asn Asn Ser Val Val Leu Pro Pro Phe Ser Leu Ser Pro Leu Pro
290                 295                 300
```

```
Asn Val Ser Arg Pro Arg Lys Arg Ala Val
305                 310                 315
```

```
<210> SEQ ID NO 39
<211> LENGTH: 176
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 39

Pro Ile Ala Ile Trp Leu Val Ser Ala Leu Ala Ala Gly Thr Gly Ile
  1               5                  10                  15

Ala Gly Gly Val Thr Gly Ser Leu Ser Leu Ala Ser Ser Lys Ser Leu
                 20                  25                  30

Leu Arg Glu Val Asp Gln Asp Ile Asp His Leu Thr Gln Ala Ile Val
             35                  40                  45

Lys Asn His Asp Asn Ile Leu Arg Val Ala Gln Tyr Ala Ala Gln Asn
 50                  55                  60

Arg Arg Gly Leu Asp Leu Leu Phe Trp Glu Gln Gly Gly Leu Cys Lys
 65                  70                  75                  80

Ala Ile Gln Glu Gln Cys Cys Phe Leu Asn Ile Ser Asn Thr His Val
                 85                  90                  95

Ser Val Leu Gln Glu Arg Pro Pro Leu Glu Lys Arg Val Ile Thr Gly
                100                 105                 110

Trp Gly Leu Asn Trp Asp Leu Gly Leu Ser Gln Trp Ala Arg Glu Ala
                115                 120                 125

Leu Gln Thr Gly Ile Thr Leu Leu Ala Leu Phe Leu Leu Leu Ile Val
            130                 135                 140

Val Gly Pro Cys Val Ile Arg Gln Leu Gln Ala Leu Pro Ser Arg Leu
145                 150                 155                 160

Gln His Arg Ser Gln Pro Tyr Ser Leu Leu Asn Tyr Glu Thr Asn Leu
                165                 170                 175
```

```
<210> SEQ ID NO 40
<211> LENGTH: 422
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 40

Met Gly Lys Thr Tyr Ser Ser Pro Ile Asn Pro Ile Pro Lys Ala Pro
  1               5                  10                  15

Lys Gly Leu Ala Ile His His Trp Leu Asn Phe Leu Gln Ala Ala Tyr
                 20                  25                  30

Arg Leu Gln Pro Gly Pro Ser Glu Phe Asp Phe His Gln Leu Arg Lys
             35                  40                  45

Phe Leu Lys Leu Ala Ile Lys Thr Pro Val Trp Leu Asn Pro Ile Asn
 50                  55                  60

Tyr Ser Val Leu Ala Gly Leu Ile Pro Lys Asn Tyr Pro Gly Arg Val
 65                  70                  75                  80

His Glu Ile Val Ala Ile Leu Ile Gln Glu Thr Pro Ala Arg Glu Ala
                 85                  90                  95

Pro Pro Ser Ala Pro Leu Ala Glu Asp Pro Gln Lys Pro Pro Pro Tyr
                100                 105                 110

Pro Glu Gln Ala Gln Glu Ala Ser Gln Cys Leu Pro Ile Leu His Pro
```

115                 120                 125
His Gly Ala Pro Ala Ala His Arg Pro Trp Gln Met Lys Asp Leu Gln
    130                 135                 140

Ala Ile Lys Gln Glu Val Ser Ser Ala Pro Gly Ser Pro Gln Phe
145                 150                 155                 160

Met Gln Thr Ile Arg Leu Ala Val Gln Gln Phe Asp Pro Thr Ala Lys
                    165                 170                 175

Asp Leu His Asp Leu Leu Gln Tyr Leu Cys Ser Ser Leu Val Ala Ser
                180                 185                 190

Leu His His Gln Gln Leu Glu Thr Leu Ile Ala Gln Ala Glu Thr Gln
            195                 200                 205

Gly Ile Thr Gly Tyr Asn Pro Leu Ala Gly Pro Leu Arg Ile Gln Ala
        210                 215                 220

Asn Asn Pro Asn Gln Gln Gly Leu Arg Lys Glu Tyr Gln Asn Leu Trp
225                 230                 235                 240

Leu Ser Ala Phe Ser Ala Leu Pro Gly Asn Thr Lys Asp Pro Thr Trp
                    245                 250                 255

Ala Ala Ile Leu Gln Gly Pro Glu Pro Phe Gly Ser Phe Val Glu
                260                 265                 270

Arg Leu Asn Val Ala Leu Asp Asn Gly Leu Pro Glu Gly Thr Pro Lys
            275                 280                 285

Asp Pro Ile Leu Arg Ser Leu Ala Tyr Ser Asn Ala Asn Lys Glu Cys
        290                 295                 300

Gln Lys Leu Leu Gln Ala Arg Gly Gln Thr Asn Ser Pro Leu Gly Glu
305                 310                 315                 320

Met Leu Arg Ala Cys Gln Thr Trp Thr Pro Arg Asp Lys Asn Lys Ile
                    325                 330                 335

Leu Met Val Gln Pro Lys Lys Thr Pro Pro Asn Gln Pro Cys Phe
                340                 345                 350

Arg Cys Gly Gln Val Gly His Trp Ser Arg Asp Cys Lys Gln Pro Arg
            355                 360                 365

Pro Pro Pro Gly Pro Cys Pro Val Cys Gln Asp Pro Thr His Trp Lys
        370                 375                 380

Arg Asp Cys Pro Gln Leu Lys Thr Asp Thr Arg Asp Ser Glu Asp Leu
385                 390                 395                 400

Leu Leu Asp Leu Pro Cys Glu Ala Pro Asn Val Arg Glu Arg Lys Asn
                    405                 410                 415

Ser Ser Gly Gly Glu Asp
                420

<210> SEQ ID NO 41
<211> LENGTH: 86
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 41

Leu Met Val Gln Pro Lys Lys Thr Pro Pro Asn Gln Pro Cys Phe
1               5                   10                  15

Arg Cys Gly Gln Val Gly His Trp Ser Arg Asp Cys Lys Gln Pro Arg
            20                  25                  30

Pro Pro Pro Gly Pro Cys Pro Val Cys Gln Asp Pro Thr His Trp Lys
        35                  40                  45

Arg Asp Cys Pro Gln Leu Lys Thr Asp Thr Arg Asp Ser Glu Asp Leu

```
                    50                  55                  60
Leu Leu Asp Leu Pro Cys Glu Ala Pro Asn Val Arg Glu Arg Lys Asn
 65                  70                  75                  80

Ser Ser Gly Gly Glu Asp
                 85

<210> SEQ ID NO 42
<211> LENGTH: 123
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 42

Met Gly Lys Thr Tyr Ser Ser Pro Ile Asn Pro Ile Pro Lys Ala Pro
  1               5                  10                  15

Lys Gly Leu Ala Ile His His Trp Leu Asn Phe Leu Gln Ala Ala Tyr
                 20                  25                  30

Arg Leu Gln Pro Gly Pro Ser Glu Phe Asp Phe His Gln Leu Arg Lys
             35                  40                  45

Phe Leu Lys Leu Ala Ile Lys Thr Pro Val Trp Leu Asn Pro Ile Asn
 50                  55                  60

Tyr Ser Val Leu Ala Gly Leu Ile Pro Lys Asn Tyr Pro Gly Arg Val
 65                  70                  75                  80

His Glu Ile Val Ala Ile Leu Ile Gln Glu Thr Pro Ala Arg Glu Ala
                 85                  90                  95

Pro Pro Ser Ala Pro Leu Ala Glu Asp Pro Gln Lys Pro Pro Pro Tyr
            100                 105                 110

Pro Glu Gln Ala Gln Glu Ala Ser Gln Cys Leu
            115                 120

<210> SEQ ID NO 43
<211> LENGTH: 213
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 43

Pro Ile Leu His Pro His Gly Ala Pro Ala Ala His Arg Pro Trp Gln
  1               5                  10                  15

Met Lys Asp Leu Gln Ala Ile Lys Gln Glu Val Ser Ser Ser Ala Pro
                 20                  25                  30

Gly Ser Pro Gln Phe Met Gln Thr Ile Arg Leu Ala Val Gln Gln Phe
             35                  40                  45

Asp Pro Thr Ala Lys Asp Leu His Asp Leu Leu Gln Tyr Leu Cys Ser
 50                  55                  60

Ser Leu Val Ala Ser Leu His His Gln Gln Leu Glu Thr Leu Ile Ala
 65                  70                  75                  80

Gln Ala Glu Thr Gln Gly Ile Thr Gly Tyr Asn Pro Leu Ala Gly Pro
                 85                  90                  95

Leu Arg Ile Gln Ala Asn Asn Pro Asn Gln Gln Gly Leu Arg Lys Glu
            100                 105                 110

Tyr Gln Asn Leu Trp Leu Ser Ala Phe Ser Ala Leu Pro Gly Asn Thr
            115                 120                 125

Lys Asp Pro Thr Trp Ala Ala Ile Leu Gln Gly Pro Glu Glu Pro Phe
            130                 135                 140
```

```
Gly Ser Phe Val Glu Arg Leu Asn Val Ala Leu Asp Asn Gly Leu Pro
145                 150                 155                 160

Glu Gly Thr Pro Lys Asp Pro Ile Leu Arg Ser Leu Ala Tyr Ser Asn
                165                 170                 175

Ala Asn Lys Glu Cys Gln Lys Leu Leu Gln Ala Arg Gly Gln Thr Asn
            180                 185                 190

Ser Pro Leu Gly Glu Met Leu Arg Ala Cys Gln Thr Trp Thr Pro Arg
        195                 200                 205

Asp Lys Asn Lys Ile
        210

<210> SEQ ID NO 44
<211> LENGTH: 889
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 44

Gly Pro Pro Cys Pro Ser Thr Gln Ala Tyr Arg Ile Arg Ala Pro Ser
1               5                   10                  15

Pro Ala Pro Arg Ser Leu Ser Val Pro Val Lys Pro Glu Arg Leu Gln
            20                  25                  30

Ala Leu Thr Asp Leu Val Ser Arg Ala Leu Glu Ala Lys His Ile Glu
        35                  40                  45

Pro Tyr Gln Gly Pro Gly Asn Asn Pro Ile Phe Pro Val Lys Lys Pro
    50                  55                  60

Asn Gly Lys Trp Arg Phe Ile His Asp Leu Arg Ala Thr Asn Ser Val
65                  70                  75                  80

Thr Arg Asp Leu Ala Ser Pro Ser Pro Gly Pro Pro Asp Leu Thr Ser
                85                  90                  95

Leu Pro Gln Gly Leu Pro His Leu Arg Thr Ile Asp Leu Thr Asp Ala
            100                 105                 110

Phe Phe Gln Ile Pro Leu Pro Thr Ile Phe Gln Pro Tyr Phe Ala Phe
        115                 120                 125

Thr Leu Pro Gln Pro Asn Asn Tyr Gly Pro Gly Thr Arg Tyr Ser Trp
    130                 135                 140

Arg Val Leu Pro Gln Gly Phe Lys Asn Ser Pro Thr Leu Phe Glu Gln
145                 150                 155                 160

Gln Leu Ser His Ile Leu Thr Pro Val Arg Lys Thr Phe Pro Asn Ser
                165                 170                 175

Leu Ile Ile Gln Tyr Met Asp Asp Ile Leu Leu Ala Ser Pro Ala Pro
            180                 185                 190

Gly Glu Leu Ala Ala Leu Thr Asp Lys Val Thr Asn Ala Leu Thr Lys
        195                 200                 205

Glu Gly Leu Pro Leu Ser Pro Glu Lys Thr Gln Ala Thr Pro Gly Pro
    210                 215                 220

Ile His Phe Leu Gly Gln Val Ile Ser Gln Asp Cys Ile Thr Tyr Glu
225                 230                 235                 240

Thr Leu Pro Ser Ile Asn Val Lys Ser Thr Trp Ser Leu Ala Glu Leu
                245                 250                 255

Gln Ser Met Leu Gly Glu Leu Gln Trp Val Ser Lys Gly Thr Pro Val
            260                 265                 270

Leu Arg Ser Ser Leu His Gln Leu Tyr Leu Ala Leu Arg Gly His Arg
        275                 280                 285
```

```
Asp Pro Arg Asp Thr Ile Lys Leu Thr Ser Ile Gln Val Gln Ala Leu
    290                 295                 300

Arg Thr Ile Gln Lys Ala Leu Thr Leu Asn Cys Arg Ser Arg Leu Val
305                 310                 315                 320

Asn Gln Leu Pro Ile Leu Ala Leu Ile Met Leu Arg Pro Thr Gly Thr
                325                 330                 335

Thr Ala Val Leu Phe Gln Thr Lys Gln Lys Trp Pro Leu Val Trp Leu
            340                 345                 350

His Thr Pro His Pro Ala Thr Ser Leu Arg Pro Trp Gly Gln Leu Leu
        355                 360                 365

Ala Asn Ala Val Ile Ile Leu Asp Lys Tyr Ser Leu Gln His Tyr Gly
    370                 375                 380

Gln Val Cys Lys Ser Phe His His Asn Ile Ser Asn Gln Ala Leu Thr
385                 390                 395                 400

Tyr Tyr Leu His Thr Ser Asp Gln Ser Ser Val Ala Ile Leu Leu Gln
                405                 410                 415

His Ser His Arg Phe His Asn Leu Gly Ala Gln Pro Ser Gly Pro Trp
            420                 425                 430

Arg Ser Leu Leu Gln Met Pro Gln Ile Phe Gln Asn Ile Asp Val Leu
        435                 440                 445

Arg Pro Pro Phe Thr Ile Ser Pro Val Val Ile Asn His Ala Pro Cys
450                 455                 460

Leu Phe Ser Asp Gly Ser Ala Ser Lys Ala Ala Phe Ile Ile Trp Asp
465                 470                 475                 480

Arg Gln Val Ile His Gln Val Leu Ser Leu Pro Ser Thr Cys Ser
                485                 490                 495

Ala Gln Ala Gly Glu Leu Phe Gly Leu Leu Ala Gly Leu Gln Lys Ser
            500                 505                 510

Gln Pro Trp Val Ala Leu Asn Ile Phe Leu Asp Ser Lys Phe Leu Ile
        515                 520                 525

Gly His Leu Arg Arg Met Ala Leu Gly Ala Phe Pro Gly Pro Ser Thr
    530                 535                 540

Gln Cys Glu Leu His Thr Gln Leu Leu Pro Leu Leu Gln Gly Lys Thr
545                 550                 555                 560

Val Tyr Val His His Val Arg Ser His Thr Leu Leu Gln Asp Pro Ile
                565                 570                 575

Ser Arg Leu Asn Glu Ala Thr Asp Ala Leu Met Leu Ala Pro Leu Leu
            580                 585                 590

Pro Leu Asp Pro Thr Thr Leu His Gln Leu Thr His Cys Asn Pro Tyr
        595                 600                 605

Ala Leu Arg Asn His Gly Ala Thr Ala Ser Glu Ala His Ala Ile Val
    610                 615                 620

Gln Ala Cys His Thr Cys Lys Val Ile Asn Pro Gln Gly Arg Leu Pro
625                 630                 635                 640

Gln Gly Tyr Ile Arg Arg Gly His Ala Pro Asn Asp Ile Trp Gln Gly
                645                 650                 655

Asp Val Thr His Leu Gln Tyr Lys Arg Tyr Lys Tyr Cys Leu Leu Val
            660                 665                 670

Trp Val Asp Thr Tyr Ser Gly Ala Val Ser Val Ser Cys Arg Arg Lys
        675                 680                 685

Glu Thr Gly Ser Asp Cys Val Ala Ser Leu Leu Val Ala Ile Ser Ile
    690                 695                 700

Leu Gly Lys Pro Gln Asn Ile Asn Thr Asp Asn Gly Ala Ala Tyr Leu
```

| | | | | | | | | | | | | | | |
|---|---|---|---|---|---|---|---|---|---|---|---|---|---|---|
| | | 705 | | | | 710 | | | | 715 | | | | 720 |
| Ser | Gln | Glu | Phe | Gln | Gln | Phe | Cys | Asn | Ser | Leu | Ala | Ile | Lys | His | Ser |
| | | | | 725 | | | | | 730 | | | | | 735 |
| Thr | His | Ile | Pro | Tyr | Asn | Pro | Thr | Ser | Ser | Gly | Leu | Val | Glu | Arg | Thr |
| | | | 740 | | | | | 745 | | | | | 750 | |
| Asn | Gly | Ile | Leu | Lys | Thr | Leu | Ile | Ser | Lys | Tyr | Leu | Leu | Asp | Asn | His |
| | | | 755 | | | | | 760 | | | | | 765 | |
| His | Leu | Pro | Leu | Glu | Thr | Ala | Val | Ser | Lys | Ser | Leu | Trp | Thr | Ile | Asn |
| | | 770 | | | | | 775 | | | | | 780 | | |
| His | Leu | Asn | Val | Leu | Pro | Ser | Cys | Gln | Lys | Thr | Arg | Trp | Gln | Leu | His |
| 785 | | | | | 790 | | | | | 795 | | | | | 800 |
| Gln | Ala | Gln | Pro | Leu | Pro | Pro | Val | Pro | Glu | Asp | Thr | Leu | Pro | Pro | His |
| | | | | 805 | | | | | 810 | | | | | 815 | |
| Thr | Ser | Pro | Lys | Trp | Tyr | Tyr | Lys | Ile | Pro | Gly | Leu | Thr | Asn | Ser | |
| | | | 820 | | | | | 825 | | | | | 830 | | |
| Arg | Trp | Ser | Gly | Pro | Val | Gln | Ser | Leu | Lys | Glu | Ala | Ala | Gly | Ala | Ala |
| | | | 835 | | | | | 840 | | | | | 845 | | |
| Leu | Ile | Pro | Val | Gly | Gly | Ser | Tyr | Leu | Trp | Ile | Pro | Trp | Arg | Leu | Leu |
| | | 850 | | | | | 855 | | | | | 860 | | | |
| Lys | Arg | Gly | Ile | Cys | Pro | Arg | Pro | Glu | Ser | Ser | Ala | Ala | Val | Asp | Pro |
| 865 | | | | | 870 | | | | | 875 | | | | | 880 |
| Lys | Thr | Arg | Asp | His | Gln | Leu | His | Gly | | | | | | | |
| | | | | 885 | | | | | | | | | | | |

<210> SEQ ID NO 45
<211> LENGTH: 697
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 45

```
tgtcgatgat gatgagcccc gagacgggtc acaaccacca gctagaggac aaatagctga      60
gtcacccgtc tgagaaccgt ctcacaccgg gattgtgccc aaaagaaca ccggggctct     120
gacgtctctc cctaccctgg ctcccggaaa aaccaaaaa ccacccattt cctcatgttt     180
gcctaaagct ctgacgataa ccctaaaaaa tttgactagc aaataagaa ccctgggccc     240
tataaaaggg gagagcaacc taaaaatggg atcccttttc tgcacctcgc caaccctcc    300
tctggccacg gtccgacttt ggtcattcct gcctacctga atcgccgctt cgggatcgag     360
ccatccctct tctatttggt ggcacttcgc gcactccgcc gccttccact cggtaagatc     420
ccactgggtc gagctaggcc atcaccctg ggccgctccc ctggagctct ctcgcgcggc     480
tcttaaggtt gctccccctc agcaagggc ccagggcttt ctctacttcc ttgtttcaag     540
tctctttctt tggcggtcga cctaaatcga aagtagcact tctgctgtca gcagcgaggc     600
ttggcccagg gccagcgcct gtaaggttac ccagctcgga gttgggtctc tagagaatca     660
gggctaaagc tgctagccct aggaaagaag gcaaaca                             697
```

<210> SEQ ID NO 46
<211> LENGTH: 177
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 46

```
Ser Thr Gln Cys Pro Gly Thr Lys Lys Leu Leu Arg Gly Gly Leu
1               5                   10                  15

Ala Ser Pro Arg Thr Ile Leu Pro Leu Ile Pro Leu Ser Gln Gln Lys
            20                  25                  30

Gln Pro Thr Leu His Ile Gln Val Ser Phe Ser Asn Thr Pro Pro Val
            35                  40                  45

Ser Val Gln Ala Leu Leu Asp Thr Gly Ala Asp Ile Thr Val Leu Pro
50                  55                  60

Ala Cys Leu Cys Pro Pro Asp Ser Asn Leu Gln Asp Thr Thr Val Leu
65                  70                  75                  80

Gly Ala Gly Gly Pro Ser Thr Asn Lys Phe Lys Ile Leu Pro Cys Pro
                85                  90                  95

Val His Ile His Leu Pro Phe Arg Arg Gln Pro Val Thr Leu Thr Ala
                100                 105                 110

Cys Leu Ile Asp Ile Asn Asn Gln Trp Thr Ile Leu Gly Arg Asp Ala
            115                 120                 125

Leu Gln Gln Cys Gln Ser Ser Leu Tyr Leu Ala Asp Gln Pro Ser Lys
130                 135                 140

Val Leu Pro Val Leu Ala Pro Lys Leu Ile Gly Leu Glu His Leu Pro
145                 150                 155                 160

Pro Pro Pro Glu Val Ser Gln Phe Pro Leu Asn Gln Ser Ala Ser Arg
                165                 170                 175

Leu

<210> SEQ ID NO 47
<211> LENGTH: 534
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 47
agcacccaat gtccgggaac gaaaaaactc ctcagggggg gaggattagc ctcccccga     60 accatactcc ccccttatacc tttgtcccag cagaagcagc ctaccctgca tatccaggta   120 tcgtttttcca acaccccccc tgttagcgtt caggcgctcc tcgacactgg agcagacatc  180
actgtcctcc cggcctgctt atgccctccc gattccaacc tccaggacac cactgtccta   240
ggtgcaggcg ggccaagtac caacaagttt aaaatcctgc cctgtccagt ccatatccac    300
ttgccttttc gaaggcagcc ggtgacccta accgcttgcc taattgatat taacaaccag  360
tggaccatat tagggcgaga tgccctacaa caatgtcaaa gttccctcta tctggctgac  420
caaccctcta aggtcctccc tgtcctagca cccaagctta tcggattaga gcaccttccc  480
ccgcccccag aagtctctca gttcccgtta aaccagagcg cctccaggct ctga           534

<210> SEQ ID NO 48
<211> LENGTH: 182
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 48

Met Pro Lys Thr Arg Lys Gln Arg Ser Arg Pro Lys Asn Gln Arg
1               5                   10                  15

Pro Ser Thr Pro Trp Pro Ile Ser Gln Val Ser Asp Arg Ala Phe Ser
```

```
                    20                  25                  30

Thr Gly Thr Leu Ser Thr Phe Ser Ala Thr Val Tyr Arg Pro Ile Gly
            35                  40                  45

Ala Pro Phe Leu Gly Gly Phe Val Pro Leu Gly Tyr Thr Ala Met Pro
        50                  55                  60

Tyr Trp Pro Arg Ala Pro Asn Ile Arg Leu Pro Gly Thr Pro Ser Met
65                  70                  75                  80

Asp Ala Leu Ser Ala Gln Leu Tyr Asn Thr Leu Ser Leu Asp Ser Pro
                85                  90                  95

Pro Ser Pro Pro Arg Glu Leu Pro Ala Pro Ser Arg Phe Ser Pro Pro
            100                 105                 110

Gln Pro Leu Leu Arg Pro Pro Arg Phe Leu His Pro Ser Ser Thr Pro
        115                 120                 125

Leu Lys Asn Thr Pro Pro Ser Glu Thr Ile Ala Leu Asn Ser Pro Trp
    130                 135                 140

Glu Ser Ser Cys Gln Pro Cys Pro Ser Pro Thr Leu Gly Ser Asp Pro
145                 150                 155                 160

Lys Thr Ser Thr Pro Cys Gly Glu Ala Pro Leu Cys Ala Phe Thr Ser
                165                 170                 175

Ile Ser Ser Pro Pro Pro
            180

<210> SEQ ID NO 49
<211> LENGTH: 549
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 49
atgcccaaga cccgaaagca gcgcagccgt cgacccaaaa accagagacc atcaactcca      60
tggcccattt cccaggtttc ggacagagcc ttctctacgg gtaccctgtc tacgttttcg     120
gcgactgtgt acaggccgat tggtgcccca tttctggggg ctttgttcc gctcggctac     180 accgccatgc cctactggcc acgtgccccg aacatcagat tacctgggac cccatcgatg     240
gacgcgttgt cagctcagct ctacaatacc ttatccctcg actcccctcc ttccccaccc     300
agagaactac ccgcaccctc aaggttctca ccccccaac cactgctgcg accccaaga      360 ttcctccatc cttcttccac gccgttaaaa aacacacccc cttccgaaac aattgccttg     420
aactcaccct gggagagcag ttgccagcca tgtccttccc cgaccctggg ctccgacccc     480
aaaacatcta ccaccatgtgg ggaagctccg ttgtgtgcct ttacctctat cagctctccc     540
cccccatga                                                            549

<210> SEQ ID NO 50
<211> LENGTH: 350
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 50

Met Ala His Phe Pro Gly Phe Gly Gln Ser Leu Leu Tyr Gly Tyr Pro
1               5                   10                  15

Val Tyr Val Phe Gly Asp Cys Val Gln Ala Asp Trp Cys Pro Ile Ser
            20                  25                  30
```

-continued

Gly Gly Leu Cys Ser Ala Arg Leu His Arg His Ala Leu Leu Ala Thr
             35                  40                  45
Cys Pro Glu His Gln Ile Thr Trp Asp Pro Ile Asp Gly Arg Val Val
 50                  55                  60
Ser Ser Ala Leu Gln Tyr Leu Ile Pro Arg Leu Pro Ser Phe Pro Thr
 65                  70                  75                  80
Gln Arg Thr Thr Arg Thr Leu Lys Val Leu Thr Pro Thr Thr Ala
                 85                  90                  95
Ala Thr Pro Lys Ile Pro Pro Ser Phe Phe His Ala Val Lys Lys His
                100                 105                 110
Thr Pro Phe Arg Asn Asn Cys Leu Glu Leu Thr Leu Gly Glu Gln Leu
            115                 120                 125
Pro Ala Met Ser Phe Pro Asp Pro Gly Leu Arg Pro Gln Asn Ile Tyr
130                 135                 140
Thr Met Trp Gly Ser Ser Val Val Cys Leu Tyr Leu Tyr Gln Leu Ser
145                 150                 155                 160
Pro Pro Met Thr Trp Pro Leu Ile Pro His Val Ile Phe Cys His Pro
                165                 170                 175
Glu Gln Leu Gly Ala Phe Leu Thr Arg Val Pro Thr Lys Arg Leu Glu
            180                 185                 190
Glu Leu Leu Tyr Lys Ile Phe Leu Ser Thr Gly Ala Ile Ile Ile Leu
        195                 200                 205
Pro Glu Asn Cys Phe Pro Thr Thr Leu Phe Gln Pro Thr Arg Ala Pro
210                 215                 220
Ala Val Gln Ala Pro Trp His Thr Gly Leu Leu Pro Cys Gln Lys Glu
225                 230                 235                 240
Ile Ala Thr Pro Gly Leu Ile Trp Thr Phe Thr Asp Gly Ser Pro Met
                245                 250                 255
Ile Ser Gly Pro Cys Pro Lys Glu Gly Gln Pro Ser Leu Val Val Gln
            260                 265                 270
Ser Ser Thr Phe Ile Phe Gln Gln Phe Gln Thr Lys Ala Ser His Pro
        275                 280                 285
Ala Phe Leu Leu Ser His Lys Leu Ile His Tyr Ser Ser Phe His Ser
290                 295                 300
Leu His Leu Leu Phe Glu Glu Tyr Thr Thr Ile Pro Phe Ser Leu Leu
305                 310                 315                 320
Phe Asn Glu Lys Gly Ala Asn Val Asp Asp Glu Pro Arg Asp Gly
                325                 330                 335
Ser Gln Pro Pro Ala Arg Gly Gln Ile Ala Glu Ser Pro Val
            340                 345                 350

<210> SEQ ID NO 51
<211> LENGTH: 1053
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 51
atggcccatt tcccaggttt cggacagagc cttctctacg gtaccctgt ctacgttttc      60 ggcgactgtg tacaggccga ttggtgcccc atttctgggg gctttgttc cgctcggcta    120 caccgccatg ccctactggc cacgtgcccc gaacatcaga ttacctggga ccccatcgat    180
ggacgcgttg tcagctcagc tctacaatac cttatccctc gactcccctc cttcccacc    240 cagagaacta cccgcaccct caaggttctc acccccccaa ccactgctgc gacccccaag    300

-continued

```
attcctccat ccttcttcca cgccgttaaa aaacacaccc ccttccgaaa caattgcctt    360
gaactcaccc tgggagagca gttgccagcc atgtccttcc ccgaccctgg gctccgaccc    420
caaaacatct acaccatgtg gggaagctcc gttgtgtgcc tttacctcta tcagctctcc    480
ccccccatga cctggcctct aatcccgcat gttatattct gccatcctga gcagcttgga    540
gccttcctca cccgagtccc taccaaacga ttagaagaac tcctgtataa gatattttta    600
agcacagggg cgataatcat cctgcctgaa aactgttttc caaccaccct gttccaaccc    660
acccgcgcgc ccgcggtgca ggccccctgg cacacaggcc tgctcccgtg tcaaaaggaa    720
attgctaccc ccgggctcat ttggactttc actgatggca gccccatgat ttccggccct    780
tgccccaaag aaggacagcc atctttagta gtacaatcat ctacatttat ctttcaacaa    840
ttccaaacca aggccagtca ccccgctttc ctcttgtccc acaaactaat ccactactcc    900
tcttttcatt ccctccacct cctctttgag gaatatacaa ctatcccctt ttctctactt    960
tttaatgaaa aaggggcaaa tgtcgatgat gatgagcccc gagacgggtc acaaccacca   1020
gctagaggac aaatagctga gtcacccgtc tga                                1053
```

<210> SEQ ID NO 52
<211> LENGTH: 699
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 52

```
cagatctgct acctcctgta gcaggaggct atggctctcg cctctactag acacccaagt     60
acagcataat cctgaagaat cccccttcgat gtcgacgccc tggccccaac agtccatata    120
ccaaaagtat tcctctaaag attcctcgca gcctgcgcgt agctgctggc tctcccgctc    180
caaaaagtct atatagccct ctagtaagtc acaaaacccc tcgaacccca acatgtctat    240
acagtccagt tgctgtcgcc tttccttttt ctgcctcttc ctctcctcca gctcttcgcg    300
gcaccttctc cgacgctctt cctttttttt tcgttctcgc caataactca gcagttgctc    360
ctgctcctga gcaaggtcat ccagccgact cttccaataa cccaggtcct tactgctaga    420
tcctaagggc cgtccccggg gtcgtttgcc attcccctga gcatgtcca tttgatccct    480 acctgatctc tcacataagt ttaacaaagt ttccacaggt gtaagaggct cctctgcagt    540
caacaccggc ggtcccagac tccgagatcg ggaagtcaaa ctgcctccag aagtagaaat    600
gcaggaatat accacaggca cagttcctgg gattgcagtc tccggggcta ggacaggcat    660
ctgcctaaag taacctacaa aagtttttatt cccttgtca                          699
```

<210> SEQ ID NO 53
<211> LENGTH: 5320
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 53

```
ctggccatat cgaaccttac tctgaccag gcaacaaccc agttttccct gttaaaaaac      60
ccaacggcaa gtggcgattt atccatgacc tcagggccac taatgccatc accactaccc    120
ttgcctcgcc ctccccggc cccctgatc ttaccagcct gccacaggcc ttgccccatc     180
ttcagaccat cgatctcacg gacgctttct tccagattcc cctcccaaag cgattccagc    240
```

```
cctacttcgc ctttaccatc ccccagccat taaatcatgg gcctgggagc aggtacgctt      300
ggacagtcct tccccaaggc ttcaaaaaca gccccacgct ctttgagcaa cagctggcca      360
gcgtactagg cccagcccga aaagccttcc ccacatccgt catcgtccaa tacatggacg      420
acatcctctt ggcatgcccc tcccagcacg aactagatca gctggccacc cttaccgcac      480
agctattgtc ctctcatggt ctcccagttt cccaggaaaa acccaacgc accccaggaa       540 aaatacactt cctgggccaa atcatacatc cagatcacat cacctatgaa accacccca      600 ccatccccat taaggcacac tggaccctga ctgaactgca aaccctcctg ggggagctcc      660
agtgggtctc caaggggact cctgtcctcc gagaacacct tcactgtctc tactcagcct      720
tgagaggtct caaagacccc cgggacacta tcacccttcg tcatcctcac ctccacgctc      780
tccacaacat tcagcaagcc ctgcatcaca attgccgcgg tcgccttgac tctacgctcc      840
ccctccttgg cctcatcttc ctcagtccat ccggcacgac ctcagtcctc ttccagacaa      900
atcataaatg gccctagtc tggctccacg ccccccatcc cccgaccagc ctatgcccct       960
gggggcacat actcgcctgc actgtactta cccttgacaa gtatgccttg cagcactatg     1020
gccaactatg caaatcattc catcataaca tgtccaccca ggccctacac gatttcgtaa     1080
aaaattcctc tcaccccagc gtcgccatat taattcacca catgcatcgg ttctgtgatc     1140
tgggcagaca gccaccggga ccctggcgaa ccctcttaca actcccggcc cttctccggg     1200
aaccccagct cctcaggcct gcatttccc tatccccagt ggttatagat caggccctt      1260 gtctgttctc tgatgggtct ccccaaaagg ccgcctatgt aatttgggac aaggtcattc     1320
tcagccagcg gtcggtcccc ctgccccccc atgccaataa ctcagcacaa aaggggaat     1380 tagtcggact cctcttgggc ttgcaagccg cacagccctg gccatccctt aacattttcc     1440
tagactcaaa gttcctcatc cggtacctcc agtccctcgc ttccggggcc ttccaaggat     1500
catccacaca ccaccgtctc caggcgtccc tgcccacact cctccagggc aaggtcgtgt     1560
atctccacca caccgcagc cacacccaat tgcctgatcc catctcgacc ctcaatgaat      1620
ataccgactc tctcattgtc gcccccgtaa ccccttgaa gctgagggc ctccatgccc       1680 tcacccactg caaccaacag gccctcgttt cccacggagc caccctgca caggctaagc      1740 aactcgtgca ggcctgccgc acctgtcaaa tcattaaccc tcaacaccac atgccgcgtg     1800
gccacatccg ccgcggccac ttcccaaacc acacatggca aggagatgtc acccaccta      1860 agcacaaacg gacccgatac tgcctccacg tctgggtgga taccttctca ggtgcggtat     1920
cttgtgtctg caaaaagaaa gaaactagca gcgaccttat caaaaccctc ctacatgcca     1980
tctccgtgct aggcaagccc ttctctgtta acacggacaa tggacccgct tacctttctc     2040
aggagttcca cgaattctgt accaccctct gcatcaaaca ctccacccat attccctaca     2100
atccgacaag ttcaggcctg gtggagcgca caaatggcat tctcaagaca ctactataca     2160
aatatttcct agaccaccct gacctccccc tagaaagcgc ggtttcaaag gctctctgga     2220
ccattaacca tttaaatgtc atgcgcccct gtggtaagac tcggtggcag ctccatcaca     2280
ccccccccct gcctcctatt tccgagtcca tacaaaccac tcccaccagg ctacattggt     2340
actattacaa aaccctggg cttaccaacc agcgatggaa agggcccgta caatctctcc      2400
aggaagcagc aggagcagct ctccttcaag tcagtgacgg ctcgcccag tggatcccctt    2460 ggcggctcct gaagaagact gtatgcccaa aacccgacga ccccgaaccc gcagggcacg     2520
tcgaaacaga ccaccaacac catgggtaac gtactcttct taactttatt ggccaccctg     2580
ggcatcccag tacttcaggc cagccggtgt acaatcacgg taggtatctc ctcctaccac     2640
```

```
tccagccct  gcagcccagc  ccagcctttta  tgtacctggg  ccctcgacct  tgtgtccatc   2700
actaaggacc  agctcctcta  ccccccctgc  caaaacctga  tcacctattc  caactaccac   2760
aagacctact  ccctgtatct  cttcccacac  tgggtacaaa  agccactccg  ccggggcttt   2820
ggatactact  cagcctccta  ctctgatcct  tgctccctac  aatgtcccta  cctaggaagt   2880
caatcatgga  cttgcccta   tactggccct  gtctcgagcc  caacttggag  attctccaca   2940
gatgtaaatt  tcacccaaga  agtcagccgt  gtctccctaa  aacttcattt  ctccaaatgt   3000
ggttcctcct  taactctgtt  aatagatgcc  cccggttacg  atccgctgtg  gtacctcaca   3060
tccgagccta  ctcaggaacc  cccaaccct   ccgccactag  tcagcgactc  agacctagag   3120
catgtcctga  ctccttcggc  ctcctgggcc  tccaagatgc  tgaccctcat  ccacctaacc   3180
ttgcagagca  ccaactattc  ctgtatggtc  tgtattgacc  gcgccagcct  ctcttcctgg   3240
cacgtattat  acactcccaa  catctctagt  aatgcccct   caaaacccat  cgtccgccct   3300
tcccttgccc  tatccgcccc  gcgaccacag  cccttcccct  ggacccattg  ctatcaacca   3360
caggtgcaag  ctgtaaccac  cgcaaagtgc  aataattcca  tcatacttcc  cccatttttct   3420 ctctctcct   tgcctggtgc  ccctctcact  aggcgacgcc  gggccgtccc  agtggcggtc   3480
tggctcgttt  ccgctttggc  cgcagggaca  ggaatagcag  gaggtgtcac  cgggtcctta   3540
tccctggcct  ccagtagaag  tctcctgtcc  gaagtggaca  aggatatttc  ccacctcaca   3600
cgggccattg  taaaaaacca  ccaaaacatt  cttcgagtgg  cccaatatgc  cgcccaaaac   3660
aggcgagggt  tagacctcct  gttctgggaa  caaggggggc  tgtgtaaagc  gatacaagaa   3720
caatgctgct  tcctcaacat  cagcaatacc  catatttcag  tcttacaaga  gcgaccccct   3780
ctagaaactc  gggtaactac  tggatggggc  ttaaattggg  atctaggact  ctcccagtgg   3840
gcccgtgagg  ctctccagac  tggtattacc  cttttggccc  tccttctgtt  aatcatcatc   3900
ctcgggccct  gcattattcg  ccagctgcaa  gccctccccc  agaggctaca  gcagcgacct   3960
gaccagtacc  ctctcctcaa  ccctgagacc  cctttataat  aactccgcca  atacacccaa   4020 caggtccca   tggttgaccc  ctctaccgtt  cacccacccg  cactccgcta  gacctgacga   4080
gtccccccat  atgtccaaag  tctgttccaa  gccagctgat  aaccgaaata  attctcctaa   4140
gttatggtta  cattcctcct  ccagatcctt  cctttccttc  tctaatacat  caatatagcc   4200
ttgcaacaag  tcacaatacc  cctcaaaccc  cagcaggtcc  atgcacttcc  gttgttgatg   4260
acgcgcctct  ctctccttgc  gcttcctctc  cctctcctgc  aatcgctccc  tccgccgcgc   4320
ctccttttcc  tcctgttctc  gcaggagccg  ctgaatctcc  gcctgctcgt  ccaccagggc   4380
cctcaggcga  gacttccggg  taccatcatt  ggcgcctccc  gacccagggg  ggcggccttt   4440
gcgcgcacga  cgagcgccgc  taccaggcat  ctcctctggt  gttgagacct  tctttgcccg   4500
atcctctgat  gataacccc   taaaaaattc  tataaaaaat  tccccgttat  ttttttcagc   4560
ccacttccca  ggattcgggc  agagcctcct  ctatggatac  ccgtctatg   tgtttggcga   4620 ttgtgttcaa  gccgattggt  gccccatctc  cggtggatta  tgctccccc   gcctacatcg   4680 ccacgccctc  ctggccacct  gccccgagca  ccagatcacc  tgggaccca   tcgatggacg   4740 agttgtcggc  tcgcctctcc  aataccttat  ccctcgcctc  cctccttcc   ccacccaacg   4800 aacctccaag  accctcaaag  tccttacccc  accaaccact  cctgtcaccc  caaggttcc    4860 accctccttc  tttcagtccg  tgcggaggca  cagcccctac  cgcaacggat  gtcttgaaac   4920
aacccttgga  gagcagctcc  cctcccttgc  atttcctgag  ccaggcctca  ggccccaaaa   4980
cgtctacacc  atctggggaa  agaccatagt  gtgtctatac  atctaccagc  tgtcccctcc   5040
```

```
catgacctgg cccctcattc cccatgtcat attttgcaac cccaggcagc ttggcgcttt    5100
tctaagcaat gtgcccccca agcgattaga agaactcctc tacaaacttt atctacacac    5160
cggcgccata atcatcctgc cggaagacgc cctgcctacc accctatttc agcctgttcg    5220
agcaccctgt gtccaaacta cctggaacac aggacttctc ccataccagc caaacctgac    5280
tacccctggc ctgatatgga cctttaatga tgggtctcct                           5320
```

<210> SEQ ID NO 54
<211> LENGTH: 485
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 54

Met Gly Asn Val Leu Phe Leu Thr Leu Leu Ala Thr Leu Gly Ile Pro
 1               5                  10                  15

Val Leu Gln Ala Ser Arg Cys Thr Ile Thr Val Gly Ile Ser Ser Tyr
            20                  25                  30

His Ser Pro Cys Ser Pro Ala Gln Pro Leu Cys Thr Trp Ala Leu
        35                  40                  45

Asp Leu Val Ser Ile Thr Lys Asp Gln Leu Leu Tyr Pro Pro Cys Gln
    50                  55                  60

Asn Leu Ile Thr Tyr Ser Asn Tyr His Lys Thr Tyr Ser Leu Tyr Leu
65                  70                  75                  80

Phe Pro His Trp Val Gln Lys Pro Leu Arg Arg Gly Leu Gly Tyr Tyr
                85                  90                  95

Ser Ala Ser Tyr Ser Asp Pro Cys Ser Leu Gln Cys Pro Tyr Leu Gly
            100                 105                 110

Ser Gln Ser Trp Thr Cys Pro Tyr Thr Gly Pro Val Ser Ser Pro Thr
        115                 120                 125

Trp Arg Phe Ser Thr Asp Val Asn Phe Thr Gln Glu Val Ser Arg Val
    130                 135                 140

Ser Leu Lys Leu His Phe Ser Lys Cys Gly Ser Ser Leu Thr Leu Leu
145                 150                 155                 160

Ile Asp Ala Pro Gly Tyr Asp Pro Leu Trp Tyr Leu Thr Ser Glu Pro
                165                 170                 175

Thr Gln Glu Pro Pro Thr Pro Pro Leu Val Ser Asp Ser Asp Leu
            180                 185                 190

Glu His Val Leu Thr Pro Ser Ala Ser Trp Ala Ser Lys Met Leu Thr
        195                 200                 205

Leu Ile His Leu Thr Leu Gln Ser Thr Asn Tyr Ser Cys Met Val Cys
    210                 215                 220

Ile Asp Arg Ala Ser Leu Ser Ser Trp His Val Leu Tyr Thr Pro Asn
225                 230                 235                 240

Ile Ser Ser Asn Ala Pro Ser Lys Pro Ile Val Arg Pro Ser Leu Ala
                245                 250                 255

Leu Ser Ala Pro Arg Pro Gln Pro Phe Pro Trp Thr His Cys Tyr Gln
            260                 265                 270

Pro Gln Val Gln Ala Val Thr Thr Ala Lys Cys Asn Asn Ser Ile Ile
        275                 280                 285

Leu Pro Pro Phe Ser Leu Ser Pro Leu Pro Gly Ala Pro Leu Thr Arg
    290                 295                 300

Arg Arg Arg Ala Val Pro Val Ala Val Trp Leu Val Ser Ala Leu Ala

```
                305                 310                 315                 320
Ala Gly Thr Gly Ile Ala Gly Val Thr Gly Ser Leu Ser Leu Ala
                    325                 330                 335

Ser Ser Arg Ser Leu Leu Ser Glu Val Asp Lys Asp Ile Ser His Leu
                340                 345                 350

Thr Arg Ala Ile Val Lys Asn His Gln Asn Ile Leu Arg Val Ala Gln
                355                 360                 365

Tyr Ala Ala Gln Asn Arg Arg Gly Leu Asp Leu Leu Phe Trp Glu Gln
            370                 375                 380

Gly Leu Cys Lys Ala Ile Gln Glu Gln Cys Cys Phe Leu Asn Ile
385                 390                 395                 400

Ser Asn Thr His Ile Ser Val Leu Gln Glu Arg Pro Pro Leu Glu Thr
                405                 410                 415

Arg Val Thr Thr Gly Trp Gly Leu Asn Trp Asp Leu Gly Leu Ser Gln
                420                 425                 430

Trp Ala Arg Glu Ala Leu Gln Thr Gly Ile Thr Leu Leu Ala Leu Leu
            435                 440                 445

Leu Leu Ile Ile Ile Leu Gly Pro Cys Ile Ile Arg Gln Leu Gln Ala
450                 455                 460

Leu Pro Gln Arg Leu Gln Gln Arg Pro Asp Gln Tyr Pro Leu Leu Asn
465                 470                 475                 480

Pro Glu Thr Pro Leu
                485

<210> SEQ ID NO 55
<211> LENGTH: 307
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 55

Met Gly Asn Val Leu Phe Leu Thr Leu Leu Ala Thr Leu Gly Ile Pro
  1               5                  10                  15

Val Leu Gln Ala Ser Arg Cys Thr Ile Thr Val Gly Ile Ser Ser Tyr
                 20                  25                  30

His Ser Ser Pro Cys Ser Pro Ala Gln Pro Leu Cys Thr Trp Ala Leu
             35                  40                  45

Asp Leu Val Ser Ile Thr Lys Asp Gln Leu Leu Tyr Pro Pro Cys Gln
         50                  55                  60

Asn Leu Ile Thr Tyr Ser Asn Tyr His Lys Thr Tyr Ser Leu Tyr Leu
 65                  70                  75                  80

Phe Pro His Trp Val Gln Lys Pro Leu Arg Arg Gly Leu Gly Tyr Tyr
                 85                  90                  95

Ser Ala Ser Tyr Ser Asp Pro Cys Ser Leu Gln Cys Pro Tyr Leu Gly
                100                 105                 110

Ser Gln Ser Trp Thr Cys Pro Tyr Thr Gly Pro Val Ser Ser Pro Thr
            115                 120                 125

Trp Arg Phe Ser Thr Asp Val Asn Phe Thr Gln Glu Val Ser Arg Val
        130                 135                 140

Ser Leu Lys Leu His Phe Ser Lys Cys Gly Ser Ser Leu Thr Leu Leu
145                 150                 155                 160

Ile Asp Ala Pro Gly Tyr Asp Pro Leu Trp Tyr Leu Thr Ser Glu Pro
                165                 170                 175

Thr Gln Glu Pro Pro Thr Pro Pro Pro Leu Val Ser Asp Ser Asp Leu
```

-continued

```
                180                 185                 190
Glu His Val Leu Thr Pro Ser Ala Ser Trp Ala Ser Lys Met Leu Thr
                195                 200                 205

Leu Ile His Leu Thr Leu Gln Ser Thr Asn Tyr Ser Cys Met Val Cys
                210                 215                 220

Ile Asp Arg Ala Ser Leu Ser Ser Trp His Val Leu Tyr Thr Pro Asn
225                 230                 235                 240

Ile Ser Ser Asn Ala Pro Ser Lys Pro Ile Val Arg Pro Ser Leu Ala
                245                 250                 255

Leu Ser Ala Pro Arg Pro Gln Pro Phe Pro Trp Thr His Cys Tyr Gln
                260                 265                 270

Pro Gln Val Gln Ala Val Thr Thr Ala Lys Cys Asn Asn Ser Ile Ile
                275                 280                 285

Leu Pro Pro Phe Ser Leu Ser Pro Leu Pro Gly Ala Pro Leu Thr Arg
                290                 295                 300

Arg Arg Arg
305

<210> SEQ ID NO 56
<211> LENGTH: 178
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 56

Ala Val Pro Val Ala Val Trp Leu Val Ser Ala Leu Ala Ala Gly Thr
1               5                   10                  15

Gly Ile Ala Gly Gly Val Thr Gly Ser Leu Ser Leu Ala Ser Ser Arg
                20                  25                  30

Ser Leu Leu Ser Glu Val Asp Lys Asp Ile Ser His Leu Thr Arg Ala
                35                  40                  45

Ile Val Lys Asn His Gln Asn Ile Leu Arg Val Ala Gln Tyr Ala Ala
            50                  55                  60

Gln Asn Arg Arg Gly Leu Asp Leu Leu Phe Trp Glu Gln Gly Gly Leu
65              70                  75                  80

Cys Lys Ala Ile Gln Glu Gln Cys Cys Phe Leu Asn Ile Ser Asn Thr
                85                  90                  95

His Ile Ser Val Leu Gln Glu Arg Pro Pro Leu Glu Thr Arg Val Thr
                100                 105                 110

Thr Gly Trp Gly Leu Asn Trp Asp Leu Gly Leu Ser Gln Trp Ala Arg
                115                 120                 125

Glu Ala Leu Gln Thr Gly Ile Thr Leu Leu Ala Leu Leu Leu Leu Ile
                130                 135                 140

Ile Ile Leu Gly Pro Cys Ile Ile Arg Gln Leu Gln Ala Leu Pro Gln
145                 150                 155                 160

Arg Leu Gln Gln Arg Pro Asp Gln Tyr Pro Leu Leu Asn Pro Glu Thr
                165                 170                 175

Pro Leu

<210> SEQ ID NO 57
<211> LENGTH: 848
<212> TYPE: PRT
<213> ORGANISM: Artificial Sequence
<220> FEATURE:
<223> OTHER INFORMATION: Description of Artificial Sequence;
      note=synthetic construct
```

```
<400> SEQUENCE: 57

Gly His Ile Glu Pro Tyr Ser Gly Pro Gly Asn Asn Pro Val Phe Pro
  1               5                  10                  15

Val Lys Lys Pro Asn Gly Lys Trp Arg Phe Ile His Asp Leu Arg Ala
             20                  25                  30

Thr Asn Ala Ile Thr Thr Thr Leu Ala Ser Pro Ser Pro Gly Pro Pro
             35                  40                  45

Asp Leu Thr Ser Leu Pro Gln Ala Leu Pro His Leu Gln Thr Ile Asp
         50                  55                  60

Leu Thr Asp Ala Phe Phe Gln Ile Pro Leu Pro Lys Arg Phe Gln Pro
 65                  70                  75                  80

Tyr Phe Ala Phe Thr Ile Pro Gln Pro Leu Asn His Gly Pro Gly Ser
                 85                  90                  95

Arg Tyr Ala Trp Thr Val Leu Pro Gln Gly Phe Lys Asn Ser Pro Thr
            100                 105                 110

Leu Phe Glu Gln Gln Leu Ala Ser Val Leu Gly Pro Ala Arg Lys Ala
        115                 120                 125

Phe Pro Thr Ser Val Ile Val Gln Tyr Met Asp Asp Ile Leu Leu Ala
130                 135                 140

Cys Pro Ser Gln His Glu Leu Asp Gln Leu Ala Thr Leu Thr Ala Gln
145                 150                 155                 160

Leu Leu Ser Ser His Gly Leu Pro Val Ser Gln Glu Lys Thr Gln Arg
                165                 170                 175

Thr Pro Gly Lys Ile His Phe Leu Gly Gln Ile His Pro Asp His
            180                 185                 190

Ile Thr Tyr Glu Thr Thr Pro Thr Ile Pro Ile Lys Ala His Trp Thr
        195                 200                 205

Leu Thr Glu Leu Gln Thr Leu Leu Gly Glu Leu Gln Trp Val Ser Lys
    210                 215                 220

Gly Thr Pro Val Leu Arg Glu His Leu His Cys Leu Tyr Ser Ala Leu
225                 230                 235                 240

Arg Gly Leu Lys Asp Pro Arg Asp Thr Ile Thr Leu Arg His Pro His
                245                 250                 255

Leu His Ala Leu His Asn Ile Gln Gln Ala Leu His His Asn Cys Arg
            260                 265                 270

Gly Arg Leu Asp Ser Thr Leu Pro Leu Leu Gly Leu Ile Phe Leu Ser
        275                 280                 285

Pro Ser Gly Thr Thr Ser Val Leu Phe Gln Thr Asn His Lys Trp Pro
    290                 295                 300

Leu Val Trp Leu His Ala Pro His Pro Thr Ser Leu Cys Pro Trp
305                 310                 315                 320

Gly His Ile Leu Ala Cys Thr Val Leu Thr Leu Asp Lys Tyr Ala Leu
                325                 330                 335

Gln His Tyr Gly Gln Leu Cys Lys Ser Phe His His Asn Met Ser Thr
            340                 345                 350

Gln Ala Leu His Asp Phe Val Lys Asn Ser Ser His Pro Ser Val Ala
        355                 360                 365

Ile Leu Ile His His Met His Arg Phe Cys Asp Leu Gly Arg Gln Pro
    370                 375                 380

Pro Gly Pro Trp Arg Thr Leu Leu Gln Leu Pro Ala Leu Leu Arg Glu
385                 390                 395                 400

Pro Gln Leu Leu Arg Pro Ala Phe Ser Leu Ser Pro Val Val Ile Asp
                405                 410                 415
```

```
Gln Ala Pro Cys Leu Phe Ser Asp Gly Ser Pro Gln Lys Ala Ala Tyr
            420                 425                 430

Val Ile Trp Asp Lys Val Ile Leu Ser Gln Arg Ser Val Pro Leu Pro
            435                 440                 445

Pro His Ala Asn Asn Ser Ala Gln Lys Gly Glu Leu Val Gly Leu Leu
450                 455                 460

Leu Gly Leu Gln Ala Ala Gln Pro Trp Pro Ser Leu Asn Ile Phe Leu
465                 470                 475                 480

Asp Ser Lys Phe Leu Ile Arg Tyr Leu Gln Ser Leu Ala Ser Gly Ala
                485                 490                 495

Phe Gln Gly Ser Ser Thr His His Arg Leu Gln Ala Ser Leu Pro Thr
                500                 505                 510

Leu Leu Gln Gly Lys Val Val Tyr Leu His His Thr Arg Ser His Thr
            515                 520                 525

Gln Leu Pro Asp Pro Ile Ser Thr Leu Asn Glu Tyr Thr Asp Ser Leu
            530                 535                 540

Ile Val Ala Pro Val Thr Pro Leu Lys Pro Glu Gly Leu His Ala Leu
545                 550                 555                 560

Thr His Cys Asn Gln Gln Ala Leu Val Ser His Gly Ala Thr Pro Ala
                565                 570                 575

Gln Ala Lys Gln Leu Val Gln Ala Cys Arg Thr Cys Gln Ile Ile Asn
                580                 585                 590

Pro Gln His His Met Pro Arg Gly His Ile Arg Arg Gly His Phe Pro
            595                 600                 605

Asn His Thr Trp Gln Gly Asp Val Thr His Leu Lys His Lys Arg Thr
            610                 615                 620

Arg Tyr Cys Leu His Val Trp Val Asp Thr Phe Ser Gly Ala Val Ser
625                 630                 635                 640

Cys Val Cys Lys Lys Lys Glu Thr Ser Ser Asp Leu Ile Lys Thr Leu
                645                 650                 655

Leu His Ala Ile Ser Val Leu Gly Lys Pro Phe Ser Val Asn Thr Asp
            660                 665                 670

Asn Gly Pro Ala Tyr Leu Ser Gln Glu Phe His Glu Phe Cys Thr Thr
            675                 680                 685

Leu Cys Ile Lys His Ser Thr His Ile Pro Tyr Asn Pro Thr Ser Ser
            690                 695                 700

Gly Leu Val Glu Arg Thr Asn Gly Ile Leu Lys Thr Leu Leu Tyr Lys
705                 710                 715                 720

Tyr Phe Leu Asp His Pro Asp Leu Pro Leu Glu Ser Ala Val Ser Lys
                725                 730                 735

Ala Leu Trp Thr Ile Asn His Leu Asn Val Met Arg Pro Cys Gly Lys
            740                 745                 750

Thr Arg Trp Gln Leu His His Thr Pro Pro Leu Pro Pro Ile Ser Glu
            755                 760                 765

Ser Ile Gln Thr Thr Pro Thr Arg Leu His Trp Tyr Tyr Tyr Lys Thr
770                 775                 780

Pro Gly Leu Thr Asn Gln Arg Trp Lys Gly Pro Val Gln Ser Leu Gln
785                 790                 795                 800

Glu Ala Ala Gly Ala Ala Leu Leu Gln Val Ser Asp Gly Ser Pro Gln
                805                 810                 815

Trp Ile Pro Trp Arg Leu Leu Lys Lys Thr Val Cys Pro Lys Pro Asp
            820                 825                 830

Asp Pro Glu Pro Ala Gly His Val Glu Thr Asp His Gln His His Gly
```

<210> SEQ ID NO 58
<211> LENGTH: 90
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 58

Leu Ala Ile Ser Asn Leu Thr Leu Asp Gln Ala Thr Thr Gln Phe Ser
1               5                   10                  15

Leu Leu Lys Asn Pro Thr Ala Ser Gly Asp Leu Ser Met Thr Ser Gly
            20                  25                  30

Pro Leu Met Pro Ser Pro Leu Pro Leu Pro Arg Pro Pro Ala Pro
        35                  40                  45

Leu Ile Leu Pro Ala Cys His Arg Pro Cys Pro Ile Phe Arg Pro Ser
    50                  55                  60

Ile Ser Arg Thr Leu Ser Ser Arg Phe Pro Ser Gln Ser Asp Ser Ser
65                  70                  75                  80

Pro Thr Ser Pro Leu Pro Ser Pro Ser His
                85                  90

<210> SEQ ID NO 59
<211> LENGTH: 273
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 59
ctggccatat cgaaccttac tctggaccag gcaacaaccc agttttccct gttaaaaaac      60
ccaacggcaa gtggcgattt atccatgacc tcagggccac taatgccatc accactaccc     120
ttgcctcgcc ctcccccggc ccccctgatc ttaccagcct gccacaggcc ttgccccatc     180
ttcagaccat cgatctcacg gacgctttct tccagattcc cctcccaaag cgattccagc     240
cctacttcgc ctttaccatc ccccagccat taa                                  273

<210> SEQ ID NO 60
<211> LENGTH: 170
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 60

Met Pro Lys Thr Arg Arg Pro Arg Thr Arg Arg Ala Arg Arg Asn Arg
1               5                   10                  15

Pro Pro Thr Pro Trp Pro Thr Ser Gln Asp Ser Gly Arg Ala Ser Ser
            20                  25                  30

Met Asp Thr Pro Ser Met Cys Leu Ala Ile Val Phe Lys Pro Ile Gly
        35                  40                  45

Ala Pro Ser Pro Val Asp Tyr Ala Pro Pro Ala Tyr Ile Ala Thr Pro
    50                  55                  60

Ser Trp Pro Pro Ala Pro Ser Thr Arg Ser Pro Gly Thr Pro Ser Met
65                  70                  75                  80

Asp Glu Leu Ser Ala Arg Leu Ser Asn Thr Leu Ser Leu Ala Ser Pro
                85                  90                  95

```
Pro Ser Pro Pro Asn Glu Pro Pro Arg Pro Ser Lys Ser Leu Pro His
            100                 105                 110

Gln Pro Leu Leu Ser Pro Pro Arg Phe His Pro Pro Ser Phe Ser Pro
        115                 120                 125

Cys Gly Gly Thr Ala Pro Thr Ala Thr Asp Val Leu Lys Gln Pro Leu
    130                 135                 140

Glu Ser Ser Ser Pro Pro Leu His Phe Leu Ser Gln Ala Ser Gly Pro
145                 150                 155                 160

Lys Thr Ser Thr Pro Ser Gly Glu Arg Pro
                165                 170

<210> SEQ ID NO 61
<211> LENGTH: 512
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 61
atgcccaaaa cccgacgacc ccgaacccgc agggcacgtc gaaacagacc accaacacca      60
tgcccacttc ccaggattcg ggcagagcct cctctatgga taccccgtct atgtgtttgg     120
cgattgtgtt caagccgatt ggtgccccat tccggtgga ttatgctccc ccgcctaca      180 tcgccacgcc ctcctggcca cctgccccga gcaccagatc acctgggacc ccatcgatgg     240
acgagttgtc ggctcgcctc tccaatacct tatccctcgc ctcccctcct tccccaccca     300
acgaacctcc aagaccctca agtccttac cccaccaacc actcctgtca cccccaaggt     360
tccaccctcc ttctttcagt ccgtgcggag gcacagcccc taccgcaacg gatgtcttga     420
aacaacccct tggagagcagc tcccctccct tgcatttcct gagccaggcc tcaggcccca     480
aaacgtctac accatctggg gaaagaccat ag                                   512

<210> SEQ ID NO 62
<211> LENGTH: 255
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 62

Met Ala His Phe Pro Gly Phe Gly Gln Ser Leu Leu Tyr Gly Tyr Pro
1               5                   10                  15

Val Tyr Val Phe Gly Asp Cys Val Gln Ala Asp Trp Cys Pro Ile Ser
            20                  25                  30

Gly Gly Leu Cys Ser Pro Arg Leu His Arg His Ala Leu Leu Ala Thr
        35                  40                  45

Cys Pro Glu His Gln Ile Thr Trp Asp Pro Ile Asp Gly Arg Val Val
    50                  55                  60

Gly Ser Pro Leu Gln Tyr Leu Ile Pro Arg Leu Pro Ser Phe Pro Thr
65                  70                  75                  80

Gln Arg Thr Ser Lys Thr Leu Lys Val Leu Thr Pro Thr Thr Pro
                85                  90                  95

Val Thr Pro Lys Val Pro Pro Ser Phe Phe Gln Ser Val Arg Arg His
            100                 105                 110

Ser Pro Tyr Arg Asn Gly Cys Leu Glu Thr Thr Leu Gly Glu Gln Leu
        115                 120                 125
```

```
Pro Ser Leu Ala Phe Pro Glu Pro Gly Leu Arg Pro Gln Asn Val Tyr
        130                 135                 140
Thr Ile Trp Gly Lys Thr Ile Val Cys Leu Tyr Ile Tyr Gln Leu Ser
145                 150                 155                 160
Pro Pro Met Thr Trp Pro Leu Ile Pro His Val Ile Phe Cys Asn Pro
                165                 170                 175
Arg Gln Leu Gly Ala Phe Leu Ser Asn Val Pro Pro Lys Arg Leu Glu
            180                 185                 190
Glu Leu Leu Tyr Lys Leu Tyr Leu His Thr Gly Ala Ile Ile Ile Leu
        195                 200                 205
Pro Glu Asp Ala Leu Pro Thr Thr Leu Phe Gln Pro Val Arg Ala Pro
    210                 215                 220
Cys Val Gln Thr Thr Trp Asn Thr Gly Leu Leu Pro Tyr Gln Pro Asn
225                 230                 235                 240
Leu Thr Thr Pro Gly Leu Ile Trp Thr Phe Asn Asp Gly Ser Pro
                245                 250                 255
```

<210> SEQ ID NO 63
<211> LENGTH: 559
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 63

```
taactccgcc aatacaccca acaggtcccc atggttgacc cctctaccgt tcacccaccc      60
gcactccgct agacctgacg agtcccccca tatgtccaaa gtctgttcca agccagctga     120
taaccgaaat aattctccta agttatggtt acattcctcc tccagatcct tcctttcctt     180
ctctaataca tcaatatagc cttgcaacaa gtcacaatac ccctcaaacc ccagcaggtc     240
catgcacttc cgttgttgat gacgcgcctc tctctccttg cgcttcctct ccctctcctg     300
caatcgctcc ctccgccgcg cctccttttc ctcctgttct cgcaggagcc gctgaatctc     360
cgcctgctcg tccaccaggg ccctcaggcg agacttccgg gtaccatcat tggcgcctcc     420
cgaccccagg gggcggcctt tgcgcgcacg acgagcgccg ctaccaggca tctcctctgg     480
tgttgagacc ttctttgccc gatcctctga tgataacccc ctaaaaaatt ctataaaaaa     540
ttccccgtta ttttttttca                                                 559
```

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 64

```
gattcccctc ccaaagcgat                                                  20
```

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 65

```
tgacggatgt ggggaaggct                                                  20
```

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 66
ttccccaagg cttcaaaaac agccccacgc                                     30

<210> SEQ ID NO 67
<211> LENGTH: 50
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 67

Ser Phe Ser Phe Leu Leu Asp Ala Pro Gly Tyr Asp Pro Val Trp Phe
1               5                   10                  15

Leu Ser Ser Gln Ala Thr Gln Ala Pro Pro Thr Pro Ala Pro Leu Ile
            20                  25                  30

Gln Asp Ser Asp Leu Gln His Ile Leu Glu Pro Ser Ile Pro Trp Ser
        35                  40                  45

Ser Lys
    50

<210> SEQ ID NO 68
<211> LENGTH: 48
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 68

Thr Leu Leu Ile Asp Ala Pro Gly Tyr Asp Pro Leu Trp Tyr Leu Thr
1               5                   10                  15

Ser Glu Pro Thr Gln Glu Pro Pro Thr Pro Pro Pro Leu Val Ser Asp
            20                  25                  30

Ser Asp Leu Glu His Val Leu Thr Pro Ser Ala Ser Trp Ala Ser Lys
        35                  40                  45

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 69
ggtaagatcc cactgggtcg agc                                            23

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 70

```
gaagccaggt ctcgggtgac g                                              21
```

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 71

```
cgctcccctg gagctctctc g                                              21
```

<210> SEQ ID NO 72
<211> LENGTH: 27
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 72

```
gccacttccc attgggcttt ttgacgg                                        27
```

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 73

```
gctctcaccg ataaagtaac aaacg                                          25
```

<210> SEQ ID NO 74
<211> LENGTH: 25
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 74

```
ggtaggaaga ggctcctatg aacag                                          25
```

<210> SEQ ID NO 75
<211> LENGTH: 28
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 75

```
caggactgca taacatacga gaccctcc                                       28
```

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 76

```
cctatgaaca gggtgcatcg actggg                                         26
```

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 77
cctaagcccc ccatgtccag ac                                              22

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 78
cgagagagct ccaggggagc g                                               21

<210> SEQ ID NO 79
<211> LENGTH: 29
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 79
cctactccct gtatgtattc ccccattgg                                       29

<210> SEQ ID NO 80
<211> LENGTH: 29
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 80
gctcgaccca gtgggatctt accgagtgg                                       29

<210> SEQ ID NO 81
<211> LENGTH: 8791
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 81
tgacagggac aacgaccctc tcccaggggc gacagcaagc ccccaaggac aaaactagca      60
gggactagtc atcagccaaa aaggtcaact gtctcacaca aataaggatc cgaaggttct     120
gacgtcccag cccagcctca aaccaggaa atccatagaa atgcacctcg cccttaccca     180
cttcccctat catgaaaaac aaaggctgtg acgactaccc ccttcccaa aaatttgct      240 taaaccatca ataagacag cctagcctat ataagcatga ggatggttca ggaggggct      300 cgctctcttg ccgatcgccc tgctcacctc gagtgtccat ctcctggtca atcagttgag    360
acgccgccgg ctgccggtct cctggttgtc gcacctcctg aaccaccct tgggtaagtc     420 cccccttggt ccgagcttgg ctacggtttc tgtagtcgct cccaggaag tctccgagac     480

-continued

```
tgcccaagcc tctgcttgca aggctacggc cctccacccc tcttccgcgt ccgtgttaat    540
ctcttcgcgc caaccgaaaa cgaaagcgcc tccagctctc ttggcccggg gccaggcctg    600
agccgcgcgg gcgcaccacc ttaagcccgc tgtactcaaa cccctccggg aggggcccttt   660 tacagtaggc gcccgtcccc ccgggggaaa catacaagtg ggggctcgtc cgggatctgt    720
tccgctctcg ccgttccccc cctcccacta tgggtcagac ccacacatcc agtcccgtcc    780
ctaaggcccc caggggggctc tccacccacc actggcttaa tttcctgcag gcggcttacc   840
gcctgcaacc tggacccctcc gaattcgatt ttcaccagtt aagacgattc cttaagctag    900
cgctccaaac cccagtctgg ttaaaccctaa tcgattactc cctcctagcc ggcctaatcc    960
ccaaggggta ccccggtcgg gtgaccgaga tcgttaatat cctcctccgc gctcatccac   1020
cccccagcgc cccggcaatt tccatgccca cggccaccgg cccggcccct gcccccccagc   1080 ctcaggaggc gcacacgccc ccccttatg cggagcctgc tgcgctccag tgccttccca    1140
ttatgcactc ccacggggcc ccctcgagcc accgccccttg gcagatgaaa gacttacaag   1200
ccattaaaca agaaattagc acctcagctc ccggcagtcc tcaatttatg cataccattc   1260
gacttgccat ccagcagttt gaccctacgg ctaaagatct acatgatctt ttgcagtact   1320
tgtgctcgtc ccttattgtc tcccttcacc accaacagct acaagcactc attgtggagg   1380 cagaaaccccg agggttgaca ggttacaatc ctatggcagg gcccctccgg gtacaagcaa   1440
acaaccccgc ccagcaaggc ctccagagag aataccaaag tctttggctg ccgcctttg    1500 cggccctgcc tggtaacacc cgagatcctt cctgggccgc aatattgcaa ggcctcgagg   1560
aaccttattg tgcctttgta gagcgcctca atgcggccct cgataatggt ctacctgaag   1620
gcacaccaaa ggaacccatc ctgcggccgc tggcatactc caatgccaac aaagaatgcc   1680
agaaactcct tcaggcgcgg ggccatacca acagtccct tggcgaaatg ctccgagcct   1740
gtcaggcttg gacaccaaag gataagacca aagttctagt agttcagccc cgtaaaaccc   1800
ctccaacaca accgtgcttc cggtgtggaa aggtgggaca ctggagccga gactgcactc   1860
agcctcgccc ccctccgggg ccctgccccc tatgtcagga cccatcccac tggaagcgag   1920
attgccccca gctaaaaacc ccgccggagg cagaagaacc cctcctagcg gattttgcctg  1980 cccttctccc ggaggaaaaa aactccccag gggggagaa ctagtctccc cccgacccgg   2040
taacgtgcct tccctgcttc cccttgtctc cctatggcag gcccaacaat ctctcctcaa   2100
tattaaagtt tccttcttcg atcgcccacc cctggcatca caggcgctcc tggacaccgg   2160
agccggcctc actgtcatgc cccaggtttt ggctcggggg ctcacggacc tccaggacac   2220
caccattctg ggggccggcg gtaaaaccca ctcccagttt aaactcctac ggtgtccggt   2280
acatgtatac ttgcccttcc gtagggctcc cgtgtcccctt ccctcatgtc taattgacac   2340
caagaatgag tggaccatca tcggccggga cgtcctgcag caatgccagg gggccctta    2400 cttaccggag gacctcccgg ccccgaccca gttatccccg gtgaccaccc ctgcagtcat   2460
cggcttagaa catcttccag agcccccaga ggtcagccag tttccttaa acctgaacgc   2520 ctccaggccc taatagacct ggtctccaag gcactggagg ctggccatat cgaaccttac   2580
tctggaccag gcaacaaccc agttttccct gttaaaaaac ccaacggcaa gtggcgattt   2640
atccatgacc tcagggccac taatgccatc accactaccc ttgcctcgcc ctcccccggc   2700 cccctgatc ttaccagcct gccacaggcc ttgcccatc ttcagaccat cgatctcacg    2760
gacgctttct tccagattcc cctcccaaag cgattccagc cctacttcgc ctttaccatc   2820
ccccagccat taaatcatgg gcctgggagc aggtacgctt ggacagtcct tcccaaggc    2880
```

-continued

```
ttcaaaaaca gccccacgct ctttgagcaa cagctggcca gcgtactagg cccagcccga    2940
aaagccttcc ccacatccgt catcgtccaa tacatggacg acatcctctt ggcatgcccc    3000
tcccagcacg aactagatca gctggccacc cttaccgcac agctattgtc ctctcatggt    3060
ctcccagttt cccaggaaaa aacccaacgc accccaggaa aaatacactt cctgggccaa    3120
atcatacatc cagatcacat cacctatgaa accaccccca ccatcccat taaggcacac    3180 tggaccctga ctgaactgca aaccctcctg ggggagctcc agtgggtctc caaggggact    3240
cctgtcctcc gagaacacct tcactgtctc tactcagcct tgagaggtct caaagacccc    3300
cgggacacta tcacccttcg tcatcctcac ctccacgctc tccacaacat tcagcaagcc    3360
ctgcatcaca attgccgcgg tcgccttgac tctacgctcc ccctccttgg cctcatcttc    3420
ctcagtccat ccggcacgac ctcagtcctc ttccagacaa atcataaatg cccctagtc    3480 tggctccacg ccccccatcc cccgaccagc ctatgcccct gggggcacat actcgcctgc    3540
actgtactta cccttgacaa gtatgccttg cagcactatg ccaactatg caaatcattc    3600 catcataaca tgtccaccca ggccctacac gatttcgtaa aaaattcctc tcaccccagc    3660
gtcgccatat taattcacca catgcatcgg ttctgtgatc tgggcagaca gccaccggga    3720
ccctggcgaa ccctcttaca actcccggcc cttctccggg aaccccagct cctcaggcct    3780 gcatttccc tatccccagt ggttatagat caggccccct gtctgttctc tgatgggtct    3840
ccccaaaagg ccgcctatgt aatttgggac aaggtcattc tcagccagcg gtcggtcccc    3900
ctgccccccc atgccaataa ctcagcacaa aaggggggaat tagtcggact cctcttgggc    3960
ttgcaagccg cacagccctg ccatcccttt aacatttttcc tagactcaaa gttcctcatc    4020
cggtacctcc agtccctcgc ttccggggcc ttccaaggat catccacaca ccaccgtctc    4080
caggcgtccc tgcccacact cctccagggc aaggtcgtgt atctccacca cacccgcagc    4140
cacacccaat tgcctgatcc catctcgacc ctcaatgaat ataccgactc tctcattgtc    4200
gcccccgtaa ccccccttgaa gcctgagggc ctccatgccc tcacccactg caaccaacag    4260
gccctcgttt cccacggagc cacccctgca caggctaagc aactcgtgca ggcctgccgc    4320
acctgtcaaa tcattaaccc tcaacaccac atgccgcgtg ccacatccg ccgcggccac    4380 ttcccaaacc acacatggca aggagatgtc acccaccttta agcacaaacg gacccgatac    4440
tgcctccacg tctgggtgga taccttctca ggtgcggtat cttgtgtctg caaaaagaaa    4500
gaaactagca gcgaccttat caaaaccctc ctacatgcca tctccgtgct aggcaagccc    4560
ttctctgtta acacgacaa tggacccgct tacctttctc aggagttcca cgaattctgt    4620
accaccctct gcatcaaaca ctccaccccat attccctaca atccgacaag ttcaggcctg    4680
gtggagcgca caaatggcat tctcaagaca ctactataca aatatttcct agaccaccct    4740
gacctccccc tagaaagcgc ggtttcaaag gctctctgga ccattaacca tttaaatgtc    4800
atgcgccccc gtggtaagac tcggtggcag ctccatcaca cccccccct gcctcctatt    4860 tccgagtcca tacaaaccac tcccaccagg ctacattggt actattacaa aaccccctgga    4920 cttaccaacc agcgatggaa agggcccgta caatctctcc aggaagcagc aggagcagct    4980
ctccttcaag tcagtgacgg ctcgccccag tggatcccctt ggcggctcct gaagaagact    5040
gtatgcccaa aacccgacga ccccgaaccc gcagggcacg tcgaaacaga ccaccaacac    5100
catgggtaac gtactcttct taactttatt ggccaccctg gcatcccag tacttcaggc    5160 cagccggtgt acaatcacgg taggtatctc ctcctaccac tccagcccct gcagcccagc    5220
ccagccttta tgtacctggg ccctcgacct tgtgtccatc actaaggacc agctcctcta    5280
```

```
cccccccctgc caaaacctga tcacctattc caactaccac aagacctact ccctgtatct    5340
cttcccacac tgggtacaaa agccactccg ccggggcctt ggatactact cagcctccta    5400
ctctgatcct tgctccctac aatgtcccta cctaggaagt caatcatgga cttgcccta    5460
tactggccct gtctcgagcc caacttggag attctccaca gatgtaaatt tcacccaaga    5520
agtcagccgt gtctccctaa aacttcattt ctccaaatgt ggttcctcct taactctgtt    5580
aatagatgcc cccggttacg atccgctgtg gtacctcaca tccgagccta ctcaggaacc    5640
cccaacccct ccgccactag tcagcgactc agacctagag catgtcctga ctccttcggc    5700
ctcctgggcc tccaagatgc tgaccctcat ccacctaacc ttgcagagca ccaactattc    5760
ctgtatggtc tgtattgacc gcgccagcct ctcttcctgg cacgtattat acactcccaa    5820
catctctagt aatgcccect caaaacccat cgtccgccct tcccttgccc tatccgcccc    5880
gcgaccacag cccttcccct ggacccattg ctatcaacca caggtgcaag ctgtaaccac    5940
cgcaaagtgc aataattcca tcatacttcc cccattttct ctctctccct tgcctggtgc    6000
ccctctcact aggcgacgcc gggccgtccc agtggcggtc tggctcgttt ccgctttggc    6060
cgcagggaca ggaatagcag gaggtgtcac cgggtcctta ccctggcct ccagtagaag    6120
tctcctgtcc gaagtggaca aggatatttc ccacctcaca cgggccattg taaaaaacca    6180
ccaaaacatt cttcgagtgg cccaatatgc cgcccaaaac aggcgagggt tagacctcct    6240
gttctgggaa caaggggggc tgtgtaaagc gatacaagaa caatgctgct tcctcaacat    6300
cagcaatacc catatttcag tcttacaaga gcgacccccct ctagaaactc gggtaactac    6360
tggatggggc ttaaattggg atctaggact ctcccagtgg gcccgtgagg ctctccagac    6420
tggtattacc cttttggccc tccttctgtt aatcatcatc ctcgggccct gcattattcg    6480
ccagctgcaa gccctccccc agaggctaca gcagcgacct gaccagtacc ctctcctcaa    6540
ccctgagacc cctttataat aactccgcca atacacccaa caggtcccca tggttgaccc    6600
ctctaccgtt cacccacccg cactccgcta gacctgacga gtcccccat atgtccaaag    6660
tctgttccaa gccagctgat aaccgaaata attctcctaa gttatggtta cattcctcct    6720
ccagatcctt ccttttcctct tctaatacat caatatagcc ttgcaacaag tcacaatacc    6780
cctcaaaccc cagcaggtcc atgcacttcc gttgttgatg acgcgcctct ctctccttgc    6840
gcttcctctc cctctcctgc aatcgctccc tccgccgcgc ctccttttcc tctgttctc    6900
gcaggagccg ctgaatctcc gcctgctcgt ccaccagggc cctcaggcga gcttccggg    6960
taccatcatt ggcgcctccc gaccccaggg ggcggccttt gcgcgcacga cgagcgccgc    7020
taccaggcat ctcctctggt gttgagacct tctttgcccg atcctctgat gataacccc    7080
taaaaaattc tataaaaaat tccccgttat ttttttcagc ccacttccca ggattcgggc    7140
agagcctcct ctatggatac cccgtctatg tgtttggcga ttgtgttcaa gccgattggt    7200
gccccatctc cggtggatta tgctcccccc gcctacatcg ccacgccctc ctggccacct    7260
gccccgagca ccagatcacc tgggaccccca tcgatggacg agttgtcggc tcgcctctcc    7320
aatacccttat ccctcgcctc ccctccttcc ccacccaacg aacctccaag accctcaaag    7380
tccttacccc accaaccact cctgtcaccc ccaaggttcc accctccttc tttcagtccg    7440
tgcggaggca cagcccctac cgcaacggat gtcttgaaac aaccccttgga gagcagctcc    7500
cctcccttgc atttcctgag ccaggcctca ggccccaaaa cgtctacacc atctggggaa    7560
agaccatagt gtgtctatac atctaccagc tgtcccctcc catgacctgg ccctcattc    7620
cccatgtcat atttttgcaac cccaggcagc ttggcgcttt tctaagcaat gtgcccccca    7680
```

```
agcgattaga agaactcctc tacaaacttt atctacacac cggcgccata atcatcctgc    7740
cggaagacgc cctgcctacc accctatttc agcctgttcg agcaccctgt gtccaaacta    7800
cctggaacac aggacttctc ccataccagc caaacctgac taccctggc ctgatatgga    7860 cctttaatga tgggtctcct atgatttcag gaccttgccc taaggcaggg cagccatcct    7920
tggtagtaca gtcctcacta ctaatcttcg agagatttca aaccaaagcc tatcatccct    7980
cttacctcct ctcccaccaa ttgatacagt attcctcctt ccatcacctc tacttactct    8040
ttgatgaata tactactatc cccttctctc tactatttaa ggaaaaagag ggagatgaca    8100
gggacaacga ccctctccca ggggcgacag caagccccca aggacaaaac tagcagggac    8160
tagtcatcag ccaaaaaggt caactgtctc acacaaataa ggatccgaag gttctgacgt    8220
cccagcccag cctcaaaacc aggaaatcca tagaaatgca cctcgccctt acccacttcc    8280
cctatcatga aaacaaagg ctgtgacgac tacccccttc cccaaaaaat ttgcttaaac    8340
catcaataaa gacagcctag cctatataag catgaggatg gttcaggagg gggctcgctc    8400
tcttgccgat cgccctgctc acctcgagtg tccatctcct ggtcaatcag ttgagacgcc    8460
gccggctgcc ggtctcctgg ttgtcgcacc tcctgaacca ccccttgggt aagtcccccc    8520
ttggtccgag cttggctaca gtttctgtag tcgctcccag ggaagtctcc gagactgccc    8580
aagcctctgc ttgcaaggct acggcctcc acccctcttc cgcgtccgtg ttaatctctt    8640
cgcgccaacc gaaaacgaaa gcgcctccag ctctcttggc ccggggccag gcctgagccg    8700
cgcgggcgca ccaccttaag cccgctgtac tcaaacccct ccgggagggg ccctttacag    8760
taggcgcccg tcccccgggg ggaaacatac a    8791

<210> SEQ ID NO 82
<211> LENGTH: 7
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 82 gttaaac                                                                 7

<210> SEQ ID NO 83
<211> LENGTH: 7
<212> TYPE: DNA
<213> ORGANISM: Artificial Sequence
<220> FEATURE:
<223> OTHER INFORMATION: Description of Artificial Sequence;
      note=synthetic construct

<400> SEQUENCE: 83 tttaaac                                                                 7

<210> SEQ ID NO 84
<211> LENGTH: 61
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 84

Glu Arg Arg Arg Arg Cys Arg Glu Glu Leu Glu Glu Arg Lys Arg Gln
 1               5                  10                  15

Lys Lys Glu Arg Arg Gln Gln Leu Asp Cys Ile Asp Met Leu Gly Phe
            20                  25                  30
```

```
Glu Gly Phe Cys Asp Leu Leu Glu Gly Tyr Ile Asp Phe Leu Glu Arg
        35                  40                  45

Glu Ser Gln Gln Leu Arg Ala Gly Cys Glu Glu Ser Leu
    50                  55                  60
```

PRIMATE T-LYMPHOTROPIC VIRUSES

CROSS-REFERENCE TO RELATED APPLICATIONS

This is a continuation of U.S. patent application Ser. No. 11/678,596, filed Feb. 24, 2007, issued as U.S. Pat. No. 7,794, 998 on Sep. 14, 2010, which is a continuation-in-part of International Application No. PCT/US2006/005869, filed Feb. 21, 2006, which claims the benefit of U.S. Provisional Application No. 60/654,484, filed on Feb. 21, 2005, now expired. Each of these prior applications is incorporated by herein by reference.

ACKNOWLEDGEMENT OF GOVERNMENT SUPPORT

Aspects of this invention were made with United States government support. Therefore, the government has certain rights in the invention.

FIELD

Disclosed are compositions and methods related to the isolation and identification of the primate T-lymphotropic viruses, HTLV-3 and HTLV-4. The present disclosure also relates to vectors and vaccines for use in humans against infection and disease.

BACKGROUND

Primate T-lymphotropic viruses (PTLVs) are diverse deltaretroviruses, composed of 3 distinct species (PTLV-1, -2, -3) which by conventional nomenclature are named 'STLV' (simian T-lymphotropic virus) when found in non-human primates (NHPs) and 'HTLV' (human T-lymphotropic virus) when found in humans, regardless of suspected zoonotic origin (Mahieux et al., 1998; Salemi et al. 1999; Slattery et al., 1999; Courgnaud et al., 2004). Like HIV, HTLV has the potential to cause disease and circulate globally in humans sexually, from mother-to-child, and by exposure to contaminated blood from transfusions and intravenous drug use. HTLV-1 causes adult T-cell leukemia and HTLV-1-associated myelopathy/tropical spastic paraperesis (HAM/TSP) and other inflammatory diseases (Gessain & Mahieux 2000) and HTLV-2 has been associated with a neurologic disease similar to HAM/TSP (Araujo & Hall 2004). There has been no evidence to date of STLVs crossing into people occupationally exposed to NHPs in laboratories and primate centers, as has been documented with other primate retroviruses, including simian immunodeficiency virus (SW) (Khabbaz et al., 1994), simian foamy virus (SFV) (Switzer et al., 2004, Heneine et al., 1998), and simian type D retrovirus (Lerche et al. 2001). Nevertheless, ongoing zoonotic transmission of STLV to widespread human populations naturally exposed to NHPs through hunting or butchering, similar to that recently reported for SFV in African hunters (Wolfe et al., 2004b), would be of particular public health significance due to the transmissible and pathogenic nature of this group of viruses among humans. HTLV outside of the PTLV-1 and PTLV-2 groups has not previously been documented (Busch et al. 2000; VanDamme et al. 1997; Salemi et al. 1999; Slattery et al. 1999).

SUMMARY

Disclosed herein are compositions and methods that include the full and partial nucleic acid sequences of primate T-lymphotropic viruses known as HTLV-3 and HTLV-4, including viral fragments. These viruses are useful as reagents for the screening of human populations for the prevalence of such viruses. The disclosed viruses also can serve as vectors in gene therapy because the viruses appear to not be transmitted from humans to other humans. Additionally, the disclosed viruses can be used as reagents in pathogenicity studies of these and related viruses. Moreover, the sequences of the primate T-lymphotropic viruses described herein can be used as probes to detect virus in biological samples. Vectors are disclosed that express the HTLV-3 and HTLV-4 nucleic acid sequences, and include, but are not limited to, prokaryotic, eukaryotic and viral vectors. The disclosed viruses also can be used as live recombinant virus vaccines. Additionally, the disclosed viruses can be used as replicating viral systems to kill live dividing cells, either in vitro or in vivo.

The present disclosure also includes the isolation and characterization of primate T-lymphotropic viruses, HTLV-3 and HTLV-4, that are believed to have been transmitted from non-human primates to humans at some point in the past. The primate T-lymphotropic viruses described herein do not appear to be readily transmitted from human to human, and can be used in protocols for diagnosing primate T-lymphotropic virus infections, and as vectors in gene therapy procedures.

Compositions are provided that include live replicating retroviral vectors, wherein the vector is derived from a primate T-lymphotropic virus, and wherein the vector also includes a nucleic acid that encodes a primate T-lymphotropic virus peptide, polypeptide, or protein, or a fragment of a primate T-lymphotropic virus peptide, polypeptide, or protein. For example, the vector can be derived from an HTLV-3 or HTLV-4 virus. Thus, in one aspect, a composition is provided that includes live replicating primate T-lymphotropic virus vectors.

Also provided is a method of treating a subject with a condition, wherein the condition is a viral infection, bacterial infection, parasitic infection, proliferative disorder (e.g., cancer), or a condition associated with a genetic or autoimmune disorder. The method includes administering to the subject a live replicating viral vector, wherein the immunizing construct is specific for the condition.

Also provided is a method of preventing a condition in a subject, wherein the condition can be a viral infection, bacterial infection, parasitic infection, proliferative disorder, or a condition associated with a genetic or autoimmune disorder. The method includes administering to the subject a live replicating viral vector, wherein the antigen-encoding nucleic acid is specific for the condition. Also provided are methods of using the vectors, isolated viruses, and/or infectious clones described herein for making viral infection models and using models to study diseases and potential treatments, as well as the models themselves.

Also disclosed are methods and compositions for detecting primate T-lymphotropic virus or a protein encoded therein in biological fluids. The disclosure also encompasses antibodies specific for the primate T-lymphotropic virus and antibodies that inhibit the binding of antibodies specific for the primate T-lymphotropic virus. These antibodies can be polyclonal antibodies or monoclonal antibodies, which also includes fragments of any type of antibody. Thus, disclosed are antibodies to HTLV-3 or HTLV-4. The antibodies specific for the primate T-lymphotropic virus can be used in diagnostic kits to detect the presence and quantity of primate T-lymphotropic virus in biological fluids or in organs from nonhuman primates for xenotransplantation. For example, an HTLV-3 antibody can be used in a diagnostic kit to detect HTLV-3. Antibodies specific for primate T-lymphotropic virus may also be administered to a human or animal to passively immunize the human or animal against primate T-lymphotropic virus, thereby reducing infection, for instance after accidental exposure to nonhuman primate bodily fluids.

Other embodiments of the disclosure are methods and kits for detecting the presence and quantity of antibodies that bind primate T-lymphotropic virus, for example in body fluids. Such kits can be used for the detection of primate T-lymphotropic virus itself, or for the detection of antibodies to the primate T-lymphotropic virus, and also can be used to monitor the blood supply for the presence of primate T-lymphotropic virus. The disclosed kits include, for example, a kit for the detection of antibodies to HTLV-3 or HTLV-4.

Also included in the disclosure are recombinant live virus vaccines. The virus of the present disclosure has areas of its genome that make it useful for the insertion of exogenous genes. The inserted gene(s) can code for any protein for which vaccination or gene therapy is desired. A useful aspect of such recombinant live viruses is that the recombinant HTLV-3 or HTLV-4 does not cause disease in the host organism. The recombinant live virus vaccines of the present disclosure are a safe way to provide antigen to the immune system.

Accordingly, provided is a composition comprising a primate T-lymphotropic virus, or a fragment of the viral gene or the encoded protein. An example of the disclosed primate T-lymphotropic virus includes, but is not limited to HTLV-3 and HTLV-4. Also provided is a method of detecting a primate T-lymphotropic virus, such as HTLV-3 or HTLV-4.

Also provided are methods and compositions for detecting the presence and amount of primate T-lymphotropic virus in a body fluid or organ. Further embodiments are compositions and methods for treating genetic and physiologic disorders using gene therapy techniques that include the primate T-lymphotropic virus of the present disclosure as a vector for nucleic acid sequences and antisense sequences.

Further embodiments include providing compositions and methods useful for manipulating the expression of genes, providing vaccines, providing compositions and methods for treating viral infections in humans or animals, providing compositions and methods that are effective in treating genetic diseases, and providing a method of treating microbial infections in humans or animals. Yet still other embodiments include providing for treatments of conditions that are caused in part by rapidly dividing cellular growth, providing live recombinant virus vaccines, and providing diagnostic tools such as antibodies or antigens for the monitoring of the blood supply or organ and tissue donation for the presence of primate T-lymphotropic virus.

These and other features and advantages will become apparent after a review of the following detailed description of the disclosed embodiments and the appended claims.

BRIEF DESCRIPTION OF THE DRAWINGS

The accompanying drawings illustrate several embodiments and, together with the description, illustrate the disclosed compositions and methods.

FIG. 5(a) shows the nucleotide sequence of the HTLV-3 (2026ND) LTR and pre-gag region (nucleotides 1-755 of SEQ ID NO: 36). The U3-R-U5 locations (vertical lines), the approximate cap site (cap), the polyadenylation signal, TATA box, the predicted splice donor site (sd-LTR), and two 21-bp repeats are indicated. In the R and U5 regions, the predicted Rex core elements and nuclear riboprotein A1 binding sites are underlined. The pre-gag region and primer binding site (PBS, underlined) are in italics.

FIG. 6 shows the amino acid sequence of HTLV-3 Tax (SEQ ID NO: 50). Shown in boxes are known functional motifs: NLS, nuclear localization signal; (CBP)/P300, cAMP response element (CREB) binding protein; NES, nuclear export signal; CR2, C-terminal transcriptional activating domain binding; PDZ.

FIG. 7 shows the amino acid sequence of a basic leucine zipper (bZIP) transcription factor from HTLV-3 (SEQ ID NO: 84). Arginine rich and leucine zipper regions of the bZIP protein are boxed.

FIGS. 10A-10D show the full-length genomic sequence of HTLV-4(1863LE) (SEQ ID NO: 81).

Figure 11:
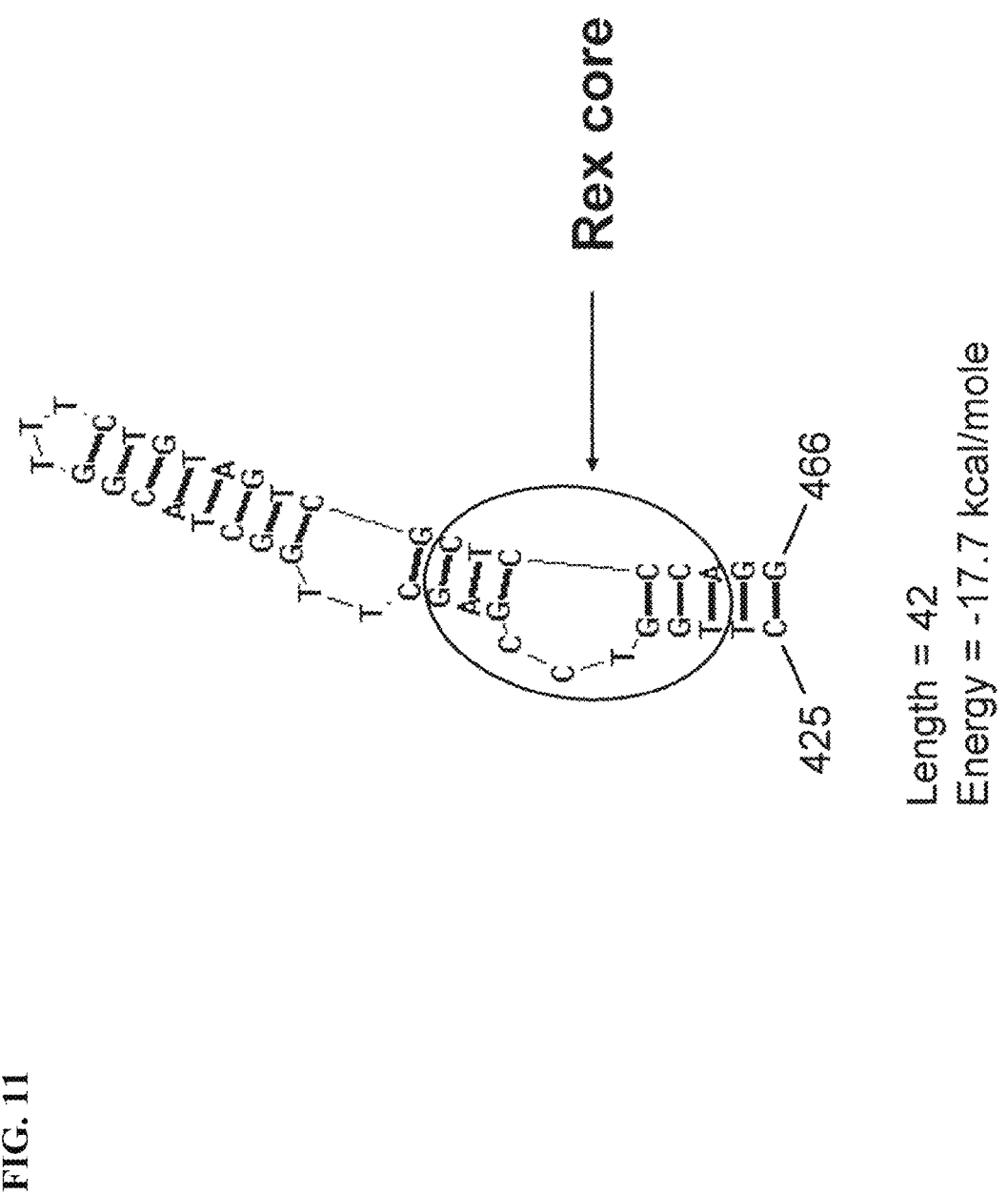

FIG. 11 shows the plot of predicted RNA stem loop secondary structure of the HTLV-4(1863LE) LTR region. Position of the Rex responsive element (RexRE) core is indicated (nucleotides 425-466 of SEQ ID NO: 81).

Figure 12:
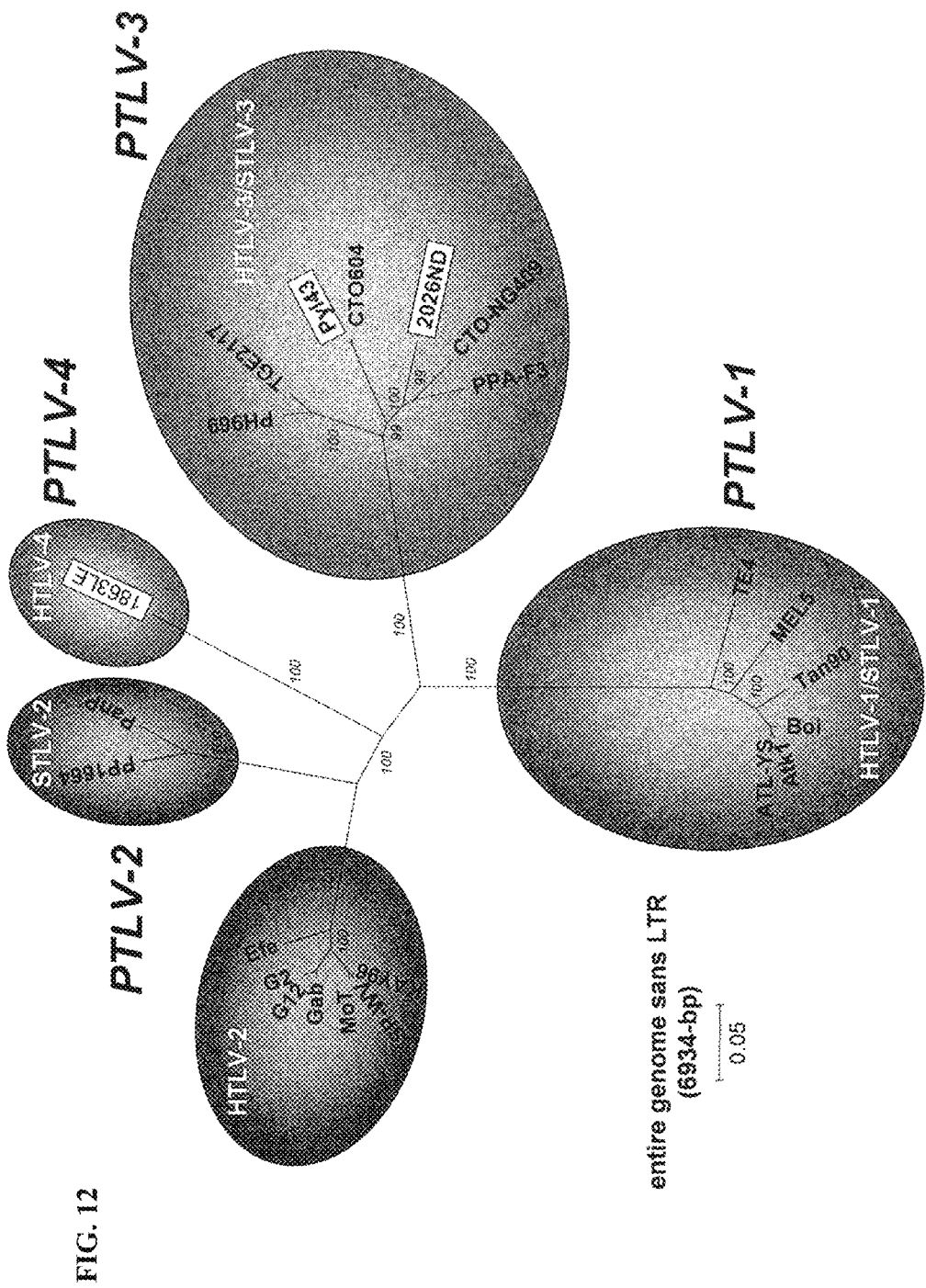

FIG. 12 shows the phylogenetic relationships of PTLV full-length genomic sequences, including full-length genomic HTLV-3 and HTLV-4. These findings confirm the genetic relationships found earlier that were based on smaller sequences. Four major phylogroups were inferred with very high bootstrap support. Nonhuman primate taxon codes are provided in the Methods portion of the Examples section of the specification. Support for the branching order was determined by 1,000 bootstrap replicates and only values 60% or greater are shown. Branch lengths are proportional to the evolutionary distance (scale bar) between the taxa.

Figure 13:
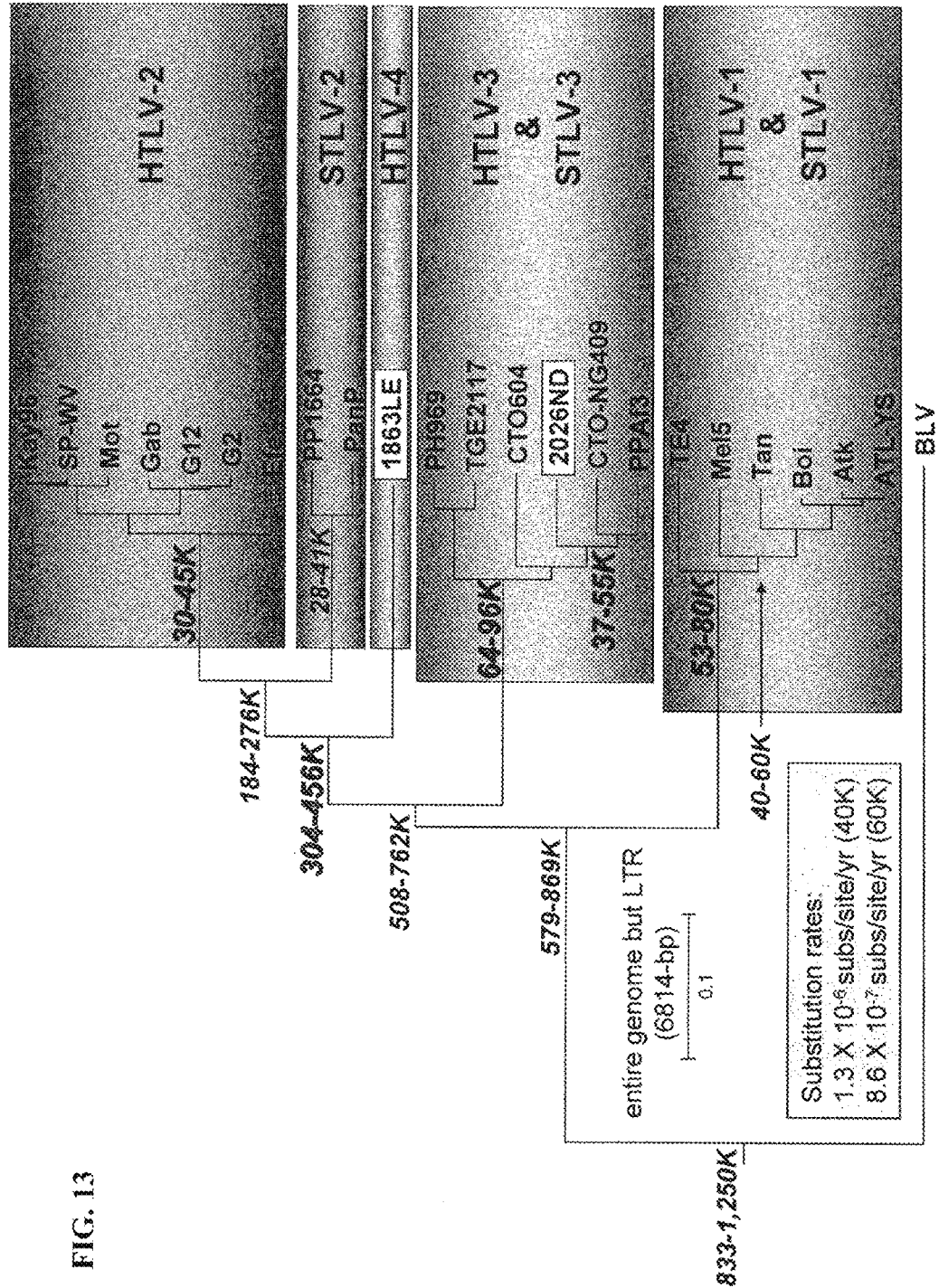

FIG. 13 shows the estimated divergence dates for the most recent common ancestor of HTLV-3(2026ND), HTLV-4 (1863LE) and other PTLVs. Divergence dates are provided for each major node of a neighbor-joining tree rooted with PTLV-1 as the outgroup; estimates are provided as ranges using as calibration points 40,000 and 60,000 years ago (YA) as the separation of the Melanesisan HTLV-1 (MEL5) sequence from other PTLV-1 strains. Using the bovine leukemia virus (BLV) as an outgroup, a substitution rate of $8.6 \times 10^{-7}$ to $1.3 \times 10^{-6}$ substitutions/site/year for PTLV was inferred which is 3 logs lower than that seen in HIV, confirming the genetic stability of these deltaretroviruses. Bootstrap analysis of 1,000 replicates is shown on the tree branches; only values >60% are shown.

DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

I. Terms

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that throughout the document, data are provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

Depending on context, the term "virus" is understood to include the infectious viral particle or the nucleic acid contained therein, or both.

Throughout this application, various publications are referenced. The disclosures of these publications in their entireties are hereby incorporated by reference into this application in order to more fully describe the state of the art to which this disclosure pertains. The references disclosed are also individually and specifically incorporated by reference herein for the material contained in them that is discussed in the sentence in which the reference is relied upon.

II. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular HTLV-3 or HTLV-4 or gene of the HTLV-3 or HTLV-4 such as gag, pol, env, LTR, rex, and tax is disclosed and discussed and a number of modifications that can be made are discussed, specifically contemplated is each and every combination and permutation of HTLV-3 or HTLV-4 or genes of the HTLV-3 or HTLV-4 such as gag, pol, env, LTR, rex, and tax and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Furthermore, although the disclosed nucleic acid sequences are represented as DNA sequences, it is understood that the equivalent RNA sequences also are contemplated. For instance, if a DNA sequence contains a thymine, it is understood that a uracil also can be substituted.

Disclosed herein are compositions relating to primate T-lymphotropic viruses HTLV-3 (SEQ ID NO: 36) and HTLV-4 (SEQ ID NOs: 53 and 81). It is understood and herein contemplated that the compositions of the disclosure can comprise the entire HTLV-3 or HTLV-4 virus nucleic acid sequence. It is also understood that the disclosed compositions can comprise proteins of the disclosed primate T-lymphocyte viruses or fragments of the disclosed proteins. For example, specifically disclosed and herein contemplated are compositions comprising SEQ ID NOs: 1, 3, 5, 35, 45, 47, 49, 51, and 52, or any combination thereof. Also disclosed are compositions comprising SEQ ID NOs: 2, 4, 6, 59, 61, and 63 or any combination thereof. Also disclosed are compositions comprising SEQ ID NOs: 37, 40, 44, 46, 48, and 50 or any combination thereof. Also disclosed are compositions comprising SEQ ID NOs: 54, 57, 58, 60, and 62 or any combination thereof. Also disclosed are compositions comprising fragments of the disclosed proteins. Thus, for example are compositions comprising SEQ ID NOs: 38, 39, 41, 42, and 43 or any combination thereof. Also disclosed are compositions comprising SEQ ID NOs: 55 and 56. It is understood and herein contemplated that any of the disclosed proteins can be used in combination with any of the protein fragments in the compositions disclosed herein. Thus, for example, disclosed herein are compositions comprising SEQ ID NOs: 37, 38, 39, 40, 41, 42, 43, 44, 46, 48, and 50 or any combination thereof. Also disclosed are SEQ ID NOs: 54, 55, 56, 57, 58, 60, and 62 or any combination thereof. SEQ ID NOs 1-6, 35, and 45 can be used for all the molecular biological techniques known to those skilled in the art. Such uses include, but are not limited to, generation of probes and vectors containing the sequences, antisense sequences derived from such sequences, and proteins synthesized using the sequences. RNA and other nucleic acid derivatives are contemplated by the present disclosure.

It is understood that there are known viruses in the art that based on certain genomic or sequence similarity or taxonomically related to the viruses disclosed herein. It is also understood that the known viruses in the art thought related taxonomically do not encode the specific viruses disclosed herein. Thus specifically disclosed and herein contemplated are isolated primate T-lymphotropic viruses having a pol gene that has less than 63.5% identity to the pol gene of HTLV-1, HTLV-2, STLV-2, and STLV-3, for example, HTLV-4. Also disclosed are isolated primate T-lymphotropic viruses having a gag gene that has less than 69% identity to the gag gene of HTLV-1, HTLV-2, STLV-2, and STLV-3, for example, HTLV-3. Also disclosed are isolated primate T-lymphotropic viruses having a pol gene that has less than 62% identity to the pol gene of HTLV-1, HTLV-2, STLV-2, and less than 86% identity to the pol gene of STLV-3, for example, HTLV-3. Similarly, the disclosed viruses can be distinguished based on the genes encoded by the disclosed viruses, and specifically the identity of said genes to the corresponding genes of known viruses. Thus, specifically disclosed are isolated primate T-lymphotropic viruses having a LTR that has less than 41% identity to the LTR of HTLV-1, HTLV-2 and STLV-3. Also disclosed are isolated primate T-lymphotropic viruses having at least 92.8% identity to the nucleic acid SEQ ID NO: 1.

Also disclosed are isolated primate T-lymphotropic virus having at least 92.5% identity to the nucleic acid SEQ ID NO: 3. Also disclosed are primate T-lymphotropic viruses having at least 94.2% identity to the nucleic acid SEQ ID NO: 5. Also disclosed are primate T-lymphotropic viruses having at least 91.5% identity to the nucleic acid SEQ ID NO: 35. Also disclosed are isolated primate T-lymphotropic viruses having at least 92.8% identity to the nucleic acid SEQ ID NO: 1, at least 92.5% identity to the nucleic acid SEQ ID NO: 3, and at least 94.2% identity to the nucleic acid SEQ ID NO: 5.

HTLV-4 is a unique delta primate T-lymphotropic virus that is distinct from all known PTLV lineages with 29-34.4% and 18.3-25% nucleotide divergence in the conserved pol and tax genes, respectively, a range of divergence similar to that between PTLV-1, PTLV-2, and PTLV-3. This virus formed a separate phylogenetic lineage with a long branch length and significant bootstrap support in both the pol (FIG. 2*a*) and tax (FIG. 2*c*) trees. Identical topologies were obtained by using maximum likelihood analysis. Phylogenetic analyses combined with GenBank blast searches show that this is the only known virus in this group. For these reasons, this virus, which was designated HTLV-4, qualifies as the first member of a group in the deltaretrovirus genus. Following the guidelines of the International Committee on Taxonomy of Viruses and pending formal classification, primate T-lymphotropic virus 4 (PTLV-4) was proposed as the name for this species, and PTLV-4(1863LE) as the prototype strain. Due to the classification of the virus within the family retroviridae, certain sequence similarity is expected to exist with known retroviruses. It is understood that the known viruses in the art thought to be related taxonomically do not encode the specific viruses disclosed herein. Thus, specifically disclosed and herein contemplated are isolated primate T-lymphotropic viruses having at least 71.5% identity to the nucleic acid SEQ ID NO: 2. Also disclosed are isolated primate T-lymphotropic viruses having at least 73.5% identity to the nucleic acid SEQ ID NO: 4. Also disclosed are isolated primate T-lymphotropic viruses having at least 82% identity to the nucleic acid SEQ ID NO: 6. Also disclosed are isolated primate T-lymphotropic viruses having at least 71.5% identity to the nucleic acid SEQ ID NO: 2, at least 73.5% identity to the nucleic acid SEQ ID NO: 4, and at least 82% identity to the nucleic acid SEQ ID NO: 6.

Knowing the sequence for HTLV-3 and/or HTLV-4 allows for various uses of the virus and viral sequences. The env gene of HTLV-3 and/or HTLV-4 is necessary for primate T-lymphotropic virus entry into animal cells. The genes of the present disclosure are effective in permitting infection of cells in a human host. Thus, for example, the env gene is used for uptake of foreign DNA by a wide range of human cells. There has long been a need for vectors for getting foreign nucleic acids into cells, both in vivo and in vitro. The introduction of foreign or exogenous nucleic acids into cells has been a technological hurdle for many gene therapy applications and has now been solved by the virus and sequences herein disclosed. The env sequences can be used with any vector known to those skilled in the art, and with any other genetic sequences of choice, to allow for entry of the nucleic acids into the cells.

The recent advent of technology, and advances in the understanding of the structure and function of many genes makes it possible to selectively turn off or modify the activity of a given gene. Alteration of gene activity can be accomplished many ways. For example, oligonucleotides that are complementary to certain gene messages or viral sequences, known as "antisense" compounds, have been shown to have an inhibitory effect against viruses. By creating an antisense compound that hybridizes with the targeted RNA message of cells or viruses the translation of the message into protein can be interrupted or prevented. In this fashion gene activity can be modulated.

The ability to deactivate specific genes provides great therapeutic benefits. For example, it is possible to fight viral diseases with antisense molecules that seek out and destroy viral gene products. In tissue culture, antisense oligonucleotides have inhibited infections by herpes-viruses, influenza viruses and the human immunodeficiency virus that causes AIDS. It is also possible to target antisense oligonucleotides against mutated oncogenes. Antisense technology also can be used to regulate growth and development. However, in order for the gene therapy to work, antisense sequences must be delivered across cellular plasma membranes to the cytosol.

Gene activity is also modified using sense DNA in a technique known as gene therapy. Defective genes are replaced or supplemented by the administration of "good" or normal genes that are not subject to the defect. Instead of being defective, the gene may have been deleted, thus replacement therapy would provide a copy of the gene for use by the cell. The administered normal genes can either insert into a chromosome or may be present as extracellular DNA and can be used to produce normal RNA, leading to production of the normal gene product. In this fashion gene defects and deficiencies in the production of a gene product may be corrected.

Still further gene therapy has the potential to augment the normal genetic complement of a cell. For example, one way to combat HIV is to introduce into an infected person's T cells a gene that makes the cells resistant to HIV infection. This form of gene therapy is sometimes called "intracellular immunization." Genetic material such as a polynucleotide sequence may be administered to a mammal in a viral vector to elicit an immune response against the gene product of the administered nucleic acid sequence. Such gene vaccines elicit an immune response in the following manner. First, the viral vector containing the nucleic acid sequence is administered to a human or animal. Next, the administered sequence is expressed to form a gene product within the human or animal. The gene product inside the human or animal is recognized as foreign material and the immune system of the human or animal mounts an immunological response against the gene product. The viruses disclosed herein can be used as viral vectors to provide the foreign nucleic acid sequences to the intracellular metabolic processes.

Additionally, gene therapy can be used as a method of delivering drugs in vivo. For example, if genes that code for therapeutic compounds can be delivered to endothelial cells, the gene products would have facilitated access to the blood stream. Additionally, cells could be infected with a retroviral vector such as the present disclosure carrying nucleic acid sequences coding for pharmaceutical agents that prevent infection from occurring in the retrovirally infected cells.

The primate T-lymphotropic viruses of the present disclosure can also be used a safe and effective vaccine agent. Genetic sequences for immunogenic proteins from a variety of infectious agents can be incorporated into the primate T-lymphotropic virus RNA. Once inside a cell, the gene product is expressed and releases the immunizing peptide to the body's immune system. In another method, the disclosed viruses can be used to immunize the body against cell markers found on cancer or tumor cells. The genetic sequence of the cancer cell marker is incorporated into the primate T-lymphotropic virus RNA, and after infection with the virus, the expressed gene product stimulates the immune system. The subject's immune system is used to remove the cancerous cells, obviating the need for chemotherapeutic methods.

Such treatment with HTLV-3 or HTLV-4 can be used for any condition in which rapidly dividing cells provide an aspect of the pathology of the condition. One such condition is the presence of uncontrolled angiogenesis within the body. Angiogenesis dependent diseases are well known in the art and are caused in part by the rapid growth of blood vessels. Another such condition is cancer or tumor growth. Cancer or tumors include both solid tumors and other types. Infection with the virus of the present disclosure, which can cause no disease and does not affect the host systemically, is an improvement over currently known treatments that involved systemically administered agents. Such chemotherapeutic agents kill rapidly dividing cells but also cause trauma to the entire person. The dosages of such chemotherapeutic agents must be titered between killing the cancer and killing the subject.

In contrast, the cancer treatments disclosed are not as harmful to the subject. The virus can either be administered systemically or injected in situ into the tumor. The infected cells are killed and tumor growth is stopped. The virus may be administered in one treatment or in a series of treatments.

The HTLV-3 or HTLV-4 of the present disclosure can be recombinantly modified to be selective for cellular receptors on the tumor to make the virus even more specifically targeted to just those cells. Additionally, the virus may have altered promoter regions that can be selectively activated to cause a productive infection. The combination of different levels of control of the virus, both natural and recombinantly-produced, are contemplated herein. A virus can be made specific for attachment to only certain types of cellular receptors, for those cells that are dividing, and will only undergo replication if another exogenous promoter factor is present. Viral infection by two or more individually defective viruses, that require factors or promoters supplied by other primate T-lymphotropic viruses or any type of virus, can provide for many levels of control of infection or treatment of specific conditions.

The virus may be administered to the host, for cancer treatment, gene therapy or vaccination by any methods known to those skilled in the art. Such methods include but are not limited to injection, inhalation, ingestion, topical administration and implantation. The virus may be killed or live, depending on the treatment considered.

The antibodies disclosed herein can be used to detect the presence of the disclosed viruses or viral particles. These antibodies can be used in diagnostic or screening kits to assess the presence of the virus. Additionally, the antibodies can be used to screen organs from nonhuman primates that may be used in humans. For instance, detection of the presence of a virus that is transmitted from nonhuman primates to humans is crucial in providing virus-free organs for transplantation.

It is believed that the virus of the present disclosure, comprising the isolates from HTLV-3, is the first definitive isolation of an STLV-3-like primate T-lymphotropic virus from persons exposed to nonhuman primates. This belief is supported by the epidemiology data, the PCR and sequencing data and the serology data and the absence of such reports in the literature. It is understood that HIV-1 and HIV-2 used to be called HTLV-III and HTLV-IV before it was known they were different types of viruses. Additionally, the virus of the present disclosure comprising the isolates from HTLV-4, are a new species in the delta primate T-lymphotropic viruses.

III. Vectors

Disclosed are live replicating human primate T-lymphotropic virus vectors suitable for human use comprising an immunizing construct, wherein the immunizing construct is inserted in nontranslated region between env and tax/rex. The disclosed immunizing construct can be an antigen-encoding nucleic acid.

Where reference is made to "antigen"-encoding nucleic acid, it is understood that in the context of the disclosure antigens encoded by the antigen-encoding nucleic acid can include but are not limited to immunogenic or non-immunogenic peptides, polypeptides, proteins, enzymes, cytokines. These antigens can be non-human exogenous antigenic sequences from viruses, bacteria, or parasites. The antigens can also be antigenic endogenous human or human derived sequences from a condition such as a cancer. Also, peptides encoded by the antigen-encoding nucleic acid can include non-antigenic sequences for the purposes of gene therapy.

In another embodiment of the present disclosure, sequences of the disclosed primate T-lymphotropic viruses can be used for other molecular biological applications. Regions of the gag gene are important in packaging genetic material. For example, the gag sequence or regions of the sequence are incorporated into other vectors and direct the packaging of the resultant genetic material for the particular application desired, such as packaging recombinant sequences to make altered infectious virions. Regions of the pol gene are known to be critical for the stable integration of foreign/viral DNA into the host genome. Vectors comprising the pol gene sequences can be used to integrate any DNA into a genome. The primate T-lymphotropic virus and sequences of the present disclosure infect human cells, and thus, these sequences are used with other foreign or exogenous sequences in humans in methods, including, but not limited to, entry into cells, packaging, and insertion into the genome. Additionally, methods of using the disclosed primate T-lymphotropic virus and other sequences of the present disclosure are not limited to human cells, but all cells that allow for infection or entry of the nucleic acids.

The present disclosure is directed to compositions and methods comprising new primate T-lymphotropic viruses, HTLV-3 and/or HTLV-4, particularly compositions and methods for the sequences of the viral genome. The virus was obtained from humans. The new virus of the present disclosure is an excellent vector for gene therapy and for vaccination purposes. Additionally, the antibodies or other detection methods for detecting the new virus are important in detecting the presence of this and related viruses for xenotransplantation. In addition, the disclosed primate T-lymphotropic viruses can be used as reagents in pathogenicity studies of these and related viruses. Moreover, the sequences of the disclosed primate T-lymphotropic viruses can be used as probes to detect virus in biological samples. Vectors include but are not limited to prokaryotic, eukaryotic and viral vectors.

Many new useful technologies have been developed that use viral vectors and form the basis of medical therapies. Examples of such technologies include, but are not limited to, gene replacement, antisense gene therapy, in situ drug delivery, treatment of cancer or infectious agents, and vaccine therapy. However, to be successful, these technologies require an effective means for the delivery of the genetic information across cellular membranes.

It is well-known in the art that vaccinations can be used prophylactically for the prevention of infections as well as therapeutically for the treatment of ongoing conditions. Such infections or conditions can be but are not limited to viral infections. Thus, also disclosed are vectors, wherein the antigen-encoding nucleic acid is an antigen from a virus. The viral antigen is selected from the group of viruses consisting of Herpes simplex virus type-1, Herpes simplex virus type-2, Cytomegalovirus, Epstein-Barr virus, Varicella-zoster virus, Human herpesvirus 6, Human herpesvirus 7, Human herpesvirus 8, Variola virus, Vesicular stomatitis virus, Hepatitis A virus, Hepatitis B virus, Hepatitis C virus, Hepatitis D virus, Hepatitis E virus, SARS, Rhinovirus, Coronavirus, Influenza virus A, Influenza virus B, Measles virus, Polyomavirus, Human Papillomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-lymphotropic virus type-1, Human T-lymphotropic virus type-2, Primate T-lymphotropic virus, Hantavirus, Rubella virus, Simian Immunodeficiency virus, Human Immunodeficiency virus type-1, Human Immunodeficiency virus type-2, and Simian Immunodeficiency virus (SW). Also disclosed are vectors, wherein the antigen-encoding nucleic acid is SIV-GAG. The art is replete with examples of viral antigens whose sequences and methods of obtaining them are well known.

Vaccinations are also known for the prevention of bacterial infections. Additionally, antibiotics are well-known in the art for the treatment of various bacterial infections. Herein contemplated and disclosed are vectors, wherein the antigen-encoding nucleic acid is an antigen from a bacterium. The bacterial antigen is selected from the group consisting of *M. tuberculosis, M. bovis, M. bovis* strain BCG, BCG substrains, *M. avium, M. intracellulare, M. africanum, M. kansasii, M. marinum, M. ulcerans, M. avium* subspecies *paratuberculosis, Nocardia asteroides*, other *Nocardia* species, *Legionella pneumophila*, other *Legionella* species, *Salmonella typhi*, other *Salmonella* species, *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Chlamydia pneumoniae, Chlamydia trachomatis, Chlamydia psittaci, Coxiella burnetti*, other *Rickettsial* species, *Ehrlichia* species, *Staphylococcus aureus, Staphylococcus epidermidis, Streptococcus pyogenes, Streptococcus agalactiae, Bacillus anthracis, Escherichia coli, Vibrio cholerae, Campylobacter* species, *Neiserria meningitidis, Neiserria gonorrhea, Pseudomonas aeruginosa*, other *Pseudomonas* species, *Haemophilus influenzae, Haemophilus ducreyi*, other *Hemophilus* species, *Clostridium tetani*, other *Clostridium* species, *Yersinia enterolitica*, and other *Yersinia* species. The art is replete with examples of bacterial antigens whose sequences and methods of obtaining them are well known.

Vaccinations are also known for the prevention of fungal infections. Additionally, antibiotics are well-known in the art for the treatment of various fungal infections. Herein contemplated and disclosed are vectors, wherein the antigen-encoding nucleic acid is an antigen from a fungus. The fungal antigen can be selected from the group consisting of *Candida albicans, Cryptococcus neoformans, Histoplasma capsulatum, Aspergillus fumigatus, Coccidiodes immitis, Paracoccidiodes brasiliensis, Blastomyces dermitidis, Pneumocystis carinii, Penicillium marneffi*, and *Alternaria alternata.*

The vectors of the disclosure are not limited to fungi, bacteria, and viruses. Also disclosed are vectors, wherein the antigen-encoding nucleic acid is an antigen from a parasite. The parasitic antigen can be selected from the group consisting of *Toxoplasma gondii, Plasmodium falciparum, Plasmodium vivax, Plasmodium malariae*, other *Plasmodium* species, *Trypanosoma brucei, Trypanosoma cruzi, Leishmania major*, other *Leishmania* species, *Schistosoma mansoni*, other *Schistosoma* species, and *Entamoeba histolytica*. The art is replete with examples of parasitic antigens whose sequences and methods of obtaining them are well known.

There are instances wherein it is advantageous to administer the vector of the disclosure in a pharmaceutical composition that comprises other vaccines. Pharmaceutical compositions comprising multiple vaccines can be for therapeutic or prophylactic purposes. Examples of such compositions include the mumps, measles, rubella (MMR) vaccine, and vaccines against *M. tuberculosis, M. bovis, M. bovis* strain BCG, BCG substrains, *M. avium, M. intracellulare, M. africanum, M. kansasii, M. marinum, M. ulcerans, M. avium* subspecies *paratuberculosis, Nocardia asteroides*, other *Nocardia* species, *Legionella pneumophila*, other *Legionella* species, *Salmonella typhi*, other *Salmonella* species, *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Chlamydia pneumoniae, Chlamydia trachomatis, Chlamydia psittaci, Coxiella burnetti*, other *Rickettsial* species, *Ehrlichia* species, *Staphylococcus aureus, Staphylococcus epidermidis, Streptococcus pyogenes, Streptococcus agalactiae, Bacillus anthracis, Escherichia coli, Vibrio cholerae, Campylobacter* species, *Neiserria meningitidis, Neiserria gonorrhea, Pseudomonas aeruginosa*, other *Pseudomonas* species, *Haemophilus influenzae, Haemophilus ducreyi*, other *Hemophilus* species, *Clostridium tetani*, other *Clostridium* species, *Yersinia enterolitica*, and other *Yersinia* species. Specifically contemplated and disclosed are pharmaceutical compositions comprising the vector of the disclosure and one or more additional vaccines. Also disclosed are instances in which the vector comprises more than one antigen-encoding nucleic acid. In such a situation, the vector will produce each antigen encoded in the vector as a separate antigen.

There are instances in which a disclosed vector alone may not be suitable for a given purpose (e.g., a kit designed to screen potential drugs for the treatment of a condition, such kit intended for use in laboratories without the capabilities to transfect a cell-line with the vector). In such cases, cells previously transfected with the vector of the disclosure are needed. Thus, also disclosed are cells comprising the disclosed vectors.

In one embodiment, the antigen-encoding nucleic acid can encode a non-antigenic sequence of DNA. This sequence provides a functional copy of a disrupted, mutated, disregulated or deleted gene. Examples of nucleic acids encoding proteins that play a role in genetic disorders are known in the literature relating to genetic disorders. Methods of making these cells are described and exemplified herein and in the art.

The ability to detect the presence of a construct can be a desirable feature of any vector. As such, vectors often contain a marker to show that the construct of interest has been delivered to the subject (e.g., in a cell), and once delivered, is being expressed. A marker can take the form of a gene that is detectable when expressed. Thus, also disclosed are vectors further comprising a reporter gene. One example of a reporter gene is green fluorescence protein (GFP).

IV. Delivery of the Compositions to Cells

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems, such as electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., *Science*, 247, 1465-1468, (1990); and Wolff, J. A. *Nature*, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

V. Nucleic Acid Based Delivery Systems

Transfer vectors can be any nucleotide construction used to deliver genes into cells (e.g., a plasmid), or as part of a general strategy to deliver genes (e.g., as part of recombinant retrovirus or adenovirus; Ram et al. *Cancer Res.* 53:83-88, (1993)).

As used herein, plasmid or viral vectors are agents that transport nucleic acids into the cell without degradation, and include a promoter yielding expression of the gene in the cells into which it is delivered. In some embodiments the vectors are derived from either a virus or specifically a retrovirus. Viral vectors can include for example, for example, HTLV-1, HTLV-2, HTLV-3, HTLV-4, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload (e.g., a transgene or marker gene) than other viral vectors, and for this reason are commonly used vectors. However, they are not as useful in non-proliferating cells. Adenovirus vectors are relatively stable and easy to work with, have high titers, can be delivered in aerosol formulation, and can transfect non-dividing cells. Pox viral vectors are large, have several sites for inserting genes, are thermostable, and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

VI. Retroviral Vectors

Primate T-lymphotropic viruses are retroviruses. A retrovirus is an animal virus belonging to the virus family of Retroviridae, including any types, subfamilies, genus, or tropisms. Retroviral vectors, in general, are described by Verma, I. M., Retroviral vectors for gene transfer, In *Microbiology-1985*, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (*Science* 260:926-932 (1993)); the teachings of which are incorporated herein by reference. Although the present primate T-lymphotropic virus vector is unique, the methods described for using other types of viral vectors can be useful in certain contexts. See for example U.S. Pat. No. 5,646,032, which is incorporated herein for its teaching of those methods.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome contains the gag, pol, and env genes which are involved in the making of the protein coat. It is the gag, pol, and env genes which are typically replaced by the foreign DNA that is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serves as the priming site for the synthesis of the second strand of DNA synthesis, and specific sequences near the ends of the LTRs that enable the insertion of the DNA state of the retrovirus to insert into the host genome. The removal of the gag, pol, and env genes allows for large fragments of foreign sequence to be inserted into the viral genome, become reverse transcribed, and upon replication, be packaged into a new retroviral particle. This amount of nucleic acid is sufficient for the delivery of many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

It is also understood that the pX region can be used to construct a vector. The pX region is located between the end of env and the beginning of Tax and contains small ORFs, hence this is another good region for insertion of foreign DNA in an HTLV genome based vector.

Disclosed are methods of detecting the expression of the disclosed vectors comprising using a first antibody to the antigen to measure protein expression in a quantitative or qualitative way, and further comprising detecting the first antibody directly via a colorimetric measurement produced through the use of a substrate and a conjugated antibody or indirectly via a first antibody to the antigen, which in turn is bound by a second antibody that is conjugated and will result in a colorimetric measurement when combined with a substrate.

Also disclosed are methods wherein the antigen is detected by placing an aliquot of the disclosed vector in a lane on a gel and probing the gel for the antigen.

Some methods are methods of detecting the expression of the disclosed vector using a fluorescently labeled first antibody specific for the antigen and visualizing the antigen using a flow cytometer, fluorescence microscope, or chemiluminescence. In some embodiments, the first antibody is not fluorescently labeled, but a target for a second antibody with a fluorescent label.

Also disclosed are methods of detecting the expression of a disclosed vector comprising using cytolytic killing assay to assess activity, and methods of detecting the vector that further include obtaining a sample from a subject comprising a tissue biopsy or removal of blood or bone marrow.

VII. Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro. In the methods described above which include the administration and uptake of exogenous DNA into the cells of a subject (e.g., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution or suspension (for example, incorporated into microparticles, liposomes, or cells). These may be targeted to a particular cell type via antibodies, receptors, or receptor ligands. The following references are examples of the use of this technology to target specific proteins to tumor tissue (Senter et al., *Bioconjugate Chem.* 2:447-451, (1991); Bagshawe, K. D., *Br. J. Cancer* 60:275-281 (1989); Bagshawe et al., *Br. J. Cancer* 58:700-703 (1988); Senter et al., *Bioconjugate Chem.* 4:3-9 (1993); Battelli et al., *Cancer Immunol. Immunother.* 35:421-425

(1992); Pietersz and McKenzie, *Immunolog. Reviews* 129:57-80 (1992); and Roffler et al., *Biochem. Pharmacol.* 42:2062-2065 (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research* 49:6214-6220 (1989); and Litzinger and Huang, *Biochimica et Biophysica Acta* 1104:179-187 (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10(6):399-409 (1991)).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

VIII. In Vivo/Ex Vivo Methods

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

IX. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

X. Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature*, 273:113 (1978)). The immediate early promoter of the human cytomegalovirus is conveniently obtained as a HindIII E restriction fragment (Greenway et al., *Gene* 18:355-360 (1982)). Of course, promoters from the host cell or related species also are useful herein. Such preferred promoters are in the LTRs of HTLV.

Enhancer generally refers to a sequence of DNA that functions at no fixed distance from the transcription start site and can be either 5' (Laimins et al., *Proc. Natl. Acad. Sci.* 78:993 (1981)) or 3' (Lusky et al., *Mol. Cell. Bio.* 3:1108 (1983)) to the transcription unit. Furthermore, enhancers can be within an intron (Banerji et al., *Cell* 33:729 (1983)), as well as within the coding sequence itself (Osborne et al., *Mol. Cell. Bio.* 4:1293 (1984)). They are usually between 10 and 300 by in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer may be specifically activated, for instance by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

XI. Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker is a selectable marker. Examples of suitable selectable markers for mammalian cells are dihydrofolate reductase (DHFR), thymidine kinase, neomycin, neomycin analog G418, hygromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells that have a novel gene would express a protein conveying drug resistance and would survive the selection. Examples of such dominant selection use the drugs neomycin, (Southern & Berg, *J. Molec. Appl. Genet.* 1:327 (1982)), mycophenolic acid, (Mulligan & Berg *Science* 209:1422 (1980)) or hygromycin, (Sugden et al., *Mol. Cell. Biol.* 5:410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin.

XII. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another method of calculating homology can be performed by published algorithms. Optimal alignment of sequences for comparison may be conducted by the local homology algorithm of Smith & Waterman *Adv. Appl. Math.* 2:482 (1981), by the homology alignment algorithm of Needleman & Wunsch, *J. MoL Biol.* 48:443 (1970), by the search for similarity method of Pearson & Lipman, *Proc. Natl. Acad. Sci. U.S.A.* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker *Science* 244:48-52, 1989, Jaeger et al. *Proc. Natl. Acad. Sci. USA* 86:7706-7710, 1989, and Jaeger et al. *Methods Enzymol.* 183:281-306, 1989, which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith & Waterman calculation method, the Needleman & Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

XIII. Nucleic Acids

There are a variety of molecules disclosed herein that are nucleic acid based, including for example the nucleic acids that encode HTLV-3 or HTLV-4 (e.g., SEQ ID NOs: 36, 53, and 81). The disclosed nucleic acids are made up of, for example, nucleotides, nucleotide analogs, or nucleotide substitutes. Non-limiting examples of these and other molecules are discussed herein. It is understood that for example, when a vector is expressed in a cell, the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

XIV. Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate). There are many varieties of these types of molecules available in the art and available herein.

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. There are many varieties of these types of molecules available in the art and available herein.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. There are many varieties of these types of molecules available in the art and available herein.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., *Proc. Natl. Acad. Sci. USA,* 1989, 86:6553-6556). There are many varieties of these types of molecules available in the art and available herein.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

XV. Sequences

There are a variety of sequences related to the protein molecules, for example the protein coding regions gag, pol, env, tax, rex, and protease (pro) genes and noncoding regions such as the LTR of HTLV-3 and HTLV-4, or any of the nucleic acids disclosed herein for making HTLV-3 or HTLV-4, all of which are encoded by nucleic acids or are nucleic acids. The sequences for the human analogs of these genes, as well as other analogs, and alleles of these genes, and splice variants and other types of variants, are available in a variety of protein and gene databases, including GenBank. Those sequences available at the time of filing this application at GenBank are herein incorporated by reference in their entireties as well as for individual subsequences contained therein. GenBank can be accessed at www.ncbi.nih.gov/entrez/query.fcgi. Those of skill in the art understand how to resolve sequence discrepancies and differences and to adjust the compositions and methods relating to a particular sequence to other related sequences. Primers and/or probes can be designed for any given sequence given the information disclosed herein and known in the art.

XVI. Primers and Probes

Disclosed are compositions including primers and probes, which are capable of interacting with the disclosed nucleic acids, such as the HTLV-3 or HTLV-4 as disclosed herein. In certain embodiments the primers are used to support nucleic acid (DNA, RNA, etc.) amplification reactions. Thus, for example, disclosed herein are primers wherein the primer comprises SEQ ID NOs: 7 and 8, SEQ ID NOs: 11 and 12, SEQ ID NOs: 15 and 16, SEQ ID NOs: 23 and 24, SEQ ID NOs: 27 and 28, SEQ ID NOs: 31 and 32, SEQ ID NOs: 69 and 70, SEQ ID NOs: 73 and 74, SEQ ID NOs: 77 and 78, SEQ ID NOs: 9 and 10, SEQ ID NOs: 13 and 14, SEQ ID NOs: 17 and 18, SEQ ID NOs: 25 and 26, SEQ ID NOs: 29 and 30, SEQ ID NOs: 33 and 34, SEQ ID NOs: 64 and 65, SEQ ID NOs: 71 and 72, SEQ ID NOs: 75 and 76, and SEQ ID NOs: 79 and 80. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. Thus, herein are disclosed primer pairs used in conjunction with a second nested set of primers pairs. For example, disclosed herein are PCR amplification methods comprising a first primer pair and a second primer pair, wherein the second primer pair is internal to the first primer pair and wherein the first primer pair is selected from the group consisting of SEQ ID NOs: 7 and 8, SEQ ID NOs: 11 and 12, SEQ ID NOs: 15 and 16, SEQ ID NOs: 23 and 24, SEQ ID NOs: 27 and 28, SEQ ID NOs: 31 and 32, SEQ ID NOs: 69 and 70, SEQ ID NOs: 73 and 74, and SEQ ID NOs: 77 and 78, wherein the second set of primers is selected from the group consisting of SEQ ID NOs: 9 and 10, SEQ ID NOs: 13 and 14, SEQ ID NOs: 17 and 18, SEQ ID NOs: 25 and 26, SEQ ID NOs: 29 and 30, SEQ ID NOs: 33 and 34, SEQ ID NOs: 71 and 72, SEQ ID NOs: 75 and 76, and SEQ ID NOs: 79 and 80. It is understood that in certain embodiments the primers can also be extended using non-enzymatic techniques, where for example, the nucleotides or oligonucleotides used to extend the primer are modified such that they will chemically react to extend the primer in a sequence specific manner. Typically, the disclosed primers hybridize with the disclosed nucleic acids or region of the nucleic acids or they hybridize with the complement of the nucleic acids or complement of a region of the nucleic acids.

XVII. Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example; functional nucleic acids include antisense molecules, aptamers, ribozymes, triplex forming molecules, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of any of the disclosed nucleic acids, such as the pol, tax, env, gag, rex and pro genes and non-coding regions such as the LTR of HTLV-3 and HTLV-4, or the nucleic acids used for the generation of HTLV-3 and HTLV-4, or the genomic DNA of any of the disclosed viruses, such as HTLV-3 and HTLV-4, or they can interact with the polypeptide encoded by any of the disclosed nucleic acids, such as pol, tax, rex, env, gag, or pro genes of HTLV-3 and HTLV-4, or the nucleic acids used for the generation of pol, tax, rex, env, gag, or LTR proteins of HTLV-3 and HTLV-4. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

XVIII. Protein Variants

As discussed herein, there are numerous disclosed variants of the HTLV-3 proteins encoded herein, such as gag (SEQ ID NO: 40), pol (SEQ ID NO: 44), env (SEQ ID NO: 37), tax (SEQ ID NO: 50), rex (SEQ ID NO: 48), protease (SEQ ID NO: 46), and non-coding regions such as the LTR, and HTLV-4 proteins encoded herein, such as gag, pol (SEQ ID NO: 57), env (SEQ ID NO: 54), tax (SEQ ID NO: 62), rex (SEQ ID NO: 60), protease (SEQ ID NO: 58) and non-coding regions such as the LTR. In addition, to the known functional HTLV-3 and HTLV-4 strain variants there are derivatives of the HTLV-3 and HTLV-4 gag, pol, tax, rex, and env, LTR proteins that also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, e.g., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviation |
|---|---|
| alanine | Ala A |
| allosoleucine | AIle |
| arginine | Arg R |
| asparagine | Asn N |
| aspartic acid | Asp D |
| cysteine | Cys C |
| glutamic acid | Glu E |
| glutamine | Gln K |
| glycine | Gly G |
| histidine | His H |
| isoleucine | Ile I |
| leucine | Leu L |
| lysine | Lys K |
| phenylalanine | Phe F |
| proline | Pro P |
| pyroglutamic acid | Glu |
| serine | Ser S |
| threonine | Thr T |
| tyrosine | Tyr Y |
| tryptophan | Trp W |
| valine | Val V |

TABLE 2

Amino Acid Substitutions
Original Residue & Exemplary Conservative Substitutions
(others are known in the art)

Ala, ser
Arg, lys, gln
Asn, gln, his
Asp, glu
Cys, ser
Gln, asn, lys
Glu, asp
Gly, pro
His, asn, gln
Ile, leu, val
Leu, ile, val
Lys, arg, gln,
Met, Leu, ile
Phe, met, leu, tyr
Ser, thr
Thr, ser
Trp, tyr
Tyr, trp, phe
Val, ile, leu Substantial changes in function or immunological identity are made by selecting substitutions that are less conservative than those in Table 2, e.g., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue with another, or one polar residue with another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, *Proteins: Structure and Molecular Properties*, W.H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO: 1 sets forth a particular sequence of HTLV-3 pol protein and SEQ ID NO: 2 sets forth a particular sequence of a HTLV-4 pol protein. Specifically disclosed are variants of these and other proteins herein disclosed which have at least, 70% or 75% or 80% or 85% or 90% or 95% homology or any amount of homology in between to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2:482 (1981), by the homology alignment algorithm of Needleman and Wunsch, *J. MoL Biol.* 48:443 (1970), by the search for similarity method of Pearson and Lipman, *Proc. Natl. Acad. Sci. U.S.A.* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

It is understood that the description of conservative mutations and homology can be combined together in any combination, such as embodiments that have at least 70%, 80%, 85%, 90%, 92%, 95%, 97% or more homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, e.g. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the protein sequence set forth in SEQ ID NO: 44 is set forth in SEQ ID NO: 1. In addition, for example, disclosed are conservative derivatives of SEQ ID NO: 44.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., *Methods in Molec. Biol.* 77:43-73 (1991), Zoller, Current Opinion in Biotechnology, 3:348-354 (1992); Ibba, *Biotechnology & Genetic Engineering Reviews* 13:197-216 (1995), Cahill et al., TIBS, 14(10):400-403 (1989); Benner, TIB Tech, 12:158-163 (1994); Ibba and Hennecke, *Bio/technology,* 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—$CH$=$CH$— (cis and trans), —$COCH_2$—$CH(OH)CH_2$—, and —$CHH_2SO$—. (These and others can be found in Spatola in *Chemistry and Biochemistry of Amino Acids, Peptides, and Proteins*, B. Weinstein, eds., Marcel Dekker, New York, p. 267 (1983); Spatola, *Vega Data* (March 1983), Vol. 1, Issue 3, *Peptide Backbone Modifications* (general review); Morley, *Trends Pharm Sci* (1980) pp. 463-468; Hudson et al., *Int J Pept Prot Res* 14:177-185 (1979) (—$CH_2NH$—, $CH_2CH_2$—); Spatola et al. *Life Sci* 38:1243-1249 (1986) (—$CH\ H_2$—$S$); Hann *J. Chem. Soc Perkin Trans.* 1307-314 (1982) (—$CH$—$CH$—, cis and trans); Almquist et al. *J. Med. Chem.* 23:1392-1398 (1980) (—$COCH_2$—); Jennings-White et al. *Tetrahedron Lett* 23:2533 (1982) (—$COCH_2$—); Szelke et al. *European Appln,* EP 45665 CA (1982): 97:39405 (1982) (—$CH(OH)CH_2$—); Holladay et al. *Tetrahedron. Lett* 24:4401-4404 (1983) (—$C(OH)CH_2$—); and Hruby *Life Sci* 31:189-199 (1982) (—$CH_2$—$S$—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations (Rizo and Gierasch *Ann. Rev. Biochem.* 61:387 (1992), incorporated herein by reference).

XIX. Pharmaceutical Carriers/Delivery of Pharmaceutical Products

As described above, the compositions can be administered in vivo in a pharmaceutically acceptable carrier. By "pharmaceutically acceptable" is meant a material that is not biologically or otherwise undesirable, e.g., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter et al., *Bioconjugate Chem.* 2:447-451 (1991); Bagshawe *Br. J. Cancer* 60:275-281 (1989); Bagshawe et al., *Br. J. Cancer* 58:700-703 (1988); Senter et al., *Bioconjugate Chem.* 4:3-9 (1993); Battelli et al., *Cancer Immunol. Immunother.* 35:421-425 (1992); Pietersz and McKenzie, *Immunolog. Reviews* 129:57-80 (1992); and Roffler et al., *Biochem. Pharmacol.* 42:2062-2065 (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research* 49:6214-6220 (1989); and Litzinger and Huang, *Biochimica et Biophysica Acta* 1104:179-187 (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

XX. Pharmaceutically Acceptable Carriers

The compositions, including antibodies, can be used therapeutically in combination with a pharmaceutically acceptable carrier. Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable, depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

XXI. Therapeutic Uses

Effective dosages and schedules for administering the compositions may be determined empirically, and making such determinations is within the skill in the art. The dosage ranges for the administration of the compositions are those large enough to produce the desired therapeutic or prophylactic effect. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Following administration of a disclosed composition, such as an antibody, for treating, inhibiting, or preventing an HTLV-3 or HTLV-4 infection, the efficacy of the therapeutic antibody can be assessed in various ways well known to the skilled practitioner. For instance, one of ordinary skill in the art will understand that a composition, such as an antibody disclosed herein, is efficacious in treating or inhibiting an HTLV-3 or HTLV-4 infection in a subject by observing that the composition reduces viral load or prevents a further increase in HTLV-3 or HTLV-4 viral load. Techniques used to measure the response of HTLV-3 or HTLV-4-infected subject to treatment with an antibody include determining whether the treatment partially or completely inhibits the appearance of the virus in the blood or other body fluid.

Other molecules that interact with HTLV-3 or HLV-4 (or the proteins encoded by those virus nucleic acid sequences) can be used that do not have a specific pharmaceutical function, but which may be used for tracking changes within cellular chromosomes or for the delivery of diagnostic tools, for example can be delivered in ways similar to those described for the pharmaceutical products. The disclosed compositions and methods can also be used, for example, as tools to isolate and test new drug candidates for a variety of primate T-lymphotropic virus related diseases.

XXII. Treatment and Prevention Methods

By "treating" is meant an improvement in or abatement of the disease state (e.g., viral infection, bacterial infection, parasitic infection, cancer, genetic disorder, or autoimmune disease) is observed and/or detected upon or after administration of a substance of the present disclosure to a subject. Treatment can range from a positive change in a symptom or symptoms of the disease to complete amelioration of the disease (e.g., viral infection, bacterial infection, parasitic infection, or cancer) (e.g., reduction in severity, intensity, or duration of disease, alteration of clinical parameters indicative of the subject's condition, relief of discomfort or increased or enhanced function), as detected by art-known techniques. The methods of the present disclosure can be utilized, for instance, to prevent or treat a viral infection, bacterial infection, parasitic infection, or cancer. One of skill in the art would recognize that this viral infection, bacterial infection, parasitic infection, or cancer can include conditions characterized by the presence of a foreign pathogen or abnormal cell growth. Clinical symptoms will depend on the particular condition and are easily recognizable by those skilled in the art of treating the specific condition. Treatment methods can include, but are not limited to therapeutic vaccinations. Thus, disclosed are methods of treating a subject with a condition comprising administering to the vector or other composition disclosed herein.

Also disclosed are methods wherein the condition being treated or prevented is a viral infection. The viral infection can be selected from the list of viruses consisting of Herpes simplex virus type-1, Herpes simplex virus type-2, Cytomegalovirus, Epstein-Barr virus, Varicella-zoster virus, Human herpesvirus 6, Human herpesvirus 7, Human herpesvirus 8, Variola virus, Vesicular stomatitis virus, Hepatitis A virus, Hepatitis B virus, Hepatitis C virus, Hepatitis D virus, Hepatitis E virus, Rhinovirus, SARS, Coronavirus, Influenza virus A, Influenza virus B, Measles virus, Polyomavirus, Human Papillomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-lymphotropic virus type-1, Human T-lymphotropic virus type-2, Primate T-lymphotropic virus, Hantavirus, Rubella virus, Simian Immunodeficiency virus, Human Immunodeficiency virus type-1, and Human Immunodeficiency virus type-2.

Also disclosed are methods wherein the condition being treated or prevented is a bacterial infection. The bacterial infection can be selected from the list of bacterium consisting of *M. tuberculosis, M. bovis, M. bovis* strain BCG, BCG substrains, *M. avium, M. intracellulare, M. africanum, M. kansasii, M. marinum, M. ulcerans, M. avium* subspecies *paratuberculosis, Nocardia asteroides*, other *Nocardia* species, *Legionella pneumophila*, other *Legionella* species, *Salmonella typhi*, other *Salmonella* species, *Shigella species, Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Chlamydia pneumoniae, Chlamydia trachomatis, Chlamydia psittaci, Coxiella burnetti*, other *Rickettsial* species, *Ehrlichia* species, *Staphylococcus aureus, Staphylococcus epidermidis, Streptococcus pyogenes, Streptococcus agalactiae, Bacillus anthracis, Escherichia coli, Vibrio cholerae, Campylobacter* species, *Neiserria meningitidis, Neiserria gonorrhea, Pseudomonas aeruginosa*, other *Pseudomonas* species, *Haemophilus influenzae, Haemophilus ducreyi*, other *Hemophilus* species, *Clostridium tetani*, other *Clostridium* species, *Yersinia enterolitica*, and other *Yersinia* species.

Also disclosed are methods wherein the antigen-encoding nucleic acid is an antigen from a bacterium. The bacterial antigen can be selected from the group consisting of *M. tuberculosis, M. bovis, M. bovis* strain BCG, BCG substrains, *M. avium, M. intracellulare, M. africanum, M. kansasii, M. marinum, M. ulcerans, M. avium* subspecies *paratuberculosis, Nocardia asteroides*, other *Nocardia* species, *Legionella pneumophila*, other *Legionella* species, *Salmonella typhi*, other *Salmonella* species, *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Chlamydia pneumoniae, Chlamydia trachomatis, Chlamydia psittaci, Coxiella burnetti*, other *Rickettsial* species, *Ehrlichia* species, *Staphylococcus aureus, Staphylococcus epidermidis, Streptococcus pyogenes, Streptococcus agalactiae, Bacillus anthracis, Escherichia coli, Vibrio cholerae, Campylobacter* species, *Neiserria meningitidis, Neiserria gonorrhea, Pseudomonas aeruginosa*, other *Pseudomonas* species, *Haemophilus influenzae, Haemophilus ducreyi*, other *Hemophilus* species, *Clostridium tetani*, other *Clostridium* species, *Yersinia enterolitica*, and other *Yersinia* species.

Also disclosed are methods wherein the condition being treated or prevented is a fungal infection. The fungal infection can be selected from the list of fungus consisting of *Candida albicans, Cryptococcus neoformans, Histoplama capsulatum, Aspergillus fumigatus, Coccidiodes immitis, Paracoccidiodes brasiliensis, Blastomyces dermitidis, Pneumocystis carinii, Penicillium marneffi*, and *Alternaria alternatas*.

Also disclosed are methods wherein the condition being treated is a parasitic infection. The parasitic infection can be selected from the list of parasites consisting of *Toxoplasma gondii, Plasmodium falciparum, Plasmodium vivax, Plasmodium malariae*, other *Plasmodium* species, *Trypanosoma brucei, Trypanosoma cruzi, Leishmania major*, other *Leishmania* species, *Schistosoma mansoni*, other *Schistosoma* species, and *Entamoeba histolytica*.

In addition, the disclosed vectors and vector containing compositions can be used to treat any disease where uncontrolled cellular proliferation occurs, such as a cancer. A non-limiting list of different types of cancers that can be treated with the disclosed compositions is as follows: lymphomas (including Hodgkin's and non-Hodgkin's, B cell lymphoma, and T cell lymphoma), mycosis fungoides, leukemias (including myeloid leukemia), carcinomas, carcinomas of solid tissues, squamous cell carcinomas, adenocarcinomas, sarcomas, gliomas, high grade gliomas, bladder cancer, brain cancer, nervous system cancer, head and neck cancer, blastomas, neuroblastomas, plasmacytomas, histiocytomas, melanomas, adenomas, hypoxic tumors, myelomas, AIDS-related lymphomas or sarcomas, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, large bowel cancer, hematopoietic cancers; testicular cancer; colon and rectal cancers, prostatic cancer, or pancreatic cancer, cervical cancer, cervical carcinoma, breast cancer, and epithelial cancer, renal cancer, genitourinary cancer, pulmonary cancer, esophageal carcinoma, metastatic cancers, or cancers in general.

Also disclosed are methods wherein the antigen-encoding nucleic acid is a tumor antigen. The tumor antigen can be selected from the list consisting of human epithelial cell mucin (Muc-1; a 20 amino acid core repeat for Muc-1 glycoprotein, present on breast cancer cells and pancreatic cancer cells), the Ha-ras oncogene product, p53, carcino-embryonic antigen (CEA), the raf oncogene product, gp100/pmel17, GD2, GD3, GM2, TF, sTn, MAGE-1, MAGE-3, BAGE, GAGE, tyrosinase, gp75, Melan-A/Mart-1, gp100, HER2/neu, EBV-LMP 1 & 2, HPV-F4, 6, 7, prostate-specific antigen (PSA), HPV-16, MUM, alpha-fetoprotein (AFP), CO17-1A, GA733, gp72, p53, the ras oncogene product, HPV E7, Wilm's tumor antigen-1, telomerase, and melanoma gangliosides.

Disclosed are methods of treating a condition in a subject comprising administering to the subject the vector of the disclosure, wherein the condition is due to a mutated, disregulated, disrupted, or deleted gene; autoimmunity; or inflammatory diseases, including but not limited to cystic fibrosis, asthma, multiple sclerosis, muscular dystrophy, diabetes, tay-sachs, spinobifida, cerebral palsy, Parkinson's disease, Lou Gehrig's disease, Alzheimer's, systemic lupus erythematosis, hemophilia, Addison's disease, Cushing's disease.

By "preventing" is meant that after administration of a substance of the present disclosure to a subject, the subject does not develop the symptoms of the viral, bacterial, or parasitic infection, and/or does not develop the viral, bacterial, or parasitic infection. "Preventing" or "prevention" can also refer to the ultimate reduction of an infection, condition, or symptoms of an infection, or condition relative to infections or conditions in subjects that do not receive the substance. Methods of prevention can include, but are not limited to prophylactic vaccination. As such, disclosed are methods of preventing an infection in a subject comprising administering to the subject the vector of the disclosure.

Also disclosed are methods of the disclosure, wherein the infection prevented is a fungal infection or the antigen-encoding nucleic acid is an antigen from a fungus. The fungal infection or antigen can be selected from the list of *Candida albicans, Cryptococcus neoformans, Histoplama capsulatum, Aspergillus fumigatus, Coccidiodes immitis, Paracoccidiodes brasiliensis, Blastomyces dermitidis, Pneumocystis carinii, Penicillium marneffi*, and *Alternaria alternata*.

Also disclosed are methods of the disclosure, wherein the antigen-encoding nucleic acid is an antigen from a parasite. The parasitic antigen can be selected from the group consisting of *Toxoplasma gondii, Plasmodium falciparum, Plasmodium vivax, Plasmodium malariae*, other *Plasmodium* species, *Trypanosoma brucei, Trypanosoma cruzi, Leishmania major*, other *Leishmania* species, *Schistosoma mansoni*, other *Schistosoma* species, and *Entamoeba histolytica*.

Also disclosed are methods of the disclosure, wherein the subject is a horse, cow, pig, dog, car, mouse, monkey, human, or a cell isolated from such an animal.

XXIII. Screening Methods

Disclosed herein are methods of identifying new primate T-lymphotropic viruses comprising: a) contacting a nucleic acid using a first set of primers and a second set of primers internal to the first set of primers, wherein the first set of primers is SEQ ID NOs: 19 and 20, and wherein the second set of primers is SEQ ID NOs: 21 and 22 under conditions that permit primer extension; b) identifying any amplified nucleic acid; and c) comparing the sequence to known primate T-lymphotropic viral sequences, wherein a sequence divergence greater than 5% indicates a new virus.

Also disclosed are methods of identifying new primate T-lymphotropic viruses comprising: a) contacting a nucleic acid using a first set of primers and a second set of primers internal to the first set of primers, wherein the first set of primers is selected from the group of primers pairs consisting of SEQ ID NOs: 7 and 8, SEQ ID NOs: 11 and 12, SEQ ID NOs: 15 and 16, SEQ ID NOs: 23 and 24, SEQ ID NOs: 27 and 28, SEQ ID NOs: 31 and 32, SEQ ID NOs: 69 and 70, SEQ ID NOs: 73 and 74, and SEQ ID NOs: 77 and 78, wherein the second set of primers is selected from the group consisting of SEQ ID NOs: 9 and 10, SEQ ID NOs: 13 and 14, SEQ ID NOs: 17 and 18, SEQ ID NOs: 25 and 26, SEQ ID NOs: 29 and 30, SEQ ID NOs: 33 and 34, SEQ ID NOs: 71 and 72, SEQ ID NOs: 75 and 76, and SEQ ID NOs: 79 and 80; b) identifying any amplified nucleic acid; and c) comparing the sequence to known primate T-lymphotropic viral sequences, wherein sequence divergence greater than 5% indicates a new virus.

It is also understood that the disclosed methods of identifying a new primate T-lymphotrophic virus can be achieved using non-nested PCR techniques such as real-time PCR. Thus, for example, specifically disclosed are methods of identifying new primate T-lymphotropic viruses comprising a) contacting a nucleic acid using a set of primers, wherein the set of primers is selected from the set of primers consisting of SEQ ID NOs: 19 and 20, SEQ ID NOs: 21 and 22, SEQ ID NOs: 7 and 8, SEQ ID NOs: 11 and 12, SEQ ID NOs: 15 and 16, SEQ ID NOs: 23 and 24, SEQ ID NOs: 27 and 28, SEQ ID NOs: 31 and 32, SEQ ID NOs: 69 and 70, SEQ ID NOs: 73 and 74, SEQ ID NOs: 77 and 78, SEQ ID NOs: 9 and 10, SEQ ID NOs: 13 and 14, SEQ ID NOs: 17 and 18, SEQ ID NOs: 25 and 26, SEQ ID NOs: 29 and 30, SEQ ID NOs: 33 and 34, SEQ ID NOs: 71 and 72, SEQ ID NOs: 75 and 76, SEQ ID NOs: 79 and 80, and SEQ ID NOs: 64 and 65; b) identifying any amplified nucleic acid; and c) comparing the sequence to known primate T-lymphotropic viral sequences, wherein sequence divergence greater than 5% indicates a new virus. Also disclosed are identification methods wherein the method is a real-time PCR method.

Furthermore, the disclosed methods can be used in conjunction with probes to detect the presence of amplification product. Specifically disclosed are fluorescently labeled probes that can be used to detect the amplification product of the disclosed methods. For example, a fluorescent probe, can comprise TTCCCCAAGGCTTCAAAAACAGC-CCCACGC (SEQ ID NO: 66).

The surface antigen (SU) and transmembrane regions of env can be used serologically for the identification and differentiation of PTLVs (the type specific peptides MTA-1 and K55 are in SU; likewise the p24 region of gag can be used for the serological identification of PTLV). Thus, disclosed herein are methods of identifying a PTLV comprising contacting a nucleic acid with a set of primers specific for the surface antigen or transmembrane regions of env and indentifying any amplified nucleic acid.

In addition, the disclosed peptides, polypeptides, proteins and protein fragments can be used to generate antibodies that can be used to identify new and known primate T-lymphotropic viruses. Specifically disclosed are methods of identifying the presence of a primate T-lymphotropic virus in a subject comprising taking a tissue sample from the subject and contacting the sample with an antibody directed to an HTLV-3 or HTLV-4 peptide, polypeptide, protein, or protein fragment, wherein the peptide, polypeptide, protein, or protein fragment can be SEQ ID NO: 37, 38, 39, 40, 41, 42, 43, 44, 46, 48, 50, 54, 55, 56, 57, 58, 60, 62, 67, or 68, or the polypeptide, protein, or protein fragment encoded by the nucleic acid of SEQ ID NO: 1, 2, 3, 4, 5, 6, 35, 36, 45, 47, 49, 51, 52, 53, 59, 61, 63, or 81, and wherein binding of the antibody to the sample indicates the presence of a new or known primate T-lymphotropic virus. The disclosed methods also can be used to identify new primate T-lymphotropic viruses as well as detect all primate T-lymphotropic viruses or a group of particular primate T-lymphotropic viruses. Those of skill in the art will know which antibodies to use to accomplish their detection goal. For example, to detect more than one of the known HTLV viruses (HTLV-1, 2, and 3, or HTLV-1, 2, and 4) one can use type specific peptide of HTLV-1 and HTLV-2 such as SEQ ID NO: 67 and 68.

Also provided is a method of screening a substance for effectiveness in treating or reducing the severity of the condition (e.g., HTLV-3 or HTLV-4 infection) comprising: a) obtaining an animal having the condition or characteristic (e.g., symptom) of the condition; b) administering the substance to an animal having one or more characteristics of the condition; and assaying the animal for an effect on the condition, thereby identifying a substance effective in reducing the condition. The ability of a substance to reduce the severity of a condition can be determined by evaluating the histological and/or clinical manifestations of the condition before and after administration of the substance of interest, and quantitating the degree of reduction of the histological and/or clinical manifestations of the condition. The animal in which the condition or characteristic (e.g., symptom) of the condition is produced can be any mammal, and can include but is not limited to mouse, rat, guinea pig, hamster, rabbit, cat, dog, goat, monkey, and chimpanzee. The condition or characteristic (e.g., symptom) of the condition can be produced in the animal by any method known in the art. For example, HTLV-3 or HTLV-4 can be produced by introducing into the animal (e.g., a chimpanzee infected with HTLV-3 or HTLV-4 or rhesus macaques or nemestrina macaques infected with an HTLV-3 or HTLV-4 env on an SIV backbone. Pullium et al., *J. Infectious Dis*. 183:1023, 2001) an infectious amount of HTLV-3 or HTLV-4.

The present disclosure also provides a method of screening for a substance effective in preventing the condition (e.g., HTLV-3 or HTLV-4 infection) comprising: a) administering the substance to an animal susceptible to the condition; b) subjecting the animal to treatment that will induce the condition or characteristic (e.g., symptom) of the condition; and c) assaying cells from the animal for a change in immune responses as compared to the immune responses in a control animal having the condition in the absence of the substance, identifies a substance that is effective in preventing the condition.

Also provided is a model for use in screening for substances effective in treating or preventing a disease comprising an animal capable of manifesting a characteristic of the disease, wherein the animal has been administered the vector of the disclosure.

Further embodiments are methods of making a model of HTLV-3 or HTLV-4 infection, comprising obtaining an animal capable of manifesting a characteristic of the disease, and administering to said animal one of the vectors disclosed herein that encodes an antigen associated with the disease. Also disclosed is a method of screening for a substance effective in treating a disease associated with an immunizing construct, the method comprising: a) administering the substance to the model of the disclosure; and b) assaying for a change in the course of the disease as compared to the course of the disease in a control subject. An improvement in the course of the disease in the presence of the substance identifies a substance that is effective in treating the disease.

Still other embodiments are methods of screening for a substance effective in preventing a disease associated with an immunizing construct, the method comprising: a) administering one of the vectors disclosed herein to a subject; b) subjecting the subject to treatment that will induce the disease or characteristic (e.g., symptom) of the disease; and c) assaying for a change in the course of the disease as compared to the course of the disease in a control subject. An improvement in the course of the disease in the presence of the substance identifies a substance that is effective in preventing the disease.

Yet still other embodiments are methods of screening for a substance effective in treating a disease associated with an immunizing construct, the methods comprising: a) subjecting a subject to treatment that induces the disease or characteristic (e.g., symptom) of the disease; b) administering to the subject one of the vectors disclosed herein; and c) assaying for a change in the course of the disease as compared to the course of the disease in a control subject. An improvement in the course of the disease in the presence of the substance identifies a substance that is effective in treating the disease.

XXIV. Methods of Using the Disclosed Compositions as Research Tools

The disclosed compositions can also be as used diagnostic tools related to primate T-lymphotropic diseases such as HTLV-3 and HTLV-4.

XXV. Methods of Making the Compositions

The compositions disclosed herein and the compositions necessary to perform the disclosed methods can be made using any method known to those of skill in the art for that particular reagent or compound unless otherwise specifically noted.

XXVI. Processes for Making the Compositions

Disclosed are processes for making the disclosed compositions as well as making the intermediates leading to the compositions. For example, disclosed are nucleic acids in SEQ ID NOs: 1-6, 35, 36, 45, 53, and 81. There are a variety of methods that can be used for making these compositions, such as synthetic chemical methods and standard molecular biology methods.

In some embodiments, a nucleic acid molecule is produced by the process of linking in an operative way a nucleic acid comprising the sequence set forth in SEQ ID NOs: 1-6, 35, and 45 and a sequence controlling the expression of the nucleic acid. In certain examples, the nucleic acid molecule is produced by linking in an operative way a nucleic acid molecule comprising a sequence having 80% identity to a sequence set forth in SEQ ID NOs: 1-6, 35, and 45, and a sequence controlling the expression of the nucleic acid. In other embodiments, the nucleic acid molecule is produced by linking in an operative way a nucleic acid molecule comprising a sequence that hybridizes under stringent hybridization conditions to a sequence set forth SEQ ID NOs: 1-6, 35, and 45 and a sequence controlling the expression of the nucleic acid.

In other embodiments, a transformed cell is produced by transforming the cell with any of the nucleic acids disclosed herein, for example, any of the non-naturally occurring nucleic acids disclosed herein. In still other embodiments the peptides disclosed herein are produced by expressing any of the disclosed nucleic acids.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

To determine whether HTLVs are present among individuals exposed to the blood and body fluids of wild primate populations (Wolfe et al. 2004a) known to be infected with STLV (Courgnaud et al. 2004), individuals were examined from twelve villages in southern Cameroon proximal to both forested and non-forested NHP habitats. Individuals were asked to identify and quantify their exposure to NHPs, which were organized according to three categories reliably distinguished by this population: chimpanzee, gorilla and monkey (Wolfe et al. 2004a). A total of 930 who reported exposure to NHP blood and body fluids, mainly through hunting and butchering were selected for further analysis. Plasma specimens from exposed people were screened for PTLVs using an HTLV-1/2 EIA (ELISA Immunoassay) capable of detecting antibodies to a broad range of PTLVs, followed by confirmation with an HTLV Western blot (WB) assay that can distinguish HTLV-1 and HTLV-2 (van Dooren et al. 2004). A total of 97 (10.4%) persons were EIA reactive of which 90 (9.7%) were also reactive in the WB assay. A broad range of WB profiles were seen, including HTLV-1-like (1.1%), HTLV-2-like (0.5%), HTLV-positive but untypeable (1.4%), and HTLV indeterminate (6.7%).

Figure 1:
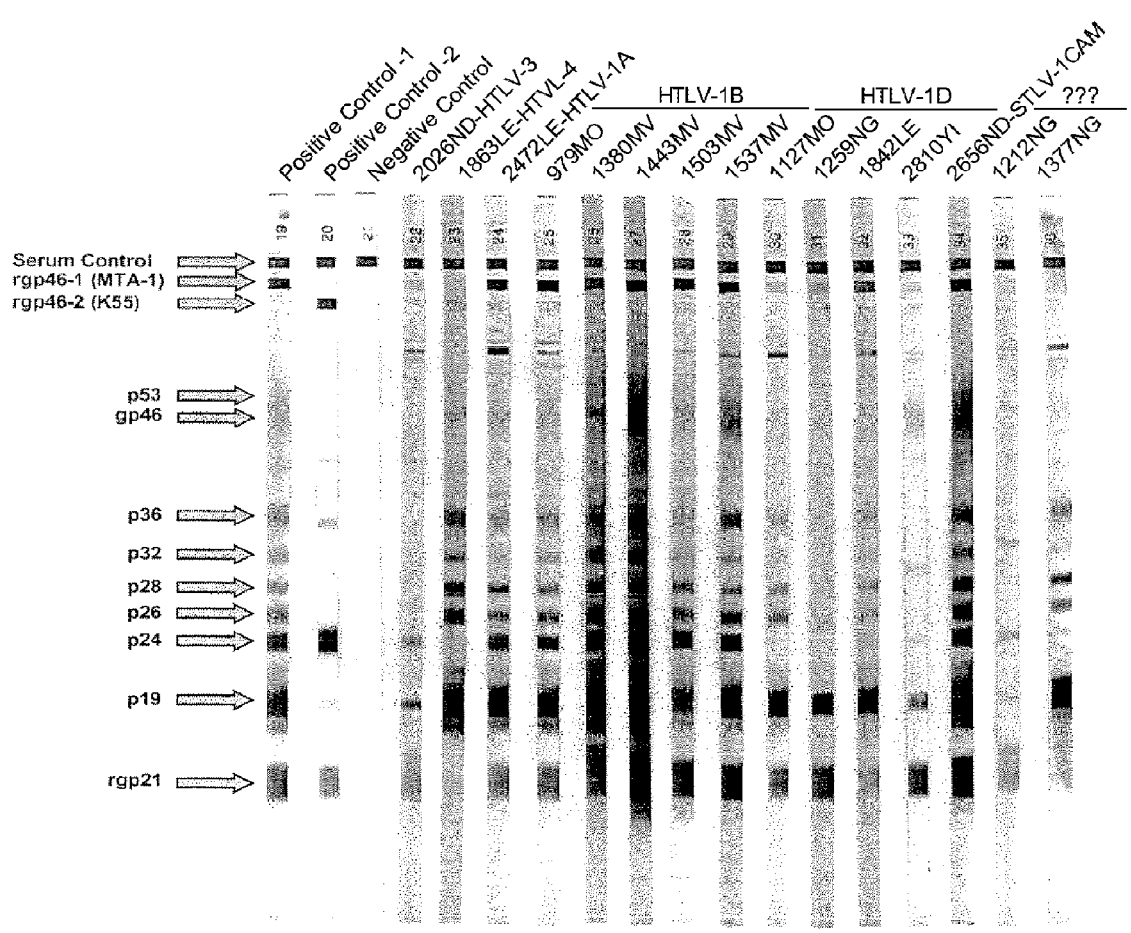
FIG. 1 is a digital image showing the Western blot serological pattern of Human T-cell lymphotropic virus (HTLV) infected African hunters. HTLV classification based on phylogenetic analyses is provided above specimen names. Reactivity to HTLV-specific proteins is indicated on left.

DNA from peripheral blood mononuclear cells (PBMCs) available from 86 of the 90 WB reactive samples were then subjected to PCR amplification of several viral regions. Viral sequences from 13 persons were obtained using this strategy. The WB reactivities of these 13 persons is shown in FIG. 1 and included HTLV-1-like (n=9), HTLV-2-like (n=1), and HTLV indeterminate (n=3) profiles. All 13 HTLV-infected persons were exclusively from lowland forest sites, including both men and women who often reported multiple opportunities for contact with the blood and body fluids of NHPs (Table 3). Since PTLV diversity is influenced more by geography than by primate species (Salemi et al 1999, Slattery et al. 1999, Gessain & Mahieux 2000), viral sequences were analyzed phylogenetically along with African and global representatives of HTLV and STLV.

TABLE 3

Nonhuman primate exposures for human T-lymphotropic virus (HTLV)-infected central African hunters

| ID | Site | HTLV | Nearest PTLV | Sex | Age | Hunting Technique | Hunt m | c | g | Butcher m | c | g | Pet m | c | g | Reported Injuries |
|---|---|---|---|---|---|---|---|---|---|---|---|---|---|---|---|---|
| 1842 | LE | HTLV-1 | Group D - Mandrill clade | m | 32 | | | | | x | | | | | | |
| 1863 | LE | HTLV-4 | Distinct from all major PTLV groups | m | 48 | S | x | x | x | | | | | | | bitten/scratched by wild animal |
| 2472 | LE | HTLV-1 | Group A Cosmopolitan | f | 27 | | | | | x | | | | | | |
| 979 | MO | HTLV-1 | Group B- Central African | m | 30 | G | x | | | x | | | | | | monkey bite |
| 1127 | MO | HTLV-1 | Group D - Mandrill clade | m | 44 | g, s | x | | | x | x | x | | | | |
| 1380 | MV | HTLV-1 | Group B- Central African | f | 55 | | | | | x | x | x | | | | |
| 1443 | MV | HTLV-1 | Group B- Central African | f | 71 | | | | | x | x | x | | | | |
| 1503 | MV | HTLV-1 | Group B- Central African | f | 75 | | | | | x | x | x | | | | |
| 1537 | MV | HTLV-1 | Group B- Central African | m | 39 | g, s | x | | | x | | | | | | wild animal injured finger |
| 2026 | ND | HTLV-3 | STLV-3 | m | 63 | S | x | | | x | | | | | | |
| 2656 | ND | HTLV-1 | Group G - Central West Africa | m | 65 | G | x | | | x | | | x | | | |
| 1259 | NG | HTLV-1 | Group D - Mandrill clade | m | 71 | g, s | x | x | | | | | | | | bitten/scratched by wild animal |
| 2810 | YI | HTLV-1 | Group G - Central West Africa | m | 55 | S | x | | | x | | | | | | |

*, m = monkey, c = chimpanzee, g = gorilla.
†, PTLV, primate T lymphotropic virus; STLV, simian T-lymphotropic virus

TABLE 4

Nucleotide and Amino Acid Percent Identities[1]

|  | HTLV-1 (ATK) | HTLV-2 (MoT) | STLV-2 (PP1664) | STLV-3 (TGE2117) | HTLV-3 (2026ND) |
|---|---|---|---|---|---|
| HTLV-3$_{2026ND}$ | | | | | |
| Genome (8917-bp) | 61.6 | 62.9 | 62.6 | 87.0 | — |
| LTR(697-bp) | 48.7 | 43.7 | 41.4 | 86.7 | — |
| gag (1268-bp) | 69.3 (83.2) | 69.4 (80.5) | 70.6 (80.7) | 87.5 (96.0) | — |
| pro (534-bp) | 59.7 (62.6) | 59.2 (66.7) | 59.4 (59.3) | 84.3 (88.1) | — |
| pol (2670-bp) | 62.2 (66.2) | 63.9 (71.2) | 63.5 (69.9) | 86.2 (93.1) | — |
| env (1476-bp) | 65.9 (73.8) | 69.0 (78.2) | 67.1 (77.4) | 87.8 (95.7) | — |
| tax (1053-bp) | 76.3 (81.4) | 75.1 (83.4) | 74.4 (80.4) | 91.2 (97.4) | — |
| rex (549-bp) | 76.9 (61.9) | 76.3 (60.6) | 75.8 (63.5) | 87.6 (89.6) | — |
| pX (699-bp) | 43.3 | 50.5 | 49.8 | 85.6 | — |
| HTLV-4$_{1863LE}$ | | | | | |
| Genome (5320-bp) | 64.0 | 72.2 | 71.4 | 66.2 | 66.1 |
| pro (273-bp)[2] | 71.4 (55.6) | 79.5 (28.1) | 79.5 (36.0) | 71.8 (29.2) | 73.3 (31.7) |
| pol (2549-bp)[2] | 63.6 (68.7) | 71.4 (80.1) | 71.0 (79.7) | 65.2 (71.7) | 64.8 (71.6) |
| env (1458-bp) | 65.8 (75.9) | 73.1 (85.3) | 72.0 (85.5) | 67.2 (78.8) | 68.5 (79.4) |
| tax (765-bp)[2] | 77.4 (85.1) | 81.7 (92.6) | 79.4 (92.9) | 75.2 (86.7) | 75.0 (86.3) |
| rex (512-bp) | 76.0 (63.9) | 79.5 (74.1) | 80.7 (68.8) | 72.5 (57.7) | 72.7 (59.4) |
| pX (559-bp) | 46.1 | 60.8 | 59.9 | 53.6 | 51.3 |

[1]Amino acid identiities are in parentheses.
[2]Only partial sequences are available Most notable of the findings was the discovery of a human virus that is distinct from all known PTLV lineages with 26-34% and 18-25% nucleotide divergence in the conserved pol and tax genes, respectively, a range of nucleotide divergence similar to that seen between HTLV-1, HTLV-2, and STLV-3 (Meertens et al. 2002; Table 4). This virus formed a separate phylogenetic lineage with a long branch length and significant bootstrap support in both the pol (FIG. 2a: pol tree) and tax trees. Phylogenetic analyses combined with GenBank blast searches show that this is the only known virus in this novel group. For these reasons this virus, which is designated HTLV-4, qualifies as the first member of a novel species in the deltaretrovirus genus. Following ICTV guidelines (van Regenmortel 2000) and pending formal classification, it is proposed that primate T-lymphotropic virus 4 (PTLV-4) be the name for this species, with PTLV-4(1863LE) as the prototype strain. HTLV-4 was found in a 48 year old male hunter (1863LE) from the southern forests of Cameroon who had an HTLV-2-like WB result and reported hunting monkeys, chimpanzees, and gorillas, and also being bitten and scratched by a wild animal, although the animal causing the injury was not specified.

Figure 2A:
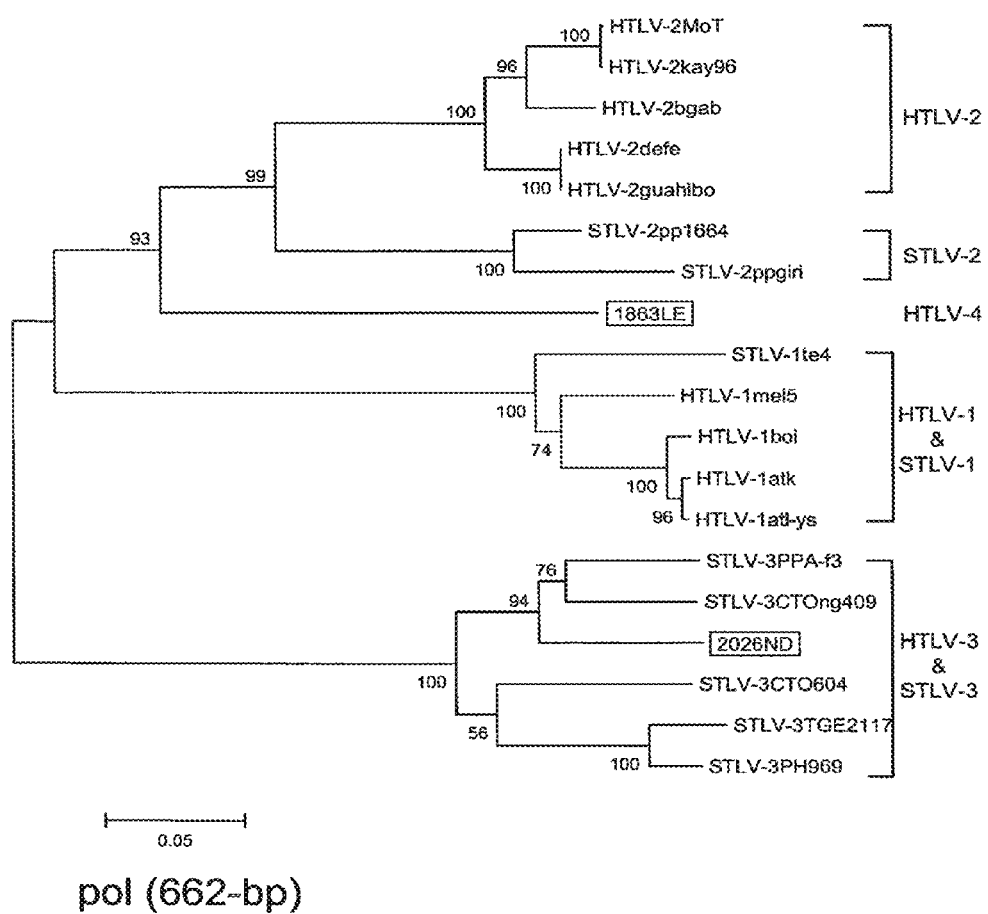
FIG. 2 shows the phylogenetic relationships of (a) primate T-cell lymphotropic virus polymerase (a) PTLV pol (662-bp), (b) PTLV env (297-bp), (c) PTLV tax (730-bp), (d) PTLV-3 long terminal repeat (LTR) (398-bp), and (e) PTLV pol-env-tax region (5258-bp) sequences by neighbor joining analysis. Sequences generated in the current study are noted with boxes. Nonhuman primate taxon codes are provided in the Methods portion of the Examples section of the specification. Support for the branching order was determined by 1,000 bootstrap replicates, and only values 60% or greater are shown. Branch lengths are proportional to the evolutionary distance (scale bar) between the taxa.
Figure 2B:
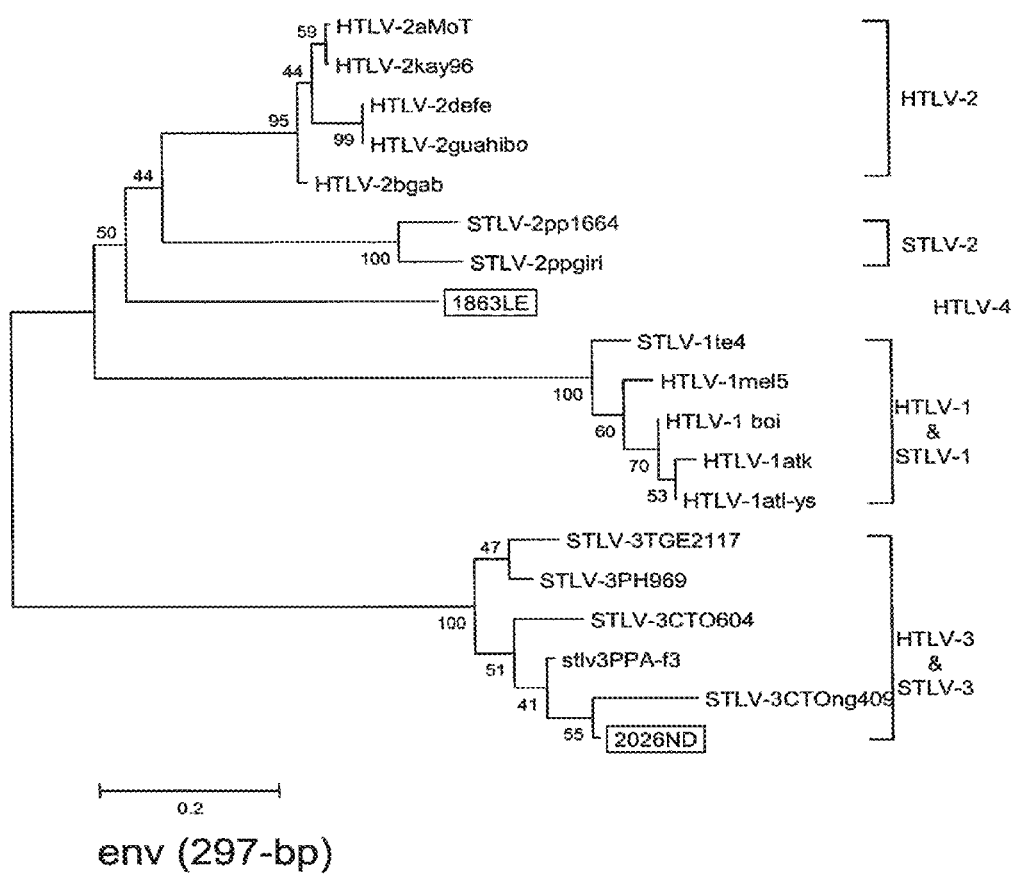
Figure 2C:
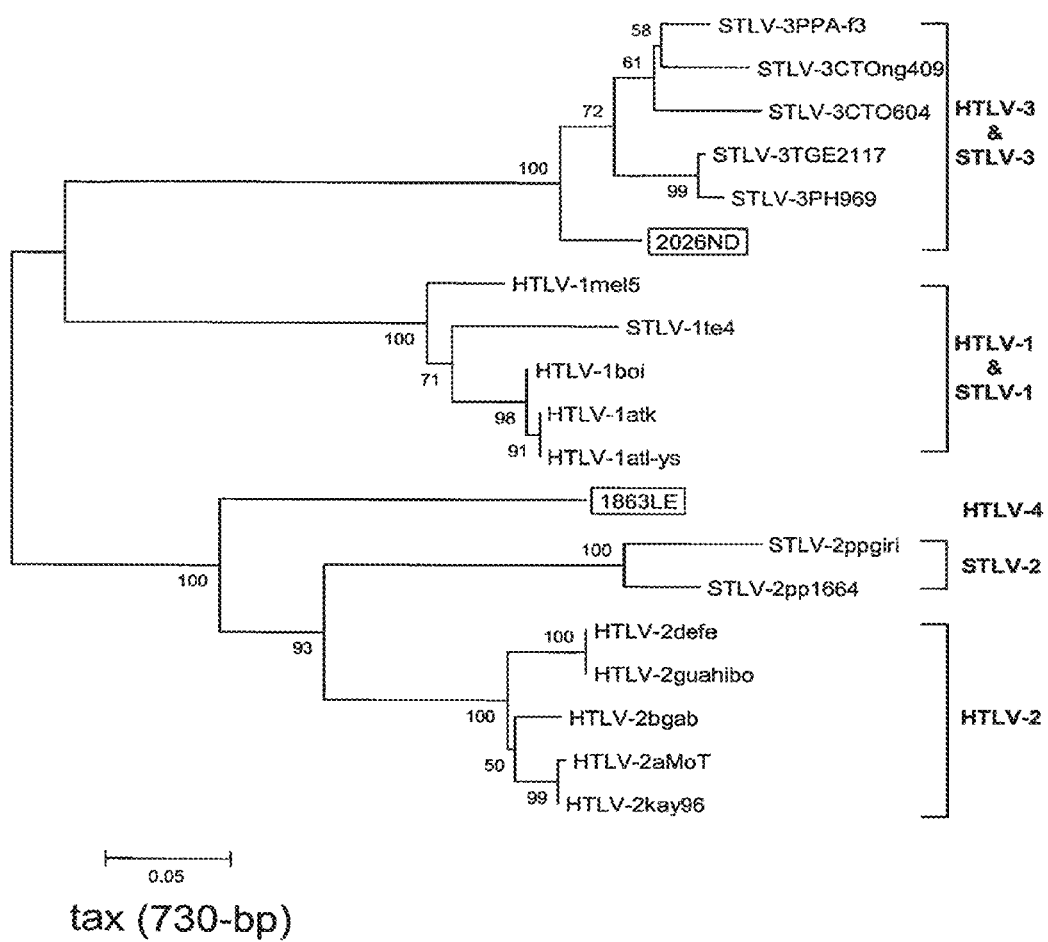
Figure 2D:
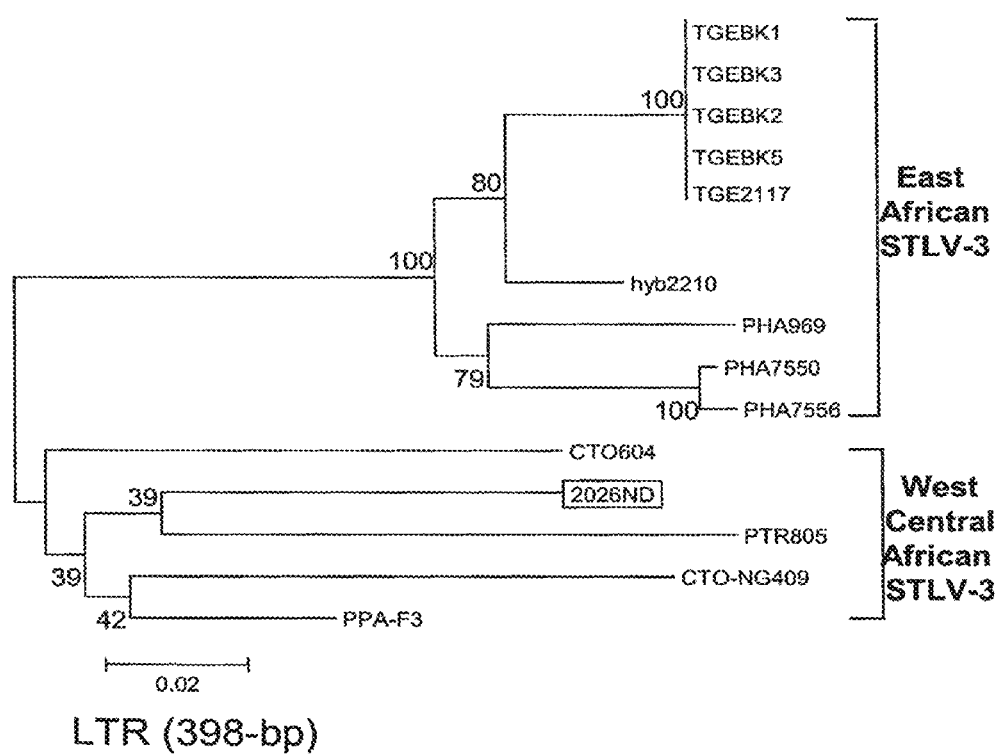
Figure 2E:
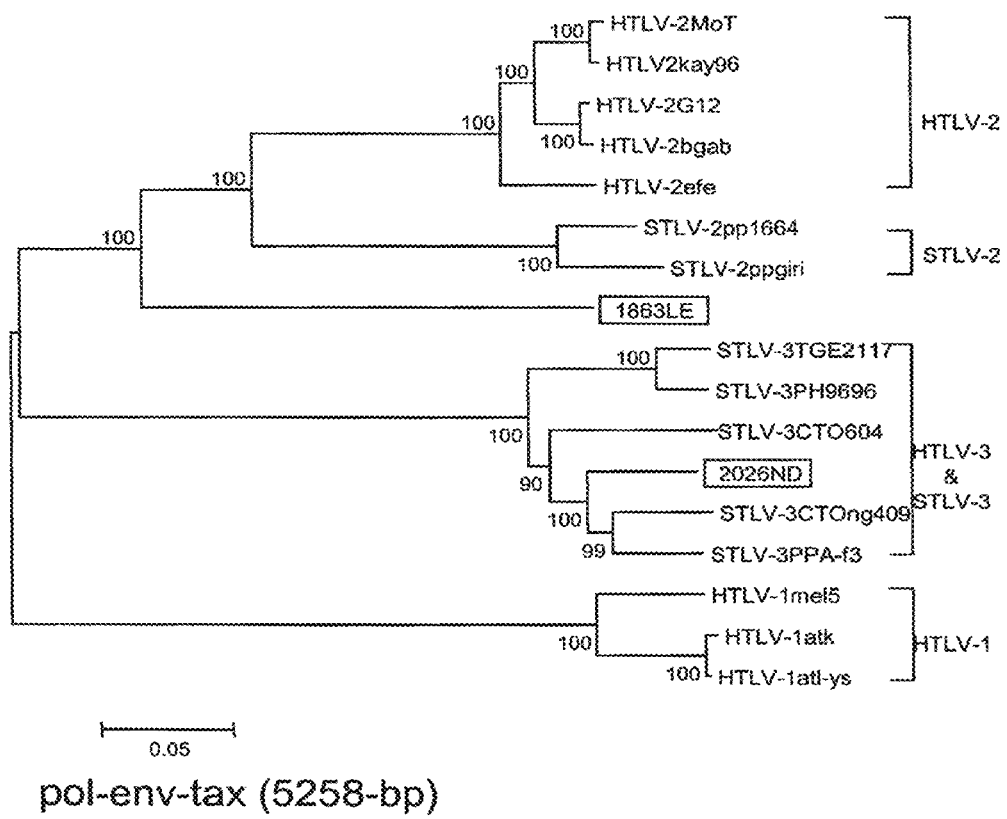

Also documented, with significant phylogenetic bootstrap support, is the first evidence of human infection within the PTLV-3 group (FIG. 2a: pol tree). This virus, which is designated HTLV-3, clusters with STLV-3 viruses present in West African NHPs as expected (FIG. 2d: LTR tree). HTLV-3 was found in a 63 year old male (2026ND) from the southern forests of Cameroon who had an HTLV-1-like WB result and who reported hunting and butchering of monkeys. The fact that this virus falls within the diversity of a group of STLVs first identified in 1994 (Goubau et al 1994) without evidence of a human counterpart to date, indicates that this infection was most likely acquired zoonotically through exposure to the blood or body fluids of a hunted NHP from this region (Courgnaud et al. 2004).

Figure 3:
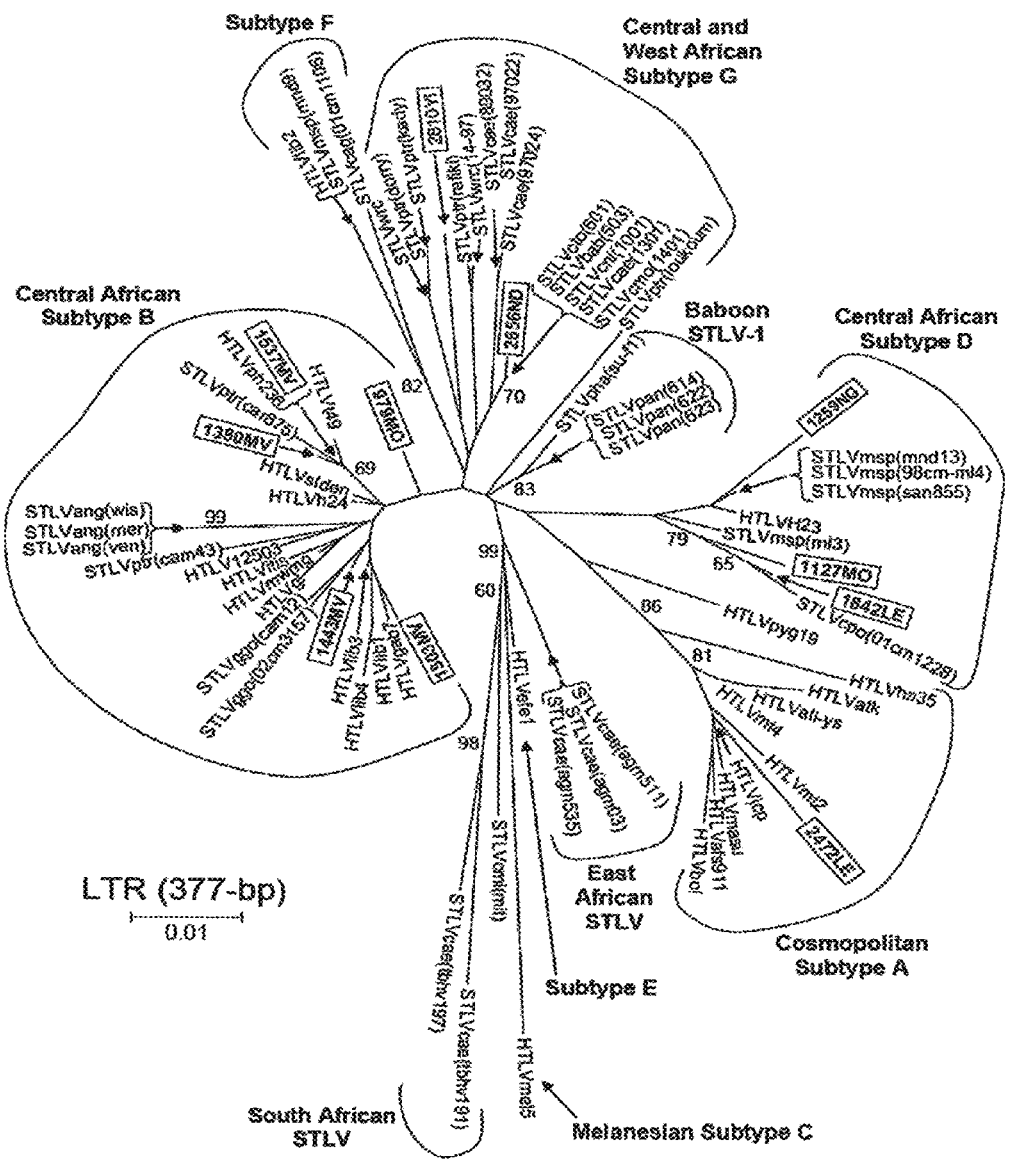
FIG. 3 shows the phylogenetic relationships of PTLV type 1 LTR (377-bp) sequences by neighbour joining analysis. Sequences generated in the current study are noted with boxes. Nonhuman primate taxon codes are provided in the Methods portion of the Examples section of the specification. Support for the branching order was determined by 1,000 bootstrap replicates and only values 60% or greater are shown. Branch lengths are proportional to the evolutionary distance (scale bar) between the taxa.

In addition, broad diversity of HTLV-1 viruses was also found in this collection. Of the 11 HTLV-1 sequences, two did not fall within any of the known HTLV-1 subtypes but clustered clearly within a clade that included only STLV-1 from central and west Africa (FIG. 2d: LTR tree). One of these viruses clustered with STLV-1 from monkeys in Cameroon and was from a 65 year-old male (2656ND) from the southern forest zone of Cameroon. He reported hunting and butchering of monkeys and kept a gorilla as a pet (Table 3). The second virus clustered with STLV-1 recently identified in chimpanzees and red colobus monkeys (Leendertz et al. 2004) and was from a 55 year old male (2810YI) who reported hunting and butchering of monkeys (Table 3). The presence of these viruses in hunters, seen previously only among NHPs, indicates that these persons were infected zoonotically. This distinct clade is referred to as HTLV-1 subtype G. Three subjects (1259NG, 1127MO, 1842LE) from different villages were found to have HTLV-1 subtype D, viruses known to infect geographically overlapping populations of humans and mandrills in central Africa (FIG. 3 LTR tree (Mahieux et al. 1998). Two of the three viruses were found in hunters (Table 3), providing indirect evidence of cross-species transmission between humans and mandrills within subtype D and supporting further the claims of cross-species transmission of this subtype (Mahieux et al. 1998). These results are consistent with SFV infection from mandrills that was documented previously in this population (Wolfe et al 2004) and indicate that the frequent hunting of mandrills may explain the widespread transmission of mandrill retroviruses. Five persons (979MO, 1380MV, 1443MV, 1503MV, 1537MV) were infected with HTLV-1 subtype B viruses, which are known to be endemic among humans in central Africa and which are believed to have originated from STLV-1 in this region (Mahieux, R. et al 1997, Gessain, A. & Mahieux, R 2000; FIG. 3: LTR tree). Thus, these five new subtype B viruses may have been acquired either zoonotically from STLV-1-infected primates or from human-to-human transmission, or both.

Notably, a 71 year old female (1443MV) who reported butchering gorillas was found to be infected with a virus most closely related to STLV-1 found in two gorillas from Cameroon (Nerrienet 2004, Courgnaud et al 2004), although without significant bootstrap support (FIG. 3 LTR). Interestingly, person 1503MV is also WB positive for SFV (Wolfe et al 2004), indicating that zoonotic transmission in an individual is not limited to a single retrovirus and providing a biological setting for viral recombination and altered pathogenicity and transmissibility of these viruses. One person (2472LE) was infected with the HTLV-1 subtype A virus, a clade consisting of sequences from only globally disseminated HTLV-1 and thus this infection was most likely acquired through humanto-human transmission. DNA samples from the remaining 73 persons with reactive WB results were all negative by the generic PCR assay for tax sequences and four other sequences specific for each PTLV clade, including HTLV-4. The results demonstrate that HTLV diversity is far greater than previously understood. The data indicate that contact with the blood and body fluids of NHPs is a major factor in the emergence of novel HTLVs, which are known to be transmissible among humans and have the potential to cause disease. Because the hunting and butchering of wild NHPs is widespread throughout central Africa (Bowen-Jones & Pendry 1999) and STLVs are known to be highly prevalent among hunted NHPs (Courgnaud et al. 2004), it is suspected that zoonotic transmission of STLV is not a restricted risk. Since blood banks in central Africa do not generally screen for HTLV, further spread of these viruses among central Africans may be facilitated by blood donations from infected persons. That HTLV-4 represents a previously unrecognized virus being transmitted between humans indicates that more substantial screening for this virus in central African populations is needed. The finding that both HTLV-4 and HTLV-3 are serologically indistinguishable from HTLV-1 and HTLV-2 in current assays can explain why these viruses have not been previously identified, and highlight the importance of improved diagnostic assays. The increasing evidence that primate hunting is associated with the emergence of a range of simian retroviruses (Wolfe et al. 2004b) calls for increased surveillance and follow-up of individuals exposed to the blood and body fluids of wild NHPs, and for effective strategies to control the hunting of NHPs.

Methods

Ethical Approvals

Studies were conducted in the context of a community-based HIV prevention campaign designed to provide information using Cameroonian educators and counselors and therefore to decrease transmission. Participation in the study was completely voluntary. The study protocol was approved by the Johns Hopkins Committee for Human Research, the Cameroon National Ethical Review Board, and the HIV Tri-Services Secondary Review Board. Questionnaires and matching samples were anonymized by removing all personal identifiers to provide an unlinked study population.

Sample Preparation and Serology

Blood was collected from participants, transported to a central laboratory, processed into plasma and PBMC aliquots and stored at −80° C. Initial screening for HTLV antibodies in serum and plasma samples was performed by using the Vironostika HTLV-1/2 microelisa system (Organon-Teknika, Durham, N.C.) following the manufacturer's instructions. Reactive samples were then tested in a WB test (HTLV Blot 2.4, Genelabs Diagnostics, Singapore) that contains disrupted HTLV-1 virions, a gp21 recombinant protein (GD21) common to both HTLV-1 and HTLV-2, and two HTLV-type specific recombinant envelope (Env) peptides, MTA-1 and K55, which allow serological differentiation of HTLV-1 and HTLV-2, respectively. Samples with reactivity to the Gag (p24) and Env (GD21) proteins were considered seropositive. Seropositive samples with reactivity to MTA-1 or K55 were considered HTLV-1-like or HTLV-2-like, respectively. Samples with reactivity to either p24 or GD21 alone or in combination with other HTLV proteins (FIG. 1) were considered indeterminate.

PCR and Sequence Analysis

DNA was prepared from uncultured PBMCs and its integrity was confirmed by β-actin PCR as previously described. All DNA preparation and PCR assays were performed in a laboratory where only human samples are processed and tested following recommended precautions to prevent contamination. DNA samples were first screened with a generic PTLV tax PCR assay capable of detecting 222-bp sequences from each of the three major PTLV groups (Busch et al. 2000, van Dooren et al. 2004). Sequence analysis of this tax sequence provided broad genetic classification into each PTLV group. Phylogenetic resolution within the PTLV-1 and PTLV-3 groups was done using LTR sequences as described previously (van Dooren et al. 2004, Meertens et al. 2001). A portion of the 3' HTLV-1 LTR from selected samples (1259NG, 1127MO, 1842LE, and 2810YI) was amplified by nested PCR using external primers 5VLTRext 5' AACCAC-CCATTTCCTCCCCATG 3' (SEQ ID NO: 19; Meertens et al. 2001) and 1MNDR1 5'GTCGTGAATGAAAGG-GAAAGGGGT 3' (SEQ ID NO: 20; Meertens et al. 2001), and the internal primers Enh780 5' TGACGACAACCCCT-CACCTCAA 3' (SEQ ID NO: 21; Meertens et al. 2001) and 1MNDR25' AGGGGTGGAACTITCGATCTGTAA 3'(SEQ ID NO: 22; Meertens et al. 2001). The tax (577-bp) and polymerase (pol) (709-bp) sequences of HTLV-3 and HTLV-4 were amplified by nested PCR using primers designed from conserved PTLV regions. The external and internal tax primers are PTLVTPG 5'T(C/T)ACCT(G/A) GGACCCCATCGATGGACG 3' (SEQ ID NO: 7) and PGTAXR1 5' GAIGA(T/C)TGI A(C/G)TAC(T/C)AAA-GATGGCTG 3' (SEQ ID NO: 8) and PH2Rrev 5' CCTTATC-CCTCGICTCCCCTC CTT 3' (SEQ ID NO: 9) and PGTAXR2 5' TTIGGG(T/C)AIGGICCGG AAATCAT 3'(SEQ ID NO: 10), respectively. The external and internal pol primers are PGPOLF1 5' C(T/G)TTAAACCIGA(A/G) CGCCT CCAGGC 3' (SEQ ID NO: 11) and PGPOLR1GG (T/C)(A/G)TGIA (A/G)CCA(A/G)(A/G)CIAG(T/G)GG CCA 3' (SEQ ID NO: 12) and PGPOLF2 5' AC(T/C)TGGT (C/T)(C/T) (G/C)(G/C)A(A/G)GGCCCTGGAGG 3' (SEQ ID NO: 13) and PGPOLR2 5' G(A/G)(T/C)(A/G)GGIGTIC CTTTIGAGACCCA 3'(SEQ ID NO: 14), respectively. Inosines (I) and wobble bases (N/N) were used to accommodate areas of heterogeneity (Table 5).

Additional diagnostic PCR with PTLV-specific primers was carried out on samples with negative results for the generic 222-bp tax fragments. Assays described previously were used for PTLV-1 env and STLV-3 LTR (van Dooren et al. 2004) and HTLV-2 env (Switzer et al. 1995). For HTLV-4, a new nested PCR assay was developed based on the HTLV-4 tax sequence using the external primers 1863TF1 5' CTCCT-TCTTTCAGTCCGTGCGGAG 3' (SEQ ID NO: 15) and 1863TR1 5' GGGGTAGTCAGGTTTGGCTGGTAT 3' (SEQ ID NO: 16) and the internal primers 1863TF2 5' CCTACCG-CAACGGATGTCTTGAAA 3' (SEQ ID NO: 17) and 1863TR2 5' TATGGCGCC GGTGTGATGATAAAG 3' (SEQ ID NO: 18) and standard conditions to generate a 275-bp fragment. Percent nucleotide divergence was calculated using the Gap program in the Genetic Computer Group's Wisconsin package. Sequences were aligned using the Clustal W program, gaps were removed, and distance-based trees were generated by using the Kimura two-parameter model in conjunction with the NJ method in the MEGA program (version 2.1) as described elsewhere (van Dooren et al 2004). 1000 bootstrap replicates were used to test the reliability of the final topology of the trees.

Primate Taxonomic Nomenclature

Nomenclature used herein was as described. NHPs were coded using the first letter of the genus and the first two letters of the species names with their house names or codes within parentheses. Cmo=*Cercopithecus mona* (Mona monkey), Cne=*C. neglectus* (De Brazza's guenon), Cmi=*C. mitis* (Sykes's monkey), Cni=*C. nictitans* (greater spot-nosed guenon), Cae=*Chlorocebus* species (African green monkey), Cpo=*C. pogonias* (crowned monkey), Cto=*Cercocebus torquatus* (red-capped mangabey), Cag=*Cercocebus agilis* (agile mangabey), Mog=*Miopithecus ogouensis* (talapoin monkey), Ani=*Allenopithecus nigrpyridis* (Allen's swamp monkey), Msp=*Mandrillus sphinx* (mandrill (mnd)), Pan=*Papio anubis* (olive baboon (bab)), Pcy=*P. cynocephalus* (yellow baboon), Pha=*P. hamadryas* (sacred baboon), Ppu=*P. ursinus* (chacma baboon), Ppa=*P. papio* (Guinea baboon), Pba=*Piliocolobus badius* (red colobus monkey), Mto=*Macaca tonkeana* (Celebes macaque), Ptr=*Pan troglodytes* (chimpanzee), Ppn=*Pan paniscus* (bonobo), Ggo=*Gorilla gorilla* (western lowland gorilla).

TABLE 5

Sequences of primers used for amplifying partial tax, envelope (env), polymerase (pol) and LTR regions of primate T-cell lymphotropic viruses

| Name | Primer sequence[a] (5' to 3') | SEQ ID NO. | Location[b] | Expected PCR product size (bp) | Annealing temp (° C.), No. of cycles |
|---|---|---|---|---|---|
| PH1F | TTGTCATCAGCCCACTTCCCAGG | (SEQ ID NO: 23) | tax, 7243-7262, outer | | |
| PH2R | AAGGAGGGGAGTCGAGGGATAAGG | (SEQ ID NO: 24) | tax, 7478-7455, outer | 236 | 50, 40 |
| PH2F | CCCAGGTTTCGGGCAAAGCCTTCT | (SEQ ID NO: 25) | tax, 7257-7280, inner | | |
| PH2R[c] | AAGGAGGGGAGTCGAGGGATAAGG | (SEQ ID NO: 26) | tax, 7478-7455, inner | 222 | 50, 40 |
| PTLVTPG | T(C/T)ACCT(G/A)GGACCCCATCGATGGACG | (SEQ ID NO: 7) | tax, 7480-7504, outer | | |
| PGTAXR1 | GAIGA(T/C)TGIA(C/G)TAC(T/C)AAAGATGGCTG | (SEQ ID NO: 8) | tax, 8140-8115, outer | 660 | 45, 40 |
| PH2Rrev | CCTTATCCCTCGICTCCCCTCCTT | (SEQ ID NO: 9) | tax, 7529-7552, inner | | |
| PGTAXR2 | TTIGGG(T/C)AIGGICCGGAAATCAT | (SEQ ID NO: 10) | tax, 8106-8085, inner | 577 | 45, 40 |
| PGPOLF1 | C(T/G)TTAAACCIGA(A/G)CGCCTCCAGGC | (SEQ ID NO: 11) | pol, 2611-2634, outer | | |
| PGPOLR1 | GG(T/C)(A/G)TGIA(A/G)CCA(A/G)(A/G)CIAG(T/G)GGCCA | (SEQ ID NO: 12) | pol, 3598-3575, outer | 987 | 45, 40 |
| PGPOLF2 | AC(T/C)TGGT(C/T)(C/T)(G/C)(G/C)A(A/G)GGCCCTGGAGG | (SEQ ID NO: 13) | pol, 2643-2666, inner | | |
| PGPOLR2 | G(A/G)(T/C)(A/G)GGIGTICCTTTIGAGACCCA | (SEQ ID NO: 14) | pol, 3352-3329, inner | 709 | 45, 40 |
| PGENVF1 | TGGATCCCGTGG(A/C)GI(C/T)TCCTIAA | (SEQ ID NO: 27) | env, 5114-5136, outer | | |
| PGENVR1 | GT(A/G)TAIG(C/G)(A/G)(C/G)AIGTCCAIG(A/C)(T/C)TGG | (SEQ ID NO: 28) | env, 5576-5552, outer | 462 | 45, 40 |
| PGENVF2 | AIAGACC(T/A)(C/T)CAAC(A/T)CCATGGGTAA | (SEQ ID NO: 29) | env, 5186-5209, inner | | |
| PGENVR2 | G(A/C)(T/C)TGGCAICCIA(A/G)GTAIGGGCA | (SEQ ID NO: 30) | env, 5557-5535, inner | 371 | 45, 40 |
| GPLTRF1 | (G/A)CCACCAICTIGIGGACAAATAGCTGA | (SEQ ID NO: 31) | LTR, 8256-8282, outer | | |
| GPLTRR2 | C(C/T)GGGCCAAGCCTCGCTGCAGGCA | (SEQ ID NO: 32) | LTR, 8830-8807, outer | 575 | 45, 40 |
| GPLTRF2 | ACCIIGGCTCTGACGTCTCTCCCT | (SEQ ID NO: 33) | LTR, 8333-8356, inner | | |
| GPLTRR2 | GGCAGIAGAAGTGCTACTTTCGAT | (SEQ ID NO: 34) | LTR, 8810-8787, inner | 478 | 45, 40 |

[a]Inosines and wobble nucleotides were included in the primers to accommodate sequence heterogeneity.
[b]The positions of the pol, env, and tax primers are given according to human T-cell lymphotropic virus type 1 (strain ATK); the LTR primer positions are given according to the simian T-cell lymphotropic virus type 3 (strain PH969) genome.
[c]The primer PH2R is used with PH2F in a semi-nested PCR.

Nucleotide Sequence Accession Numbers

The GenBank accession numbers for the 28 new HTLV sequences include AY818406 and AY818433.

Example 2

Figure 4:
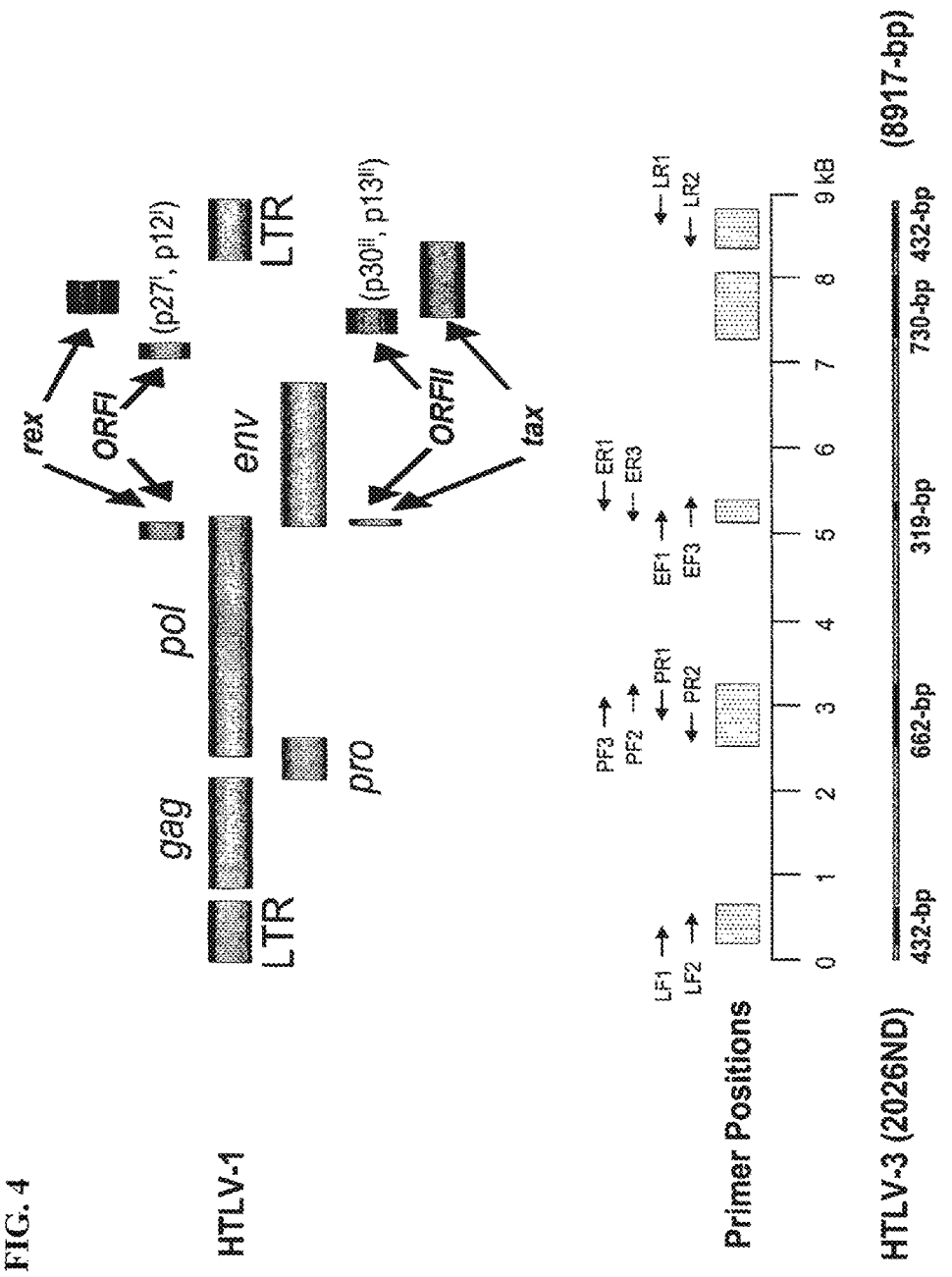
FIG. 4 shows the strategy for PCR-amplifying the entire HTLV-3 (2026ND) genome. Small proviral sequences were first amplified in each major gene region and the long terminal repeat (stippled bars) using generic primers as described in the Methods portion of the Examples section of the specification. The complete proviral sequence was then obtained by using PCR primers located within each major gene region by genome walking as indicated with arrows and orange bars. The typical HTLV-1 genomic organization is provided for reference.

Ancient Origin and Molecular Features of the Human T-Lymphotropic Virus Type 3 Revealed by Complete Genome Analysis Comparison of the HTLV-3(2026ND) Proviral Genome with Prototypical PTLVs Using a combination of primers designed from small sequences obtained in each of the three major genes of PTLV and the LTR region, the complete genome of HTLV-3 (2026ND) was successfully generated as depicted in FIG. 4. Sequence analysis of the overlapping regions, followed by comparison with the genetic structure of other PTLVs, demonstrated that the complete proviral genome of HTLV-3 (2026ND) is 8917-bp. Despite being genetically equidistant from HTLV-1 and HTLV-2, the genomic structure of HTLV-3(2026ND) was similar to that of other PTLVs and included the structural, enzymatic, and regulatory proteins all flanked by long terminal repeats (LTRs). Comparison of HTLV-3 (2026ND) with prototypical PTLV genomes demonstrates that this new human virus is equidistant from the PTLV-1 (62% identity) and PTLV-2 (63% identity) groups across the genome. The results also confirm that HTLV-3 has the closet nucleotide and protein sequence identity to STLV-3 (87-92% identity; Table 6).

PTLV-3 group, HTLV-3(2026ND), which was identified in a hunter from Cameroon, was unique but shared the most overall sequence identity to STLV-3(PPAF3) (92%) from a Senegalese baboon instead of STLV-3(CTO604) (88.4%) identified in red-capped mangabeys, also from Cameroon. This relationship is highlighted further by comparison of HTLV-3 (2026ND) with all available full-length STLV-3 genomes in similarity plot analysis where the highest identity was seen in the highly conserved tax gene. As seen within other PTLV groups, there was no clear evidence of genetic recombination of HTLV-3(2026ND) with STLV-3 or PTLV-1 and PTLV-2 proviral sequences by using bootscanning analysis. HTLV-3 (2026ND) was not compared to the recently reported second strain of HTLV-3 because only two short sequences were available at GenBank and in these region this virus has been shown to be nearly identical to STLV-3(CTO604) (Callatini et al. (2005) *Retrovirology.* 2:30).

Organization of the LTR and Pre-Gag Region

Figure 5B:
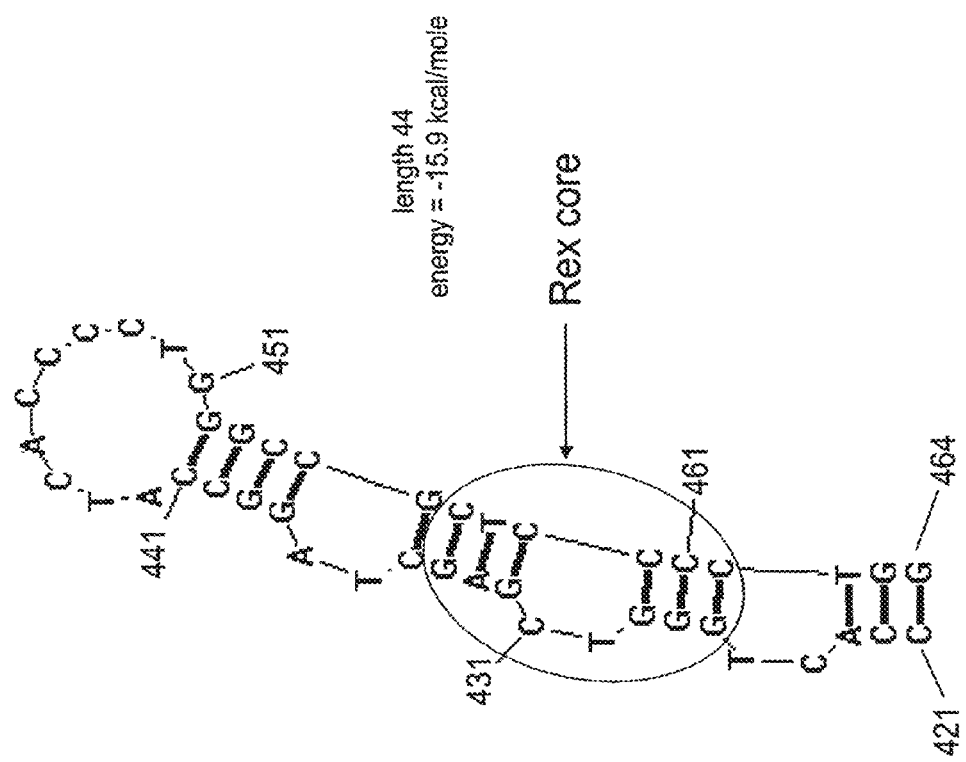
FIG. 5(b) shows the plot of predicted RNA stem loop secondary structure of HTLV-3 (2026ND) LTR region (nucleotides 421-464 of SEQ ID NO: 36). Position of the Rex responsive element (RexRE) core is indicated.

As with STLV-3, the HTLV-3(2026ND) LTR (697-bp) was smaller than that of HTLV-1 (756-bp) and HTLV-2 (764-bp), by having two and not three of the 21-bp transcription regulatory repeat sequences in the U3 region (FIG. 5a; Meertens and Gessain. (2003) *J. Virol.* 77:782-789; Meertens et al. (2002) *J. Virol.* 76:259-268; Van Brussel et al. (1997) *J. Virol.* 7:5464-5472; Van Dooren et al., (2004) *J. Gen. Virol.* 85:507-519). Other regulatory motifs such as the polyadenylation signal, TATA box, and cap site were all conserved in the HTLV-3(2026ND) LTR (FIG. 5a). By secondary structure analysis of the LTR RNA sequence, a stable stem loop structure from nucleotides 421-464 (FIG. 5b) was also observed similar to that shown to be essential for Rex-responsiveness control of viral expression in both HTLV-1 and HTLV-2.

Analysis of the Genomic Structure of HTLV-3(2026ND)

Translation of predicted protein open reading frames (ORFs) across the viral genome identified all major Gag, Pol,

TABLE 6

Percent Nucleotide and Amino Acid Identity of HTLV-3(2026ND) with other PTLV Prototypes[1]

|        | HTLV-1 (ATK) | HTLV-2 (MoT) | STLV-2 (PP1664) | STLV-3 (PH969) | STLV-3 (PPAF3) | STLV-3 (CTO604) | STLV-3 (NG409) |
|--------|---|---|---|---|---|---|---|
| Genome | 61.6 | 62.9 | 62.6 | 86.7 | 92.0 | 88.4 | 90.6 |
| LTR    | 48.7 | 43.7 | 41.4 | 86.2 | 91.1 | 86.9 | 86.9 |
| gag    | 69.3 (83.2) | 69.4 (80.5) | 70.6 (80.7) | 86.4 (95.5) | 91.3 (97.6) | 89.4 (96.2) | 90.6 (96.7) |
| p19    | (74.4) | (68.3) | (67.2) | (95.9) | (95.9) | (95.9) | (94.3) |
| p24    | (90.1) | (90.1) | (90.6) | (98.1) | (99.1) | (98.6) | (99.1) |
| p15    | (78.0) | (73.8) | (72.6) | (88.4) | (96.5) | (90.7) | (94.2) |
| pro    | 59.7 (62.6) | 59.2 (66.7) | 59.4 (59.3) | 83.3 (87.0) | 88.8 (91.5) | 85.0 (89.3) | 88.0 (90.4) |
| pol    | 62.2 (66.2) | 63.9 (71.2) | 63.5 (69.9) | 86.1 (92.7) | 92.6 (94.9) | 88.4 (92.9) | 92.0 (92.9) |
| env    | 65.9 (73.8) | 69.0 (78.2) | 67.1 (77.4) | 88.1 (95.1) | 92.3 (95.1) | 88.4 (94.3) | 91.2 (95.3) |
| SU[2]  | (68.4) | (70.7) | (69.7) | (92.7) | (97.1) | (92.4) | (94.0) |
| TM[2]  | (83.5) | (91.6) | (91.0) | (99.4) | (98.9) | (97.8) | (97.8) |
| rex    | 76.9 (61.9) | 76.3 (60.6) | 75.8 (63.5) | 87.1 (88.5) | 90.9 (94.5) | 88.5 (94.0) | 88.3 (92.3) |
| tax    | 75.4 (81.4) | 73.1 (83.4) | 72.3 (80.4) | 90.2 (97.4) | 94.0 (98.3) | 91.4 (96.6) | 92.8 (96.9) |

[1] amino acid identity in parentheses; strain names given in parentheses below PTLV designation
[2] SU, surface protein; TM, transmembrane protein The most genetic divergence between the PTLV groups was seen in the LTR region (52-59%) while the highest intergroup identity was observed in the highly conserved regulatory genes, tax and rex (72-77%). Interestingly, within the Pro (protease), and Env proteins, as well as the regulatory proteins, Tax and Rex. Translation of the overlapping gag and pro and pro and pol ORFs occurs by one or more successive-1 ribosomal frameshifts that align the different ORFs. The conserved slippage nucleotide sequence 6(A)-8 nt-6(G)-11nt-6 (C) is present in the Gag-Pro overlap, while a point mutation in the Pro-Pol overlap slippage sequence (GTTAAAC (SEQ ID NO: 82) compared to TTTAAAC (SEQ ID NO: 83) in HTLV-1 and HTLV-2) was observed in HTLV-3(2026ND) but the asparagine codon (AAC) crucial for the slippage mechanism was unaffected.

The structural and group specific precursor Gag protein consisted of 422 amino acids (aa) that is predicted to be cleaved into the three core proteins p19 (matrix), p24 (capsid), and p15 (nucleocapsid) similar to HTLV-1, HTLV-2, and STLV-3. Across PTLVs, Gag was one of the most conserved proteins with identities ranging from 81% and 83% for HTLV-1 and PTLV-2, to 95% for STLV-3 supporting the observed cross-reactivity seen with PTLV-3 antisera in Western blot assays using HTLV-1 antigens. Within Gag, the capsid protein showed greater than 90% identity to HTLV-1, while the matrix and nucleocapsid proteins were more divergent sharing less than 78% identity to PTLV-1 and PTLV-2 indicating their potential use in serologic assays for discriminating the three major PTLV groups.

The predicted size of the Env polyprotein is 491 aa, which is slightly shorter than that found in STLV-3s (313 aa versus 314 and 315 for STLV-3(PH969) and STLV-3(CTO-604) due to sequence variation at the carboxy terminus of the surface (SU) protein. In contrast, the transmembrane (TM) protein (178 aa) was highly conserved across all PTLVs supporting further the use of the recombinant HTLV-1 GD21 protein spiked onto WB strips for the identification of divergent PTLVs. Despite the weak reactivity of anti-HTLV-3 (2026ND) antibodies to the HTLV-1 type specific SU peptide (MTA-1; Wolfe et al. (2005) *Proc. Natl. Acad. Sci. USA.* 102:7994-7999) spiked onto WB strips, there was only 70.8% identity of MTA-1 to HTLV-3(2026ND), which is similar to the 68.8% identity of MTA-1 to HTLV-2, demonstrating no clear correlation of WB profile and predicted SU sequence.

The HTLV-1 and HTLV-2 Tax proteins (Tax1 and Tax2, respectively) transactivate initiation of viral replication from the promoter in the 5' LTR and are thus essential for viral expression (Feuer and Green. (2005) *Oncogene.* 24:5996-6004). Tax1 and Tax2 have also been shown to be important for T-cell immortalization, while the HTLV-3 Tax (Tax3) has not yet been characterized (Feuer and Green. (2005) *Oncogene.* 24:5996-6004). Hence, the Tax3 sequences were compared with those of prototypic HTLV-1, PTLV-2, and STLV-3s to determine if motifs associated with these functional characteristics are preserved. Alignment of predicted Tax3 sequences shows excellent conservation of the critical functional regions, including the nuclear localization signal (NLS), cAMP response element (CREB) binding protein (CBP)/P300 binding motifs, and nuclear export signal (NES; HTLV-3 Tax is shown in FIG. 6). The C-terminal transcriptional activating domain (CR2), essential for CBP/p300 binding, was also very conserved except for a single I/V to F mutation at position five of the motif compared to HTLV-1 and PTLV-2, respectively. However, this single amino acid change in the STLV-3 Tax has recently been shown in transient transfection assays to have no deleterious effect on viral transactivation (Chevalier et al. (2005) *AIDS Res. Hum. Retrovir.* 21:513 (Abs. P174)). Since the predicted CR2 domain is conserved in Tax3, similar transactivation activity can be seen with HTLV-3.

Interestingly, although these important functional motifs are highly conserved in PTLV, phenotypic differences of HTLV-1 and HTLV-2 Tax proteins have been observed leading to speculation, that these differences account for the different pathologies associated with both HTLVs (Feuer and Green. (2005) *Oncogene.* 24:5996-6004). Recently, the C-terminus of Tax1, and not Tax2, has been shown to contain a conserved PDZ domain present in cellular proteins involved in signal transduction and induction of the IL-2-independent growth required for T-cell transformation (Rousset et al. (1998) *Oncogene.* 6:643-654; Tsubata et al. (2005) *Retrovirol.* 2:46). The presence of a PDZ domain in PTLV-1 and its absence in PTLV-2 indicates a potential role of this motif in the phenotypic differences of the two viral groups. The consensus PDZ domain has been defined as S/TXV-COOH, where the first amino acid is serine or threonine, X is any amino acid, followed by valine and the carboxy terminus. Examination of the PTLV-3 Tax sequences showed that both HTLV-3 and STLV-3 have predicted PDZ domains with the consensus sequence S(P/S)V compared to T(E/D)V in PTLV-1 (the HTLV-3 PDZ domain is shown in FIG. 6).

Besides Tax and Rex, two additional ORFs coding for four proteins (p27$^I$, p12$^I$, p30$^{II}$, and p13$^{II}$ where I and II denote ORFI and ORFII, respectively) have been identified in the pX region of HTLV-1 (FIG. 4) and are important in viral infectivity and replication, T-cell activation, and cellular gene expression (Bindhu et al. (2004) *Front. Biosc.* 9:2556-2576). Analysis of the pX region of HTLV-3(2026ND) revealed a total of four putative ORFs (named I-IV, respectively) coding for 96, 122, 72, and 118 aa in length. While both ORFIII (72 aa) and ORFIV (118 aa) shared identity to the ORFII of STLV-3 and HTLV-1 and STLV-2/HTLV-2, respectively, and each contained two PXXP motifs, only ORF III was leucine rich like that seen in the leucine zipper motifs of ORFI p12$^I$ (Bindhu et al. (2004) *Front. Biosc.* 9:2556-2576). However, ORFIII did not share any sequence homology with p12$^I$ and both ORFI and ORFII shared only weak sequence identity to miscellaneous cellular proteins available at GenBank. Interestingly, 22 of 28 (79%) amino acids in ORFIV (pos 64-91) were identical among the ORFIIs of all PTLVs indicating a conserved functionality of this motif.

A protein termed the HTLV-1 basic leucine zipper ZIP (bZIP) factor (HBZ) was recently identified in translation of the complementary strand of the viral RNA genome between the env and tax/rex genes (Gaudray et al. (2002) *J. Virol.* 76:12813-12822). Although originally reported to be exclusive to PTLV-1 (Gaudray et al. (2002) *J. Virol.* 76:12813-12822), HBZ is conserved among PTLVs, including HTLV-3(2026ND) (HTLV-3 HBZ is shown in FIG. 7), demonstrating further the potential importance of this protein in viral replication and oncogenesis. The carboxy terminus of the HBZ ORF contains a 21 aa arginine rich region that is relatively conserved in PTLV and known cellular bZIP transcription factors, followed by a leucine zipper region possessing five or four conserved leucine heptads in HTLV-1 and all other PTLVs, respectively. PTLV-1 has 5 leucine heptads similar to that found in mammalian bZIP proteins, while PTLV-1 and PTLV-2 have four leucine heptads followed by leucine octet. Of all PTLVs with full length genomes available at GenBank, only HTLV-2(MoT) did not have the full complement of leucine heptads but was limited to the initial three leucine motifs due to a one nucleotide deletion at position 6823 causing a frameshift in the predicted HBZ sequence.

Phylogenetic Analysis

Figure 8A:
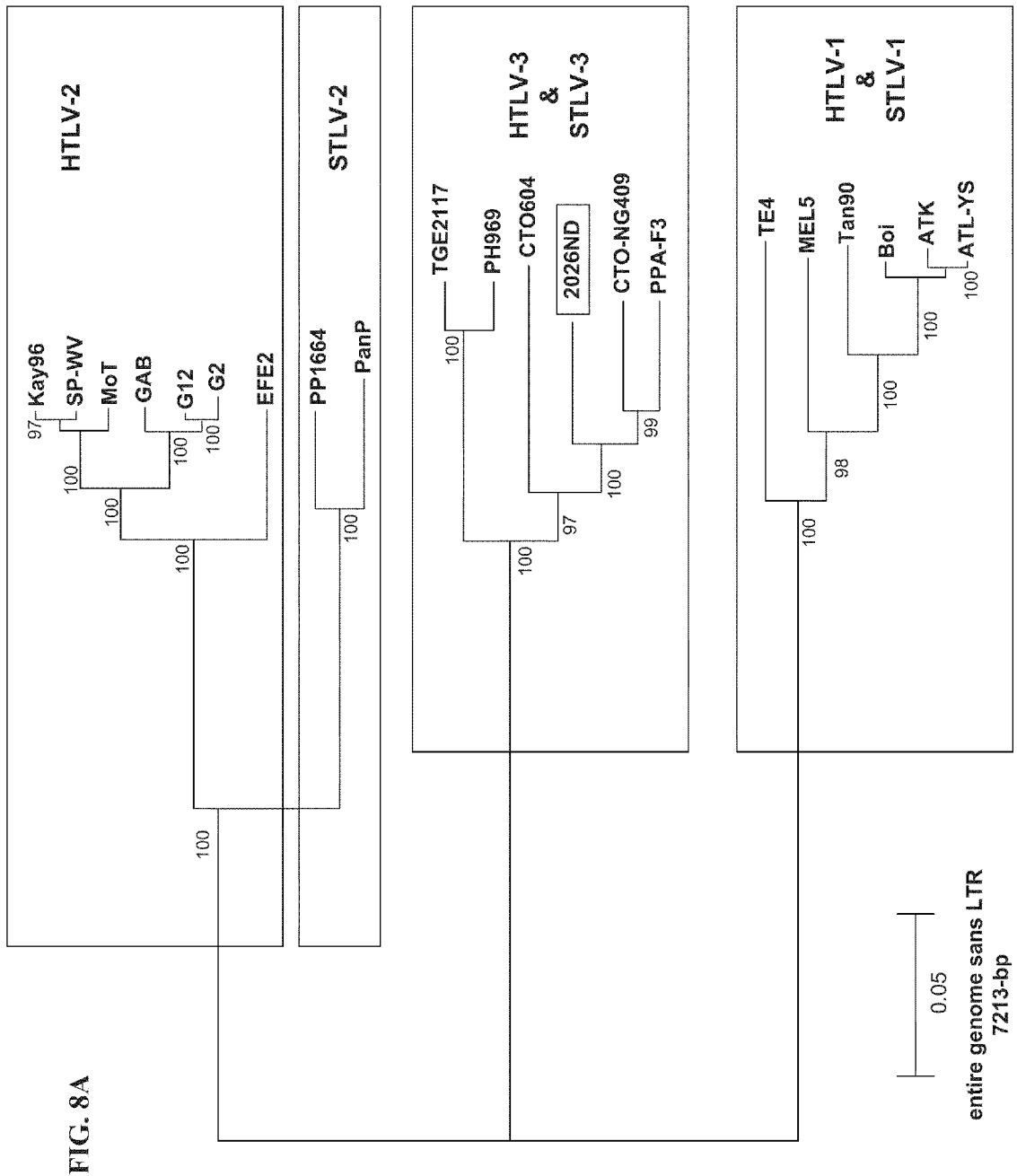
FIG. 8 shows the phylogenetic relationship of HTLV-3 (2026ND) to other PTLVs (a) entire genome sans long terminal repeat (LTR), (b) gag, (c) polymerase (pol), and (d) envelope (env). Sequences generated in the current study are shown in boxes. Support for the branching order was determined by 1,000 bootstrap replicates; only values of 60% or more are shown. Branch lengths are proportional to the evolutionary distance (scale bar) between the taxa.
Figure 8B:
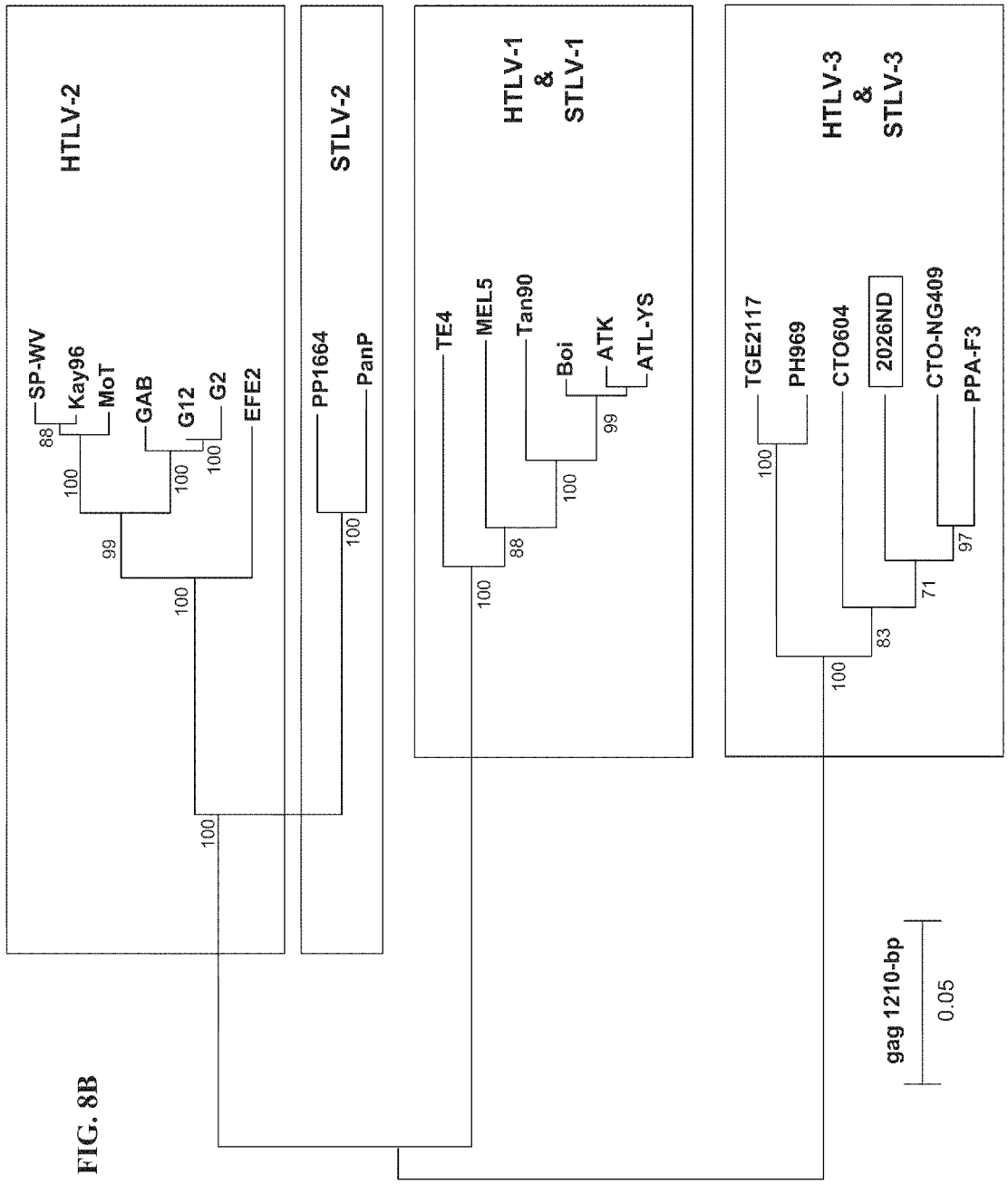
Figure 8C:
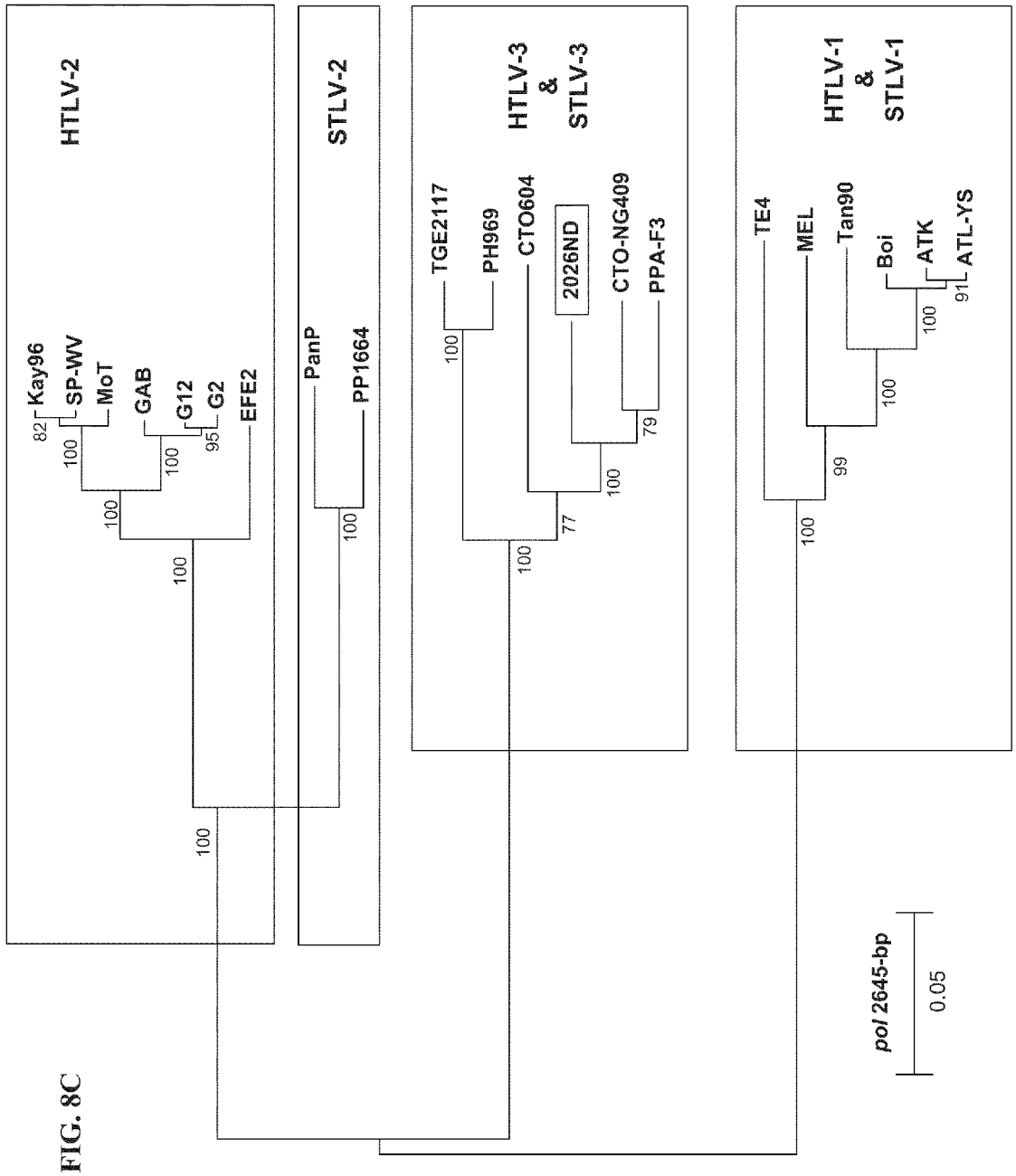
Figure 8D:
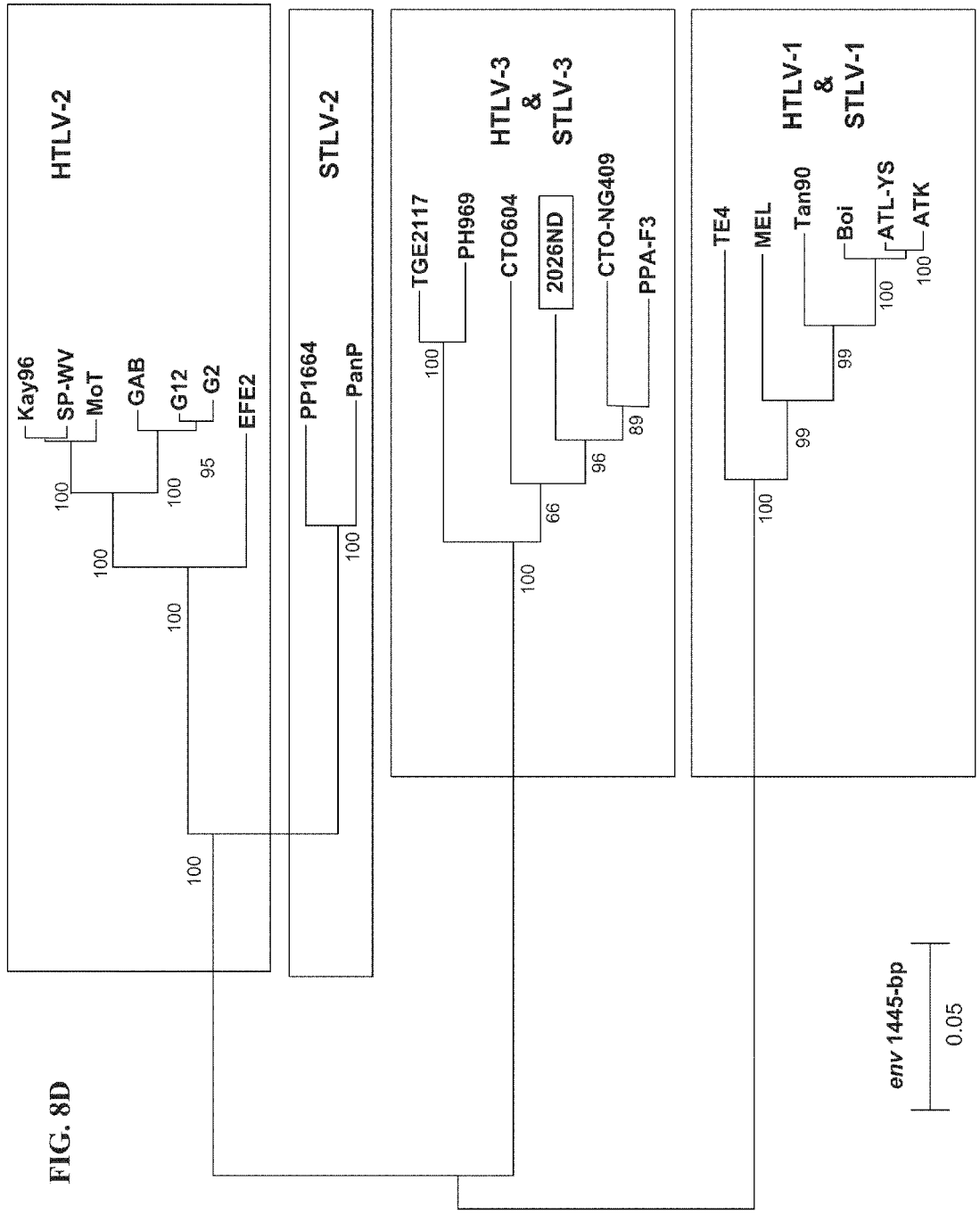

The genetic relationship of HTLV-3(2026ND) to PTLV-3 was confirmed by using aligned full-length prototype sequences excluding the LTR region (FIG. 8a). Phylogenetic analysis inferred three major PTLV groups with very high bootstrap support (100%) with HTLV-1, HTLV-2 and HTLV-3 each clustering in separate clades (FIG. 8a). Within the PTLV-3 phylogroup, HTLV-3(2026ND) formed a separate lineage but clustered with high bootstrap support with STLV-3s from west central Africa (strains CTO604, CTO-NG409, and PPA-F3) indicating a possible primate origin for this human infection in this geographic region. The relationship of HTLV-3 to STLV-3 was supported further by phylogenetic inference of identical tree topologies using an alignment of each major gene region (FIG. 8b-8d). The phylogenetic stability seen across the PTLV genome also demonstrates further the absence of major recombination events occurring in PTLV despite evidence of dual infections in humans and primates (Courgnaud et al. (2004) *J. Virol.* 78:4700-4709), compared to other retroviruses such as HIV which undergo frequent recombination.

Dating the Origin of HTLV-3(2026ND) and Other PTLVs

Figure 9:
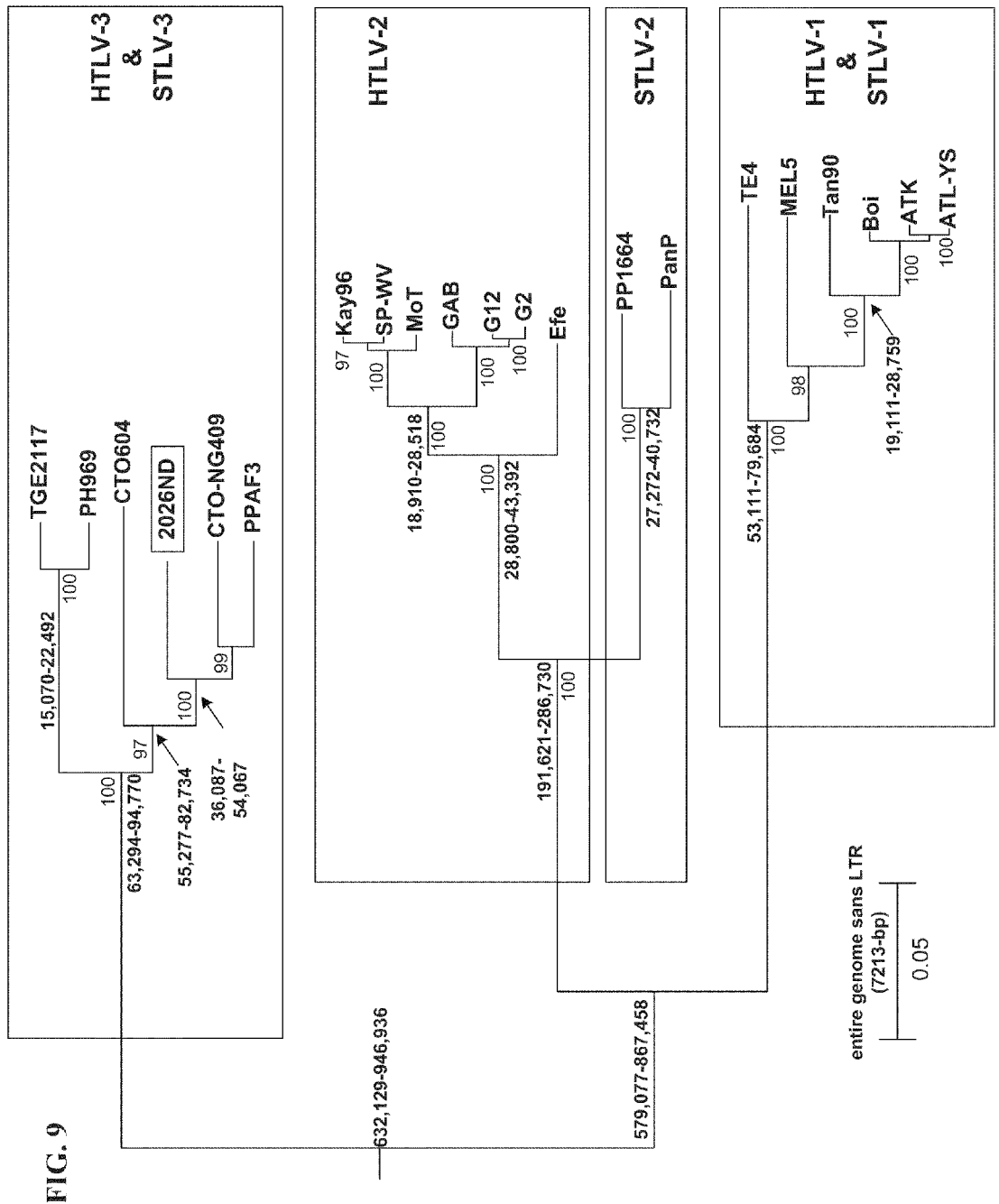
FIG. 9 shows the estimated divergence dates for the most recent common ancestor of HTLV-3(2026ND) and other PTLVs. Divergence dates are provided for each major node of a neighbour-joining tree rooted with PTLV-1 as the outgroup; estimates are provided as ranges using as calibration points 40,000 and 60,000 years ago (YA) as the separation of the Melanesisan HTLV-1 (MEL5) sequence from other PTLV-1 strains. Bootstrap analysis of 1000 replicates is shown on the tree branches; only values >60% are shown.

The finding of HTLVs in three distinct clades indicates an ancient, independent evolution of these viruses. Hence, additional molecular analyses was undertaken in order estimate the divergence times of the PTLV lineages. Although others have reported finding a clock-like behavior of STLV-3 sequences (Meertens and Gessain. (2003) *J. Virol.* 77:782-789; Meertens et al. (2002) *J. Virol.* 76:259-268; Meertens et al. (2003) *J. Gen. Virol.* 84:2723-2727), these results were not confirmed and instead found that PTLVs evolved at different rates by using an alignment of full-length PTLV genomes sans LTR sequences. However, reliable retrovirus divergence times can be obtained by using nonparametric rate smoothing of the sequences to relax the stringency of a clock assumption followed by time calibration of the tree using a value of 40,000-60,000 YA for the origin of the Melanesian HTLV-1 (Sanderson (2003) *Bioinformatics.* 19:301-2; Switzer et al. (2005) *Nature.* 434:376-380; Van Dooren et al. (2004) *J. Gen. Virol.* 85:507-519). By using these dates and methods, the mean evolutionary rate for PTLV was estimated to be $1.12 \times 10^{-6}$ (confidence interval $6.82 \times 10^{-7}$ to $1.56 \times 10^{-6}$) substitutions/site/year, respectively, which is consistent with rates determined previously both with and without enforcing a molecular clock (Lemey et al. (2005) *Infect. Gen. Evol.* 5:291-298; Meertens and Gessain. (2003) *J. Virol.* 77:782-789; Meertens et al. (2002) *J. Virol.* 76:259-268; Meertens et al. (2003) *J. Gen. Virol.* 84:2723-2727; Salemi et al. (2000) *Mol. Biol. Evol.* 17:374-386; Van Dooren et al. (2004) *J. Gen. Virol.* 85:507-519). The mean evolutionary rate for HTLV-3 (2026ND) is estimated to be $9.94 \times 10^{-7}$ (confidence interval $6.04 \times 10^{-7}$ to $1.38 \times 10^{-6}$). The PTLV ancestor was estimated to have originated about 630,000-947,000 YA confirming an archaic evolution of the primate deltaretroviruses (FIG. 9; Salemi et al. (2000) *Mol. Biol. Evol.* 17:374-386). The separation of PTLV-1 and PTLV-2 occurred about 579,077-867,458 YA, while HTLV-2 and STLV-2 diverged around 191,621-286,730 YA (FIG. 9). The origin of all PTLV-3s was estimated to be between 63,294-94,700 YA with the ancestor of HTLV-3(2026ND) occurring about 36,087-54,067 YA (FIG. 9) indicating an ancient origin of this virus in humans. Alternatively, HTLV-3 may represent a recent zoonoses from a primate infected with a very old, divergent STLV-3. However, if HTLV-3 is an old human infection, then it appeared during the same period as the ancestor of both HTLV-1 and HTLV-2 (40,000-60,000 and 28,800-43,392 YA, respectively) and may have also spread to become endemic in specific populations yet to be identified.

Discussion

The complete nucleotide sequence and genomic characterization of the first HTLV-3 that is clearly distinct from all STLV-3s and is genetically equidistant to HTLV-1 and HTLV-2 is described herein. HTLV-3(2026ND) is also unique from the second HTLV-3(Py143) reported recently in a Bakola pygmy from Cameroon since the latter strain is nearly identical to STLV-3 found in a red-capped mangabey, based on the limited sequence data available for this virus (Callatini et al. (2005) *Retrovirology.* 2:30). Although HTLV-1 and HTLV-2 are pathogenic and have spread globally to become endemic in different human populations, little is known about the epidemiology of HTLV-3 infection. However, detailed, comparative sequence analyses of viral genomes can help provide important molecular clues to the origin, evolution, and public health importance of novel human infections.

Like other PTLVs, HTLV-3(2026ND) is genetically stable and its slow evolutionary rate, combined with estimates of known human migrations, can then be used to infer divergence times for HTLV. The finding that the predecessor of HTLV-3(2026ND) originated over 30 millennia ago, an age which is estimated that the ancestors of both HTLV-1 and -2 to have appeared, combined with the wide geographic distribution of STLVs and the recent finding of another HTLV-3 in an African pygmy (Callatini et al. (2005) *Retrovirology.* 2:30; Gessain and Mahieux. (2000) *Bull. Soc. Pathol. Exot.* 93:163-171; Meertens and Gessain. (2003) *J. Virol.* 77:782-789; Meertens et al. (2002) *J. Virol.* 76:259-268; Meertens et al. (2003) *J. Gen. Virol.* 84:2723-2727; Takemura et al. (2002) *J. Virol.* 76:1642-1648; Van Dooren et al. (2004) *J. Gen. Virol.* 85:507-519), collectively indicate that HTLV-3 infection be more frequent than previously understood. In addition, the archaic age of the ancestral HTLVs and the recent finding of STLV-like infections in African hunters collectively imply that cross-species transmission of STLVs to humans is both an ancient and contemporary phenomenon coupled to behavior that exposes humans to nonhuman primates. The ancient origin of HTLV contrasts with that reported for HIV, which is believed to have only crossed over into humans from SW-infected NHPs within the last century, and indicates a long period of viral evolution and adaptation in humans possibly resulting in the observed lower pathogenicity for HTLV compared to HIV (Hahn et al. (2000) *Science* 287:607-614; Sharp et al. (2000) *Biochem Soc Trans.* 28:275-282).

Screening for HTLV-3 can be facilitated by the application of diagnostic serologic and molecular assays based on the sequences reported here. For example, the data show that the Gag matrix and nucleocapsid regions and the envelope surface protein are relatively conserved within PTLV-3 but are divergent from PTLV-1 and PTLV-2 and can thus be used to differentiate the three PTLV groups with serological methods.

At the molecular level, examination of the genomic structure showed that the enzymatic, regulatory, and structural proteins are well preserved in HTLV-3(2026ND), including conserved functional motifs in Tax important for viral expression and T-cell proliferation. The finding of a PDZ domain in the Tax protein of HTLV-3(2026ND), like that seen in HTLV-1 but not HTLV-2 (Feuer and Green. (2005) *Oncogene.* 24:5996-6004), which has been shown to be important in cellular signal transduction and T-cell transformation (Rousset et al. (1998) *Oncogene.* 6:643-654; Tsubata et al. (2005) *Retrovirol.* 2:46), indicates that the HTLV-3 Tax is more phenotypically similar to HTLV-1 than HTLV-2. The high amino acid identity of the PTLV-3 Tax proteins combined with the ability of STLV-3 to transform human cells in vitro indicates that the HTLV-3 Tax functions similarly (Goubau et al. (1994) *Proc. Natl. Acad. Sci. USA* 91:2848-2852).

In contrast to the tax gene, the HTLV-3(2026ND) LTR has only two of the three conserved promoters identified in HTLV-1 and HTLV-2 that are responsible for basal viral transcription levels and like STLV-3 is missing the TATA-distal 21-bp repeat element (Meertens and Gessain. (2003) *J. Virol.* 77:782-789; Meertens et al. (2002) *J. Virol.* 76:259-268; Meertens et al. (2003) *J. Gen. Virol.* 84:2723-2727; Van Brussel et al. (1997) *J. Virol.* 7:5464-5472; Van Dooren et al. (2004) *J. Gen. Virol.* 85:507-519). All of the remaining functional elements in the LTR were conserved, including the stem loop structure necessary for Rex responsive control of viral expression in HTLV-1 and -2.

Recently, a HBZ protein was identified in translation of the complementary strand of the viral RNA genome between the env and tax/rex genes (Gaudray et al. (2002) *J. Virol.* 76:12813-12822). Protein translation on the minus-strand RNA is a unique feature of HTLV-1 not previously seen in retroviruses. HBZ was shown to be involved in the negative regulation of viral replication (Gaudray et al. (2002) *J. Virol.* 76:12813-12822). The more recent finding of HBZ mRNA expression in ATL patients indicates a role of HBZ mRNA in the survival of leukemic cells in vivo and in HTLV-1-associated oncogenesis (Satou et al. (2006) *Proc. Natl. Acad. Sci. USA.* 103:720-725). Although originally reported to be exclusive to PTLV-1 (Gaudray et al. (2002) *J. Virol.* 76:12813-12822), HBZ is conserved among PTLVs, including HTLV-3(2026ND), demonstrating further the potential importance of this protein in viral replication and oncogenesis. Of all PTLVs with full length genomes available at GenBank, only HTLV-2(MoT) did not have the full complement of leucine heptads in the leucine zipper due to a frameshift mutation in the predicted HBZ sequence.

In summary, disclosed herein, HTLV-3(2026ND) is genetically stable and has an ancient origin. HTLV-3(2026ND) genomic structure is relatively conserved and contains many of the functional motifs important for the viral expression and pathology associated with HTLVs.

Materials and Methods
DNA Preparation and PCR-Based Genome Walking

DNA was prepared from uncultured PBMCs available from person 2026ND identified in the original PTLV surveillance study in Cameroon reported in detail elsewhere (Wolfe et al. (2005) *Proc. Natl. Acad. Sci. USA.* 102:7994-7999). DNA integrity was confirmed by β-actin polymerase chain reaction (PCR) as previously described (Wolfe et al. (2005) *Proc. Natl. Acad. Sci. USA.* 102:7994-7999). All DNA preparation and PCR assays were performed in a laboratory where only human specimens are processed and tested according to recommended precautions to prevent contamination. To obtain the full-length genomic sequence of HTLV-3 small regions of each major coding region were PCR-amplified by using nested PCR and degenerate PTLV primers. The tax (577-bp) and polymerase (pol) (709-bp) sequences were amplified by using primers and conditions provided elsewhere (Wolfe et al. (2005) *Proc. Natl. Acad. Sci. USA.* 102: 7994-7999). Envelope (env) (371-bp) sequences were amplified by using standard PCR conditions with a 45° C. annealing temperature and the external and internal primers PGENVF1 5' TGGATCCCGTGG(A/C)GI(C/T)TCCTIAA 3' (SEQ ID NO: 27) and PGENVR1 5' GT(A/G)TAIG(C/G)(A/G)(C/G)AIGTCCAIG(A/C)(T/C)TGG 3' (SEQ ID NO: 28) and PFENVF2 5' AIAGACC(T/A)(C/T)CAAC(A/T)CCATGGGTAA 3' (SEQ ID NO: 29) and PGENVR2 5' G(A/C)(T/C)TGGCAICCIA(A/G)GTAIGGGCA 3' (SEQ ID NO: 30), respectively. A 398-bp fragment of the long terminal repeat (LTR) was obtained by using conserved STLV-3 primers as previously reported (Wolfe et al. (2005) *Proc. Natl. Acad. Sci. USA.* 102:7994-7999).

HTLV-3(2026ND)-specific primers were then designed from sequences obtained in each of the four viral regions described above and were used in nested, long-template PCRs to fill in the gaps in the genome as depicted in FIG. 4 by using an expand high fidelity kit containing both Taq and Tgo DNA polymerases (Roche). The external and internal primer sequences for the LTR-pol and pol-env fragments are 2026LF1 5' GGTAAGATCCCACTGGGTCGAGC 3'(SEQ ID NO: 69) and 2026PR1 5' GAAGCCAGGTCTCGGGTGACG 3' (SEQ ID NO: 70) and 2026LF2 5' CGCTCCCCTGGAGCTCTCTCG 3'(SEQ ID NO: 71) and 2026PR2 5' GCCACTTCCCATTGGGCTTTTTGACGG 3' (SEQ ID NO: 72) and 2026 PF3 5' GCTCTCACCGATAAAGTAACAAACG 3' (SEQ ID NO: 73) and 2026ER1 5' GGTAGGAAGAGGCTCCTATGAACAG 3' (SEQ ID NO: 74) and 2026 PF2 5' CAGGACTGCATAACATACGAGACCCTCC 3' (SEQ ID NO: 75) and 2026ER3 5' CCTATGAACAGGGTGCATCGACTGGG 3' (SEQ ID NO: 76), respectively. The external and internal primer sequences used to obtain about 3 kb of the 3' end of the genome (env-tax-LTR) are 2026EF1 5' CCTAAGCCCCCCATGTCCAGAC 3' (SEQ ID NO: 77) and 2026LR1 5' CGAGAGAGCTCCAGGGGAGCG 3' (SEQ ID NO: 78) and 2026EF3 5' CCTACTCCCTGTATGTATTCCCCCATTGG 3' (SEQ ID NO: 79) and 2026LR2 5' GCTCGACCCAGTGGGATCTTACCGAGTGG 3' (SEQ ID NO: 80), respectively.

PCR products were revealed on 1.5% agarose gels stained with ethidium bromide, purified with a QIAQUICK™ PCR purification kit (Qiagen) and sequenced in both directions with a BIGDYE™ terminator cycle kit and automated sequencers (Applied Biosystems). Selected PCR products were also cloned into the pCR4-TOPO vector using the TOPO TA Cloning kit (Invitrogen) and recombinant plasmid DNA was prepared using the Qiagen plasmid purification kit prior to automated sequencing.

Sequence and Phylogenetic Analysis

Percent nucleotide divergence was calculated by using the GAP program in the Genetic Computer Group's (GCG) Wisconsin package (Thompson et al. (1994) *Nucleic Acids Res.* 22:4673-4680). LTR RNA secondary structure was determined using the program RNAstructure v4.2 (Mathews et al. (1999) *J. Mol. Biol.* 288:911-940). Sequences were aligned by using the Clustal W program (Womble (2000) *Methods Mol. Biol.* 132:3-22), gaps were removed, and distance-based trees were generated by using the Kimura two-parameter model in conjunction with the neighbor-joining (NJ) method in the MEGA program (version 2.1) and maximum likelihood (ML) analysis in the PAUP* program as described in detail elsewhere (Switzer et al. (2005) *Nature.* 434:376-380; Wolfe et al. (2005) *Proc. Natl. Acad. Sci. USA.* 102:7994-7999). The reliability of the final topology of the trees was tested with 1,000 bootstrap replicates. Comparison of full-length PTLV genomes available at GenBank was done using HTLV-3 (2026ND) as the query sequence and the F84 (ML) model and a transition/transversion ratio of 2.0 implemented in the program SimPlot (Lole et al. (1999) *J. Virol.* 73:152-160).

For dating of HTLV-3(2026ND), full-length genomes from prototypical PTLVs available at GenBank were aligned with HTLV-3(2026ND) by using Clustal W, gaps were removed, and minor adjustments in the alignment were made manually. LTR sequences were excluded from the analysis since this region does not align accurately in PTLVs. The best fitting evolutionary model for the aligned sequences was determined with Modeltest v3.6 (Posada and Crandall. (1998) *Bioinformatics.* 14:817-818). The general time-reversible model, allowing six different substitution rate categories, with gamma-distributed rate heterogeneity (1.9724) and an estimated proportion of invariable sites (0.3687), was determined to be the best fit to the data. Little substitution saturation was observed in the 7213-bp alignment ($P<0.0001$) as determined with the DAMBE program, and was therefore satisfactory for use in phylogenetic analyses. Likewise, using the best-fitting evolutionary model defined above, good phylogenetic signal in the alignment was also found with likelihood mapping analysis using the program Tree-Puzzle v5.2.

The molecular clock hypothesis, or constant rate of evolution, was tested by using the likelihood ratio test with the likelihoods for the ML and clock-like ML trees obtained in PAUP*. The clock was tested with the best-fitting evolutionary model estimated in Modeltest, and ML trees were constructed in PAUP* starting from the NJ tree that is iteratively optimized using two consecutive heuristic searches with nearest neighbor interchange followed by a final heuristic search with the tree-bisection-reconnection algorithm. To adjust for rate heterogeneity among different PTLV taxa, clock-like ML trees were then transformed into ultrametric trees using the nonparametric rate smoothing (NPRS) algorithm in the program TreeEdit (v1.0a10 carbon) (Sanderson (2003) *Bioinformatics*. 19:301-2). The branches of the NPRS tree were then scaled by using a divergence time of 40,000-60,000 years ago (ya) for the Melanesian HTLV-1mel lineage based on genetic and archaeological evidence of when the ancestors of indigenous Melanesians and Australians migrated from Southeast Asia (Lemey et al. (2005) *Infect. Gen. Evol.* 5:291-298; Salemi et al. (2000) *Mol. Biol. Evol.* 17:374-386; Salemi et al. (1999) *AIDS Rev.* 1:131-139). Variance in age estimates (branch lengths) was determined in PAUP* with 100 bootstrap repetitions by enforcing topological constraints and using a heuristic search without branch swapping on the clock-like ML tree. Branch lengths in all 100 trees were calibrated as before and average divergence times and confidence intervals ($\alpha=0.05$) were calculated in Excel. The evolutionary rate was estimated based on a known divergence time point of 40,000-60,000 ya and on the branch length of the ML clock-like tree according to the formula: evolutionary rate (r)=branch length (bl)/divergence time (t) (Van Dooren et al. (2004) *J. Gen. Virol.* 85:507-519).

Nucleotide Sequence Accession Number

The HTLV-3(2026ND) proviral sequence has the GenBank accession number DQ093792.

identified in the original PTLV surveillance study in Cameroon reported in detail elsewhere (Wolfe et al. (2005) *Proc. Natl. Acad. Sci. USA*. 102:7994-7999). DNA integrity was confirmed by β-actin polymerase chain reaction (PCR) as previously described (Wolfe et al. (2005) *Proc. Natl. Acad. Sci. USA*. 102:7994-7999). To obtain the full-length genomic sequence of HTLV-3, small regions of each major coding region were PCR-amplified using nested PCR and degenerate PTLV primers.

HTLV-3(2026ND)-specific primers were then designed from sequences obtained in each of the four viral regions described above (tax, pol, env, and LTR), and used in nested, long-template PCRs to fill in the gaps in the genome using an expand high fidelity kit containing both Taq and Tgo DNA polymerases (Roche). PCR products were revealed on 1.5% agarose gels stained with ethidium bromide, purified with a Qiaquick™ PCR purification kit (Qiagen) and sequenced in both directions with a BigDye™ terminator cycle kit and automated sequencers (Applied Biosystems). Selected PCR products were also cloned into the pCR4-TOPO vector using the TOPO TA Cloning kit (Invitrogen) and recombinant plasmid DNA was prepared using the Qiagen plasmid purification kit prior to automated sequencing.

Percent nucleotide divergence was calculated by using the GAP program in the Genetic Computer Group's (GCG) Wisconsin package (Thompson et al. (1994) *Nucleic Acids Res.* 22:4673-4680). LTR RNA secondary structure was determined using the program RNAstructure v4.2 (Mathews et al. (1999) *J. Mol. Biol.* 288:911-940). Sequences were aligned by using the Clustal W program (Womble (2000) *Methods Mol. Biol.* 132:3-22), gaps were removed, and distance-based trees were generated by using the Kimura two-parameter model in conjunction with the neighbor-joining (NJ) method in the MEGA program (version 2.1) and maximum likelihood (ML) analysis in the PAUP* program as described in detail elsewhere (Switzer et al. (2005) *Nature.* 434:376-380; Wolfe et al. (2005) *Proc. Natl. Acad. Sci. USA*. 102:7994-7999). The reliability of the final topology of the trees was tested with 1,000 bootstrap replicates. Table 7 shows a comparison of the genetic identity of the HTLV-3 and HTLV-4 full-length genomes with other PTLV prototypes. The stem loop structure necessary for Rex responsive control of viral expression in HTLV-1 and -2 was retained in HTLV-4(1863LE), and is shown in FIG. 11.

TABLE 7

Genetic Identity of HTLV-3 and HTLV-4 Genomes with other PTLV Prototypes (strain)

| | HTLV-1 (ATK) | STLV-1 (Tan) | HTLV-2 (MoT) | STLV-2 (PP1664) | STLV-3 (TGE2117) | STLV-3 (CTO604) | HTLV-3 (2026ND) | HTLV-3 (Pyl43) | HTLV-4 (1863LE) |
|---|---|---|---|---|---|---|---|---|---|
| HTLV-3 | | | | | | | | | |
| 2026ND | 61.6 | 61.6 | 62.9 | 62.6 | 87.1 | 88.4 | — | 88.5 | 63.2 |
| Pyl43 | 62.3 | 62.1 | 63.1 | 63.2 | 87.7 | 99.2 | 88.5 | — | 63.0 |
| HTLV-4 | | | | | | | | | |
| 1863LE | 62.0 | 62.0 | 70.7 | 70.8 | 63.5 | 63.1 | 63.2 | 63.0 | — |

Example 3

Generation and Analysis of the Human T-Lymphotropic Virus Type 4 Complete Genome The full-length genomic sequence of HTLV-4 (SEQ ID NO: 81) shown in FIG. 10 was obtained substantially as described above in Example 2 for the identification if the HTLV-3 full-length genomic sequence. Briefly, DNA was prepared from uncultured PBMCs available from a subject For dating of HTLV-4(1863LE), full-length genomes from prototypical PTLVs available in GenBank were aligned with HTLV-3(2026ND) and HTLV-4(1863LE) essentially as described in Example 2 using Clustal W. The analysis, shown in FIG. 12, again inferred four major phylogroups with very high bootstrap support, confirming the genetic relationships that were based on smaller sequences. Both HTLV-3s again clustered with STLV-3s supporting a primate origin for these viruses. HTLV-4 again formed a new lineage distinct from PTLV-1, PTLV-2, and PTLV-3. However, the primate origin of HTLV-4 was less clear since there is not yet a known simian counterpart for this virus. These results also indicated the absence of genetic recombination in PTLVs, which is a common mechanism that leads to increased genetic diversity of HIV.

The finding of HTLVs in four distinct clades indicated an ancient, independent evolution of these viruses. Thus, additional molecular analyses were performed to estimate the divergence times of the PTLV lineages. FIG. 13 shows the estimated divergence dates for the most recent common ancestor of HTLV-3(2026ND), HTLV-4(1863LE) and other PTLVs. Using the bovine leukemia virus (BLV) as an outgroup, a substitution rate of $8.6 \times 10^{-7}$ to $1.3 \times 10^{-6}$ substitutions/site/year for PTLV was inferred which is 3 logs lower than that seen in HIV, confirming the genetic stability of these deltaretroviruses.

Using these substitution rates, molecular dating inferred an ancient origin for PTLVs hundreds of thousands of years ago with the most recent common ancestor for each HTLV group ranging from 30,000 years ago for HTLV-2 to 456,000 years ago for HTLV-4. This finding contrasts with the more recent origin of HIV-1, which has been estimated to have occurred within the last century.

The inferred ancient origin for HTLV-3 and HTLV-4 indicates that exposure to these viruses may have been occurring for millennia, and thus these viruses may be more prevalent than currently known. Alternatively, HTLV-3 and HTLV-4 may represent more recent infections with highly divergent STLVs that have yet to be identified. This is probably the case for the HTLV-3(Py143) strain, since the high genetic identity of this virus to STLV-3RCM is similar to that seen in transmission pairs. Expanded surveillance of both humans and primates is warranted.

Changes in the molecular structure and genetic sequences of viruses has been proposed to play a role in the increased transmissibility and pathogenicity of viruses following cross-species transmission and adaptation to a new host. Thus, the genetic structure and sequences of HTLV-3 and HTLV-4 were examined to determine if the genome was intact and if important functional motifs involved in viral expression and HTLV-1-induced leukemogenesis are preserved. The Tax proteins of HTLV-3 were also characterized using in vitro assays to determine if motifs involved in Tax-mediated leukemogenesis were present and functioning.

While all structural and enzymatic proteins of both HTLV-3s and HTLV-4 were intact, features that are either unique or similar to those of other HTLVs were identified (see Table 8). First, the genomes of HTLV-3 and HTLV-4 are shorter than HTLV-1 and HTLV-2 by having only two of three Tax response elements in the LTRs. However, the loss of this distal TRE has been shown to not significantly affect HTLV expression. In addition, only two TREs are present in STLV-3 and STLV-2 suggesting this difference is not a result of adaptation to a new host. Likewise, the finding of AP-1 and c-Myb transcription factors in place of the HTLV-3 or HTLV-4 LTRs is also not unique but are also present in STLV-3.

Overall, the HTLV-3 Tax protein contains many of the functional motifs important for viral expression and leukemogenesis attributed to HTLV-1 Tax. Detailed in vitro analysis confirmed that the HTLV-3 Tax was similar in function to the HTLV-1 Tax protein, suggesting a pathogenic potential in HTLV-3-infected persons like that observed in HTLV-1. The HTLV-3(Py143) genome is also shorter by a 366-bp deletion in the pX region that disrupts the HBZ reading frame suggesting a loss of Tax suppression and T-cell proliferation believed to be associated with this gene.

TABLE 8

Unique Genetic Features of HTLV Prototypes: HTLV-3 is more similar to HTLV-1

|  | HTLV-1 (ATK) | HTLV-2 (MoT) | HTLV-3 (2026ND)* | HTLV-3 (Py143)** | HTLV-4 (1863LE) |
|---|---|---|---|---|---|
| Genome (bp) | 9068 | 8952 | 8917 | 8553 | 8791 |
| LTR (bp) | 756 | 764 | 697 | 695 | 696 |
| # LTR TREs | 3 | 3 | $2^1$ | $2^1$ | $2^1$ |
| Other LTR TFs | — | — | AP-1 | c-Myb | c-Myb |
| Tax transactivates | Yes | Yes | Yes | Yes |  |
| Tax localization | Nucleus | Cytoplasm |  | Nucleus |  |
| Tax p53 inhibition | Yes |  |  | Yes |  |
| PDZ BD in Tax | Yes | No | Yes | Yes | No |
| HBZ | Yes | $No^2$ | Yes | $No^3$ | Yes |

[1] missing distal TRE
[2] HBZ is present in other HTLV-2
[3] 366-bp deletion in pX
*Switzer et al. *J Virol.* 2006; 80: 7427-38.
**Calattini et al. *J Virol.* 2006; 80: 9876-88.

REFERENCES

Araujo & Hall, Human T-lymphotropic virus type II and neurological disease. *Ann. Neurol.* 56, 10-19 (2004).

Barnhart et al., 1997. Function of the human T-cell leukemia virus type 1 21-base-pair repeats in basal transcription. *J. Virol.* 71:337-344.

Bindhu et al., 2004. Role of accessory proteins of HTLV-1 in viral replication, T cell activation, and cellular gene expression. *Front. Biosc.* 9:2556-2576.

Bowen-Jones & Pendry, The threat to primates and other mammals from the bushmeat trade in Africa, and how this threat could be diminished. *Oryx* 33, 233-246 (1999).

Busch et al., Absence of evidence of infections with divergent simian T-lymphotropic viruses in US blood donors with seroindeterminate human T-lymphotropic results. *Transfusion* 40, 443-449 (2000).

Callatini et al., 2005. Discovery of a new human T-cell lymphotropic virus (HTLV-3) in Central Africa. *Retrovirology.* 2:30.

Chevalier et al., 2005. Molecular characterization of the Tax protein from the highly divergent simian T-cell lymphotropic virus type 3 strain. *AIDS Res. Hum. Retrovir.* 21:513 (Abs. P174).

Courgnaud et al., Simian T-cell leukemia virus (STLV) infection in wild primate populations in Cameroon: evidence for dual STLV type 1 and type 3 infection in agile mangabeys (*Cercocebus agilis*). *J. Virol.* 78, 4700-4709 (2004).

Digilio et al., 1997. The simian T-lymphotropic/leukemia virus from *Pan paniscus* belongs to the type 2 family and infects Asian macaques. *J. Virol.* 71:3684-3692.

Feuer and Green. 2005. Comparative biology of human T-cell lymphotropic virus type 1 (HTLV-1) and HTLV-2. *Oncogene*. 24:5996-6004.

Gaudray et al., 2002. The complementary strand of the human T-cell leukemia virus type 1 RNA genome encodes a bZIP transcription factor that down-regulates viral transcription. *J. Virol.* 76:12813-12822.

Gessain & Mahieux, Epidemiology, origin and genetic diversity of HTLV-1 retrovirus and STLV-1 simian affiliated retrovirus. *Bull. Soc. Pathol. Exot.* 93, 163-171 (2000).

Goubau et al., A primate T-lymphotropic virus, PTLV-L, different from human T-lymphotropic viruses types I and II, in a wild-caught baboon (*Papio hamadryas*). *Proc. Natl. Acad. Sci. USA* 91, 2848-2852 (1994).

Groves *Primate Taxonomy* (Smithsonian Institution Press, Washington, D.C., 2001).

Hahn et al., 2000. AIDS as a zoonosis: scientific and public health implications. *Science* 287:607-614.

Heneine et al., Identification of a human population infected with simian foamy viruses. *Nat. Med.* 4, 403-407 (1998).

Khabbaz et al., Brief report: infection of a laboratory worker with simian immunodeficiency virus. *N. Engl. J. Med.* 330, 172-177 (1994).

Leendertz et al., High variety of different simian T-cell leukemia virus type 1 strains in chimpanzees (*Pan troglodytes verus*) of Tai National Park, Cote d'Ivoire. *J. Virol.* 78, 4352-4356 (2004).

Lemey et al., 2005. A Bayesian statistical analysis of human T-cell lymphotropic virus evolutionary rates. *Infect. Gen. Eva* 5:291-298.

Lerche et al., Evidence of infection with simian type D retrovirus in persons occupationally exposed to nonhuman primates. *J. Virol.* 75, 1783-1789 (2001).

Lole et al., 1999. Full-length human immunodeficiency virus type 1 genomes from subtype C-infected seroconverters in India, with evidence of intersubtype recombination. *J. Virol.* 73:152-160.

Mahieux et al., Simian T-cell lymphotropic virus type 1 from *Mandrillus sphinx* as a simian counterpart of human T-cell lymphotropic virus type 1 subtype D. *J. Virol.* 72, 10316-10322 (1998).

Mahieux et al., Molecular epidemiology of 58 new African human T-cell leukemia virus type 1 (HTLV-1) strains: identification of a new and distinct molecular subtypes in central Africa and in pygmies. *J. Virol.* 71, 1317-1333 (1997).

Mahieux et al., 2000. Human T-cell lymphotropic virus type 1 gag indeterminate western blot patterns in Central Africa: relationship to *Plasmodium falciparum* infection. *J. Clin. Microbiol.* 38:4049-4057.

Mathews et al., 1999. Expanded sequence dependence of thermodynamic parameters improves prediction of RNA secondary structure. *J. Mol. Biol.* 288:911-940.

Meertens and Gessain. 2003. Divergent simian T-cell lymphotropic virus type 3 (STLV-3) in wild-caught Papio hamadryas papio from Senegal: widespread distribution of STLV-3 in Africa. *J. Virol.* 77:782-789.

Meertens, et al., Complete sequence of a novel highly divergent simian T-cell lymphotropic virus from wild-caught red-capped mangabeys (*Cercocebus torquatus*) from Cameroon: a new primate T-lymphotropic virus type 3 subtype. *J. Virol.* 76, 259-268 (2002).

Meertens et al., A. Molecular and Phylogenetic Analyses of 16 Novel Simian T Cell Leukemia Virus Type 1 from Africa: Close Relationship of STLV-1 from *Allenopithecus nigroviridis* to HTLV-1 Subtype B Strains. *Virology* 287, 275-285 (2001).

Meertens et al., 2003. A novel, divergent simian T-cell lymphotropic virus type 3 in a wild-caught red-capped mangabey (*Cercocebus torquatus torquatus*) from Nigeria. *J. Gen. Virol.* 84:2723-2727.

Milner-Gulland et al., Wild meat: the bigger picture. *TREE* 18, 351-357 (2003).

Nerrienet et al., Simian T cell leukemia virus type I subtype B in a wild-caught gorilla (*Gorilla gorilla gorilla*) and chimpanzee (*Pan troglodytes vellerosus*) from Cameroon. *J Gen Virol.* 85: 25-9 (2004).

Posada and Crandall. 1998. MODELTEST: testing the model of DNA substitution. *Bioinformatics.* 14:817-818.

Rousset et al., 1998. The C-terminus of the HTLV-1 Tax oncoprotein mediates interaction with the PDZ domain of cellular proteins. *Oncogene.* 6:643-654.

Salemi et al., Tempo and mode of human and simian T-lymphotropic virus (HTLV/STLV) evolution revealed by analyses of full-genome sequences. *Mol. Biol. Evol.* 17, 374-386 (2000).

Salemi et al., A.M. Origin and evolution of human and simian T-cell lymphotropic viruses. *AIDS Rev.* 1, 131-139 (1999).

Sanderson 2003. r8s: inferring absolute rates of molecular evolution and divergence times in the absence of a molecular clock. *Bioinformatics.* 19:301-2.

Satou et al., 2006 HTLV-1 basic leucine zipper factor gene mRNA supports proliferation of adult T cell leukemia cells. *Proc. Natl. Acad. Sci. USA.* 103:720-725.

Sharp et al., 2000. Origins and evolution of AIDS viruses: estimating the time-scale. *Biochem Soc Trans.* 28:275-282.

Slattery et al., Genomic evolution, patterns of global dissemination, and interspecies transmission of human and simian T-cell leukemia/lymphotropic viruses. *Genome Res.* 9, 525-549 (1999).

Switzer M et al., 2005. Ancient co-speciation of simian foamy viruses and primates. *Nature.* 434:376-380.

Switzer et al., Phylogenetic relationship and geographic distribution of multiple human T-cell lymphotropic virus type II subtypes. *J. Virol.* 69, 621-632 (1995).

Takemura et al., 2002. High prevalence of simian T-lymphotropic virus type L in wild Ethiopian baboons. *J. Virol.* 76:1642-1648.

Thompson et al., 1994. CLUSTAL W: improving the sensitivity of progressive multiple sequence alignment through sequence weighting, position-specific gap penalties and weight matrix choice. *Nucleic Acids Res.* 22:4673-4680.

Tsubata et al., 2005. PDZ domain-binding motif of human T-cell leukemia virus type 1 Tax oncoprotein is essential for the interleukin 2 independent growth induction of a T-cell line. *Retrovirol.* 2:46.

Van Brussel et al., 1998. The simian T-lymphotropic virus STLV-PP1664 from *Pan paniscus* is distinctly related to HTLV-2 but differs in genomic organization. *Virology.* 243: 366-379.

Van Brussel et al., 1997. Complete nucleotide sequence of the new simian T-lymphotropic virus, STLV-PH969 from a Hamadryas baboon, and unusual features of its long terminal repeat. *J. Virol.* 7:5464-5472.

Van Dooren et al., Evidence for a second simian T-cell lymphotropic virus type 3 in *Cercopithecus nictitans* from Cameroon. *J. Virol.* 2001 December; 75(23):11939-41.

Van Dooren et al., Identification in gelada baboons (*Theropithecus gelada*) of a distinct simian T-cell lymphotropic virus type 3 with a broad range of Western blot reactivity. *J. Gen. Virol.* 85, 507-519 (2004).

van Regenmortel et al., Seventh Report of the International Committee on Taxonomy of Viruses. (Academic Press, San Diego, Wien, New York, 2000). (online version http://www.virustaxonomyonline.com/)

Vandamme et al., Use of a generic polymerase chain reaction assay detecting human T-lymphotropic virus (HTLV) types I, II and divergent simian strains in the evaluation of individuals with indeterminate HTLV serology. *J. Med. Virol.* 52, 1-7 (1997).

Wolfe et al., 2005. Emergence of unique primate T-lymphotropic viruses among central African bushmeat hunters. *Proc. Natl. Acad. Sci. USA.* 102:7994-7999.

Wolfe et al., 2004. Exposure to nonhuman primates in rural Cameroon. *Emerg. Infect. Dis.* 10, 2094 (2004).

Wolfe et al., Naturally acquired simian retrovirus infections in central African hunters. *Lancet* 363, 932-937 (2004b).

Wolfe et al., Simian retroviral infections in human beings. *Lancet* 364, 139-140 (2004c).

Womble 2000. GCG: The Wisconsin Package of sequence analysis programs. *Methods Mol. Biol.* 132:3-22.

Yamashita et al., Molecular Epidemiology of HTLV-I in the world. *J Acquir Immune Defic Syndr Hum Retrovirol.* 13: S124-31 (1996).

SEQUENCES

SEQ ID NO: 1 (HTLV-3 pol) (pos 2407-5076)
SEQ ID NO: 2 (HTLV-4 pol) (pos 3-2549)
SEQ ID NO: 3 (HTLV-3 env) (pos 5069-6544)
SEQ ID NO: 4 (HTLV-4 env) (pos 2542-3999)
SEQ ID NO: 5 (HTLV-3 tax)
SEQ ID NO: 6 (HTLV-4 tax)
SEQ ID NO: 7 (PTLVTPG)
SEQ ID NO: 8 (PGTAXR1)
SEQ ID NO: 9 (PH2Rrev)
SEQ ID NO: 10 (PGTAXR2)
SEQ ID NO: 11 (PGPOLF1)
SEQ ID NO: 12 (PGPOLR1)
SEQ ID NO: 13 (PGPOLF2)
SEQ ID NO: 14 (PGPOLR2)
SEQ ID NO: 15 (1863TF1)
SEQ ID NO: 16 (1863TR1)
SEQ ID NO: 17 (1863TF2)
SEQ ID NO: 18 (1863TR2)
SEQ ID NO: 19 (5VLTRext)
SEQ ID NO: 20 (1MNDR1)
SEQ ID NO: 21 (Enh280)
SEQ ID NO: 22 (1MNDR2)
SEQ ID NO: 23 (PH1F)
SEQ ID NO: 24 (PH2R)
SEQ ID NO: 25 (PH2F)
SEQ ID NO: 26 (PH2R)
SEQ ID NO: 27 (PGENVF1)
SEQ ID NO: 28 (PGENVR1)
SEQ ID NO: 29 (PGENVF2)
SEQ ID NO: 30 (PGENVR2)
SEQ ID NO: 31 (GPLTRF1)
SEQ ID NO: 32 (GPLTRR1)
SEQ ID NO: 33 (GPLTRF2)
SEQ ID NO: 34 (GPLTRR2)
SEQ ID NO: 35 (HTLV-3 gag) (pos 756-2023)
SEQ ID NO: 36 (HTLV-3 Complete genome: 2026ND.seq (8917 bp)
SEQ ID NO: 37 (HTLV-3 env amino acid)
SEQ ID NO: 38 (HTLV-3 env surface antigen (SU)=aa 1-315)
SEQ ID NO: 39 (HTLV-3 env transmembrane=aa 316-491)
SEQ ID NO: 40 (HTLV-3 gag amino acid)
SEQ ID NO: 41 (HTLV-3 gag p15=aa 337-422)
SEQ ID NO: 42 (HTLV-3 gag p19=aa 1-123)
SEQ ID NO: 43 (HTLV-3 gag p24=aa 124-336)
SEQ ID NO: 44 (HTLV-3 pol) amino acid
SEQ ID NO: 45 (HTLV-3 LTR) (pos 1-697 & 8221-8917)
SEQ ID NO: 46 (HTLV-3 pro) amino acid
SEQ ID NO: 47 (HTLV-3 pro) (pos 1976-2509)
SEQ ID NO: 48 (HTLV-3 rex) amino acid
SEQ ID NO: 49 (HTLV-3 rex)(pos 5010-5071.7245-7730)
SEQ ID NO: 50 (HTLV-3 tax) amino acid
SEQ ID NO: 51 (HTLV-3 tax) (pos5069-5071.7244-8293)
SEQ ID NO: 52 (HTLV-3 pX (pos 6545-7243)
SEQ ID NO: 53 (HTLV-4 pol-env-tax region)
SEQ ID NO: 54 (HTLV-4 env) amino acid
SEQ ID NO: 55 (HTLV-4 env surface antigen (SU)=aa 1-307)
SEQ ID NO: 56 (HTLV-4 env transmembrane=aa 308-485)
SEQ ID NO: 57 (HTLV-4 pot) amino acid
SEQ ID NO: 58 (HTLV-4 pro) amino acid
SEQ ID NO: 59 (HTLV-4 pro) (pos 1-273)
SEQ ID NO: 60 (HTLV-4 rex) amino acid
SEQ ID NO: 61 (HTLV-4 rex) (pos 2483-2545.4560-5009)
SEQ ID NO: 62 (HTLV-4 tax) amino acid
SEQ ID NO: 63 (HTLV-4-pX) (pos. 4000-4558)
SEQ ID NO: 64 1863 PF1
SEQ ID NO: 65 1863PR2
SEQ ID NO: 66 1863PP2 FAM (fluorescent labeled probe)
SEQ ID NO: 67 region of HTLV-3 where type specific peptides of HTLV-1 and HTLV-2 are located
SEQ ID NO: 68 region of HTLV-4 where type specific peptides of HTLV-1 and HTLV-2 are located
SEQ ID NO: 69 2026LF1
SEQ ID NO: 70 2026PR1
SEQ ID NO: 71 2026LF2
SEQ ID NO: 72 2026PR2
SEQ ID NO: 73 2026 PF3
SEQ ID NO: 74 2026ER1
SEQ ID NO: 75 2026 PF2
SEQ ID NO: 76 2026ER3
SEQ ID NO: 77 2026EF1
SEQ ID NO: 78 2026LR1
SEQ ID NO: 79 2026EF3
SEQ ID NO: 80 2026LR2
SEQ ID NO: 81 (HTLV-4(1863LE) Complete genome)
SEQ ID NO: 82 (GTTAAAC)
SEQ ID NO: 83 (TTTAAAC)
SEQ ID NO: 84 HTLV-3 HBZ

The invention claimed is:

1. An isolated primate T-lymphotropic virus (PTLV) polypeptide, wherein the polypeptide is a HTLV-3 or HTLV-4 gag, pol, env, tax, rex or pro protein selected from the group consisting of:
   (i) a HTLV-3 gag protein encoded by a nucleic acid sequence at least 91.5% identical to SEQ ID NO: 35;
   (ii) a HTLV-3 pol protein encoded by a nucleic acid sequence at least 92.8% identical to SEQ ID NO: 1;
   (iii) a HTLV-3 env protein encoded by a nucleic acid sequence at least 92.5% identical to SEQ ID NO: 3;
   (iv) a HTLV-3 tax protein encoded by a nucleic acid sequence at least 94.2% identical to SEQ ID NO: 5;
   (v) a HTLV-3 rex protein encoded by a nucleic acid sequence comprising SEQ ID NO: 49;
   (vi) a HTLV-3 pro protein encoded by a nucleic acid sequence comprising SEQ ID NO: 47;
   (vii) a HTLV-4 gag protein encoded by a nucleic acid sequence comprising nucleotides 750-2024 of SEQ ID NO: 81;
   (viii) a HTLV-4 pol protein encoded by a nucleic acid sequence at least 71.5% identical to SEQ ID NO: 2;
   (ix) a HTLV-4 env protein encoded by a nucleic acid sequence at least 73.5% identical to SEQ ID NO: 4;
   (x) a HTLV-4 tax protein encoded by a nucleic acid sequence at least 82% identical to SEQ ID NO: 6;
   (xi) a HTLV-4 rex protein encoded by a nucleic acid sequence comprising SEQ ID NO: 61; and
   (xii) a HTLV-4 pro protein encoded by a nucleic acid sequence comprising SEQ ID NO: 59.

2. The isolated PTLV polypeptide of claim 1, wherein the protein is encoded by a nucleic acid sequence comprising SEQ ID NO: 35; SEQ ID NO: 1; SEQ ID NO: 3; SEQ ID NO: 5; SEQ ID NO: 49; SEQ ID NO: 47; nucleotides 750-2024 of SEQ ID NO: 81; SEQ ID NO: 2; SEQ ID NO: 4; SEQ ID NO: 6; SEQ ID NO: 61 or SEQ ID NO: 59.

3. The isolated PTLV polypeptide of claim 1, wherein the protein comprises:
   (i) an amino acid sequence having at least 95% homology to the amino acid sequence set forth as SEQ ID NO: 40, SEQ ID NO: 44, SEQ ID NO: 37, SEQ ID NO: 50, SEQ ID NO: 48, SEQ ID NO: 46, SEQ ID NO: 57, SEQ ID NO: 54, SEQ ID NO: 62, SEQ ID NO: 60, or SEQ ID NO: 58;
   (ii) a conservative substitution of 1 or 2 amino acids of the amino acid sequence set forth as one of SEQ ID NO: 40, SEQ ID NO: 44, SEQ ID NO: 37, SEQ ID NO: 50, SEQ ID NO: 48, SEQ ID NO: 46, SEQ ID NO: 57, SEQ ID NO: 54, SEQ ID NO: 62, SEQ ID NO: 60, or SEQ ID NO: 58; or
   (iii) a deletion of 2 to 6 amino acids of the amino acid sequence set forth as one of SEQ ID NO: 40, SEQ ID NO: 44, SEQ ID NO: 37, SEQ ID NO: 50, SEQ ID NO: 48, SEQ ID NO: 46, SEQ ID NO: 57, SEQ ID NO: 54, SEQ ID NO: 62, SEQ ID NO: 60, or SEQ ID NO: 58.

4. The isolated PTLV polypeptide of claim 1, wherein the amino acid sequence of the protein comprises SEQ ID NO: 40, SEQ ID NO: 44, SEQ ID NO: 37, SEQ ID NO: 50, SEQ ID NO: 48, SEQ ID NO: 46, SEQ ID NO: 57, SEQ ID NO: 54, SEQ ID NO: 62, SEQ ID NO: 60, or SEQ ID NO: 58.

5. The isolated PTLV polypeptide of claim 1, wherein the amino acid sequence of the protein consists of SEQ ID NO: 40, SEQ ID NO: 44, SEQ ID NO: 37, SEQ ID NO: 50, SEQ ID NO: 48, SEQ ID NO: 46, SEQ ID NO: 57, SEQ ID NO: 54, SEQ ID NO: 62, SEQ ID NO: 60, or SEQ ID NO: 58.

6. A method for detecting antibodies to a PTLV in a biological sample, comprising contacting the biological sample with the polypeptide of claim 1, wherein binding of antibodies from the biological sample to the polypeptide indicates the presence of antibodies to the PTLV in the biological sample.

7. The method of claim 6, wherein the PTLV is HTLV-3 or HTLV-4.

8. The method of claim 6, wherein the biological sample comprises a body fluid sample.

9. A kit for detecting the presence of antibodies that bind a PTLV in a sample, wherein the kit comprises at least one polypeptide of claim 1.

10. The kit of claim 9, wherein the PTLV is HTLV-3 or HTLV-4.

11. The method of claim 6, wherein the protein is encoded by a nucleic acid sequence comprising SEQ ID NO: 35; SEQ ID NO: 1; SEQ ID NO: 3; SEQ ID NO: 5; SEQ ID NO: 49; SEQ ID NO: 47; nucleotides 750-2024 of SEQ ID NO: 81; SEQ ID NO: 2; SEQ ID NO: 4; SEQ ID NO: 6; SEQ ID NO: 61 or SEQ ID NO: 59.

12. The method of claim 6, wherein the protein comprises:
   (i) an amino acid sequence having at least 95% homology to the amino acid sequence set forth as SEQ ID NO: 40, SEQ ID NO: 44, SEQ ID NO: 37, SEQ ID NO: 50, SEQ ID NO: 48, SEQ ID NO: 46, SEQ ID NO: 57, SEQ ID NO: 54, SEQ ID NO: 62, SEQ ID NO: 60, or SEQ ID NO: 58;
   (ii) a conservative substitution of 1 or 2 amino acids of the amino acid sequence set forth as one of SEQ ID NO: 40, SEQ ID NO: 44, SEQ ID NO: 37, SEQ ID NO: 50, SEQ ID NO: 48, SEQ ID NO: 46, SEQ ID NO: 57, SEQ ID NO: 54, SEQ ID NO: 62, SEQ ID NO: 60, or SEQ ID NO: 58; or
   (iii) a deletion of 2 to 6 amino acids of the amino acid sequence set forth as one of SEQ ID NO: 40, SEQ ID NO: 44, SEQ ID NO: 37, SEQ ID NO: 50, SEQ ID NO: 48, SEQ ID NO: 46, SEQ ID NO: 57, SEQ ID NO: 54, SEQ ID NO: 62, SEQ ID NO: 60, or SEQ ID NO: 58.

13. The method of claim 6, wherein the amino acid sequence of the protein comprises SEQ ID NO: 40, SEQ ID NO: 44, SEQ ID NO: 37, SEQ ID NO: 50, SEQ ID NO: 48, SEQ ID NO: 46, SEQ ID NO: 57, SEQ ID NO: 54, SEQ ID NO: 62, SEQ ID NO: 60, or SEQ ID NO: 58.

14. The method of claim 6, wherein the amino acid sequence of the protein consists of SEQ ID NO: 40, SEQ ID NO: 44, SEQ ID NO: 37, SEQ ID NO: 50, SEQ ID NO: 48, SEQ ID NO: 46, SEQ ID NO: 57, SEQ ID NO: 54, SEQ ID NO: 62, SEQ ID NO: 60, or SEQ ID NO: 58.

* * * * *